(12) United States Patent
Beebe et al.

(10) Patent No.: US 12,403,111 B2
(45) Date of Patent: Sep. 2, 2025

(54) COMPOSITIONS AND METHODS FOR TREATING NEURODEVELOPMENTAL DISORDERS

(71) Applicants: SynGAP Research Fund, San Diego, CA (US); UNIVERSITY OF UTAH RESEARCH FOUNDATION, Salt Lake City, UT (US)

(72) Inventors: Katherine Beebe, Salt Lake City, UT (US); Clement Y. Chow, Salt Lake City, UT (US); Mike Graglia, Mill Valley, CA (US); Marta Caceres Dahiya, Arlington, TX (US); Kathryn Helde, Seattle, WA (US); Lindsay Wieczorek, Chaska, MN (US)

(73) Assignees: SynGAP Research Fund, San Diego, CA (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 19/042,105

(22) Filed: Jan. 31, 2025

(65) Prior Publication Data
US 2025/0248959 A1    Aug. 7, 2025

Related U.S. Application Data

(60) Provisional application No. 63/549,394, filed on Feb. 2, 2024.

(51) Int. Cl.
*A61K 31/197* (2006.01)
*A61P 25/08* (2006.01)

(52) U.S. Cl.
CPC ............ *A61K 31/197* (2013.01); *A61P 25/08* (2018.01)

(58) Field of Classification Search
CPC ........................... A61K 31/197; A61P 25/08
USPC ..................................................... 514/561
See application file for complete search history.

(56) References Cited

U.S. PATENT DOCUMENTS

| | | |
|---|---|---|
| 10,905,670 B2 | 2/2021 | Factor et al. |
| 11,793,782 B2 | 10/2023 | Factor |
| 12,145,899 B2 | 11/2024 | Mann |
| 2020/0338034 A1 | 10/2020 | Factor |
| 2022/0142959 A1 | 5/2022 | Factor et al. |
| 2023/0210799 A1 | 7/2023 | Strupp |

OTHER PUBLICATIONS

Kaya et al Brain Communications 2020, pp. 1-19 (Year: 2020).*
Chow Presentation, Nov. 30, 2023, Orlando, FL, SYNGAP1 Science Conference by SynGAP Research Fund.
Bourgeron, T. The genetics and neurobiology of ESSENCE: The third Birgit Olsson lecture. Nord. J. Psychiatry 70, 1-9 (2016).
Talantseva, O. I. et al. The global prevalence of autism spectrum disorder: A three-level meta-analysis. Front. Psychiatry 14, 1071181 (2023).
Zeidan, J. et al. Global prevalence of autism: A systematic review update. Autism Res. 15, 778-790 (2022).
American Psychiatric Association, DSM-5 Task Force. Diagnostic and Statistical Manual of Mental Disorders: DSM-5TM, 5th Ed Text Revision. xliv, 947, pp. 1-9 and 130-207 (2022). oi: 10.1176/appi.books.9780890425596.
Baio, J. et al. Prevalence of Autism Spectrum Disorder Among Children Aged 8 Years—Autism and Developmental Disabilities Monitoring Network, 11 Sites, United States, 2014. Morb. Mortal. Wkly. Rep. Surveill. Summ. Wash. DC 2002 67, 1-23 (2018).
Thapar, A., Cooper, M. & Rutter, M. Neurodevelopmental disorders. Lancet Psychiatry 4, 339-346 (2017).
Rolland, T. et al. Phenotypic effects of genetic variants associated with autism. Nat. Med. 29, 1671-1680 (2023).
Syngap Research Fund. Drug Repurpose Update #1—Acetyl-Leucine for potential management of SynGAP1-related disorder symptoms. Posted on Apr. 23, 2024. Accessed on Jan. 28, 2025. https://curesyngap1.org/blog/drug-repurpose-update-1-tanganil-acetyl-leucine-for-potential management-of-syngap1-related-disorder-symptoms/.
Syngap Research Fund. Drug Repurposing Update #2: Acetyl-Leucine—Potential Mechanisms of Drug Action. Posted on May 24, 2024. Accessed on Jan. 28, 2025. https://curesyngap1.org/blog/drug-repurposing-update-2-tanganil-acetyl-leucine-potential-mechanisms-of-drug-action/.
AQNEURSA™ (levacetylleucine) for oral suspension, Full Prescribing Information, Sep. 2024.
Churchill, G. C. et al. Acetylation turns leucine into a drug by membrane transporter switching. Sci. Rep. 11, 15812 (2021).

(Continued)

*Primary Examiner* — Yevgeny Valenrod
(74) *Attorney, Agent, or Firm* — Davidson Kappel LLC

(57) ABSTRACT

Methods of treating neurodevelopmental disorders by administering an acetylated amino acid having a carbon-nitrogen bond and acetyl group covalently bound to the nitrogen of the carbon-nitrogen bond and having a three-dimensional structure that allows the acetylated amino acid to enter cells and neurons are described. In one embodiment, the acetylated amino acid is a compound of Formula (I):

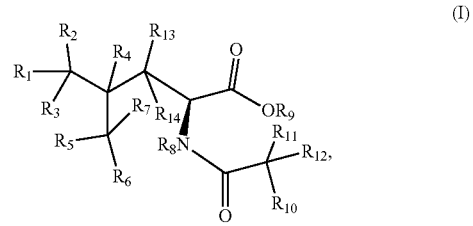

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, or a pharmaceutically acceptable salt thereof. Pharmaceutical compositions containing the acetylated amino acid are also described.

20 Claims, 29 Drawing Sheets

(56) References Cited

OTHER PUBLICATIONS

Hegdekar et al., N-Acetyl-1-leucine improves functional recovery and attenuates cortical cell death and neuroinflammation after traumatic brain injury in mice, Scientific Reports, 11;9249 (2021).

* cited by examiner

| Case # | Sex | Age | Weight (kg) | Affected gene | Mutation | Weeks on NAL | NAL dose (g) | Max NAL dose by weight (mg/kg) | NAL effect at the longest interval | | | | | |
|---|---|---|---|---|---|---|---|---|---|---|---|---|---|---|
| | | | | | | | | | Seizures | Sleep | Communication | Behaviors | Physical ability | Overall Responses |
| 1 | M | 8 | 23 | SYNGAP1 | PTV | 26 | 2 | 88 | ++ | ++ | ++ | ++ | ++ | Positive |
| 2 | M | 8 | 27 | SYNGAP1 | PTV | 17 | 1-1.5 | 56 | . | . | + | - | + | Mixed |
| 3 | F | 21 | 61 | SYNGAP1 | PTV | 17 | 0.5-1 | 16 | . | ++ | + | ++ | ++ | Positive |
| 4 | F | 6 | 25 | SYNGAP1 | PTV | 18 | 1-2 | 80 | . | + | + | + | ++ | Positive |
| 5 | F | 13 | 36 | SYNGAP1 | MS | 9 | 0.5-2 | 56 | . | - | + | . | . | None |
| 6 | M | 7 | 27 | SYNGAP1 | PTV | 7 | 1-3 | 110 | - | + | + | - | + | Mixed |
| 7 | F | 9 | 40 | SYNGAP1 | PTV | 3 | 0.5-1 | 25 | . | - | + | - | . | Mixed |
| 8 | M | 14 | 93 | SYNGAP1 | PTV | 7 | 1 | 11 | . | -- | + | . | + | Mixed |
| 9 | F | 2 | 13 | SYNGAP1 | PTV | 11 | 0.5 | 39 | . | . | + | + | + | Positive |
| 10 | M | 4 | 15 | SYNGAP1 | NR | 11 | 0.3-0.5 | 33 | + | . | + | . | . | Positive |
| 11 | F | 15 | 52 | SYNGAP1 | PTV | 10 | 1-3 | 58 | . | + | + | . | + | Positive |
| 12 | M | 3 | 17 | SYNGAP1 | PTV | 10 | 0.3-0.5 | 30 | . | . | ++ | + | ++ | Positive |
| 13 | M | 18 | 95 | SYNGAP1 | MS | 2 | 0.5-1 | 10 | . | . | . | . | . | None |
| 14 | M | 6 | 23 | SYNGAP1 | PTV | 4 | 1 | 43 | . | ++ | + | + | . | Positive |
| 15 | F | 6 | 20 | SYNGAP1 | PTV | 12 | 1.5 | 75 | . | . | + | . | ++ | Positive |
| 16 | M | 3 | 16 | SYNGAP1 | PTV | 3 | 0.5-2 | 126 | . | . | NR | NR | NR | None |
| 17 | M | 4 | 20 | SYNGAP1 | PTV | 13 | 0.5-1.5 | 75 | . | . | + | + | + | Positive |
| 18 | F | 5 | 19 | SYNGAP1 | NR | 4 | 0.5-1.5 | 81 | . | . | + | . | + | Positive |
| 19 | F | 3 | 14 | SYNGAP1 | PTV | 4 | 0.5 | 37 | . | . | . | . | . | None |
| 20 | F | 3 | 16 | SYNGAP1 | NR | 6 | 0.3-0.5 | 31 | . | ++ | ++ | + | + | Positive |
| 21 | F | 7 | 19 | SYNGAP1 | NR | 2 | 0.1-0.3 | 13 | . | . | . | + | . | Positive |
| 1 | F | 4 | 20 | SLC6A1 | NR | 4 | 2 | 98 | . | . | + | - | + | Mixed |
| 2 | F | 5 | 22 | SLC6A1 | NR | 2 | 2 | 92 | . | . | + | - | + | Mixed |
| 3 | F | 12 | 23 | SLC6A1/DS | MS | 12 | 0.3-1 | 44 | . | . | . | . | . | Mixed |
| 4 | M | 8 | 27 | SLC6A1 | LOF | 3 | 0.2-1 | 37 | . | - | ++ | . | . | Mixed |
| 1 | M | 3 | 15 | MED13L | PTV | 13 | 1-4 | 259 | . | . | ++ | . | ++ | Positive |
| 2 | NA | 11 | 23 | MED13L | PTV | 3 | 0.5-2 | 86 | . | . | . | . | . | None |
| 3 | F | 3 | NR | MED13L | NR | 5 | 1-1.5 | NA | . | . | ++ | . | ++ | Positive |
| 1 | F | 7 | 14 | CTNNB1 | NR | 5 | 0.5-1 | 60 | . | . | + | . | + | Positive |
| 2 | F | 6 | 32 | CTNNB1 | PTV | 7 | 2 | 63 | . | . | + | + | + | Positive |

PTV = protein truncating variant
MS = missense
LOF = loss of function
NR = not reported

FIG. 9

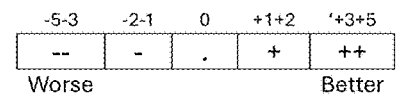

| -5 -3 | -2 -1 | 0 | +1 +2 | +3 +5 |
|---|---|---|---|---|
| -- | - | . | + | ++ |

Worse                  Better

Other forms of leucine do not work

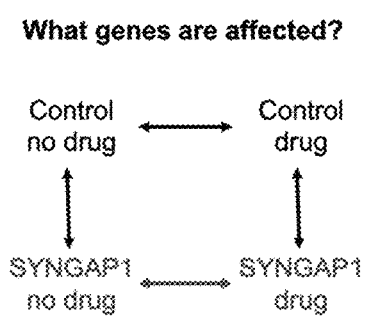
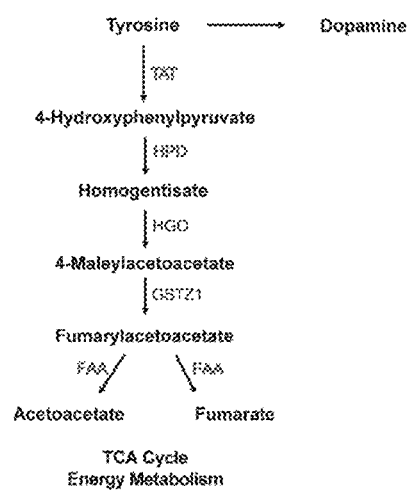
FIG. 42C

COMPOSITIONS AND METHODS FOR TREATING NEURODEVELOPMENTAL DISORDERS

CROSS REFERENCE TO RELATED APPLICATIONS

This application claims the benefit of and priority to U.S. Provisional Application No. 63/549,394, filed on Feb. 2, 2024, the entire content of which is herein incorporated by reference in its entirety.

BACKGROUND

Neurodevelopmental disorders (NDDs) are a broad and heterogeneous group of conditions associated with developmental deficits that produce lifelong impairments in personal, social, academic, or occupational functioning. These disorders typically manifest early in development and include a broad range of symptoms affecting cognitive, motor, language, and social skills.

Specific features of NDDs vary widely and include cognitive impairments, such as difficulties with attention, executive function, and memory; language and communication deficits, including delayed speech and difficulty understanding or using language; behavior problems, including aggression, hyperactivity, and elopement; social interaction challenges; repetitive behaviors and restricted interests; motor coordination problems; sensory processing issues; and epilepsy. The combination and severity of these features can vary significantly and can impact multiple domains of functioning.

The prevalence of NDDs is significant, affecting over 10% of children globally. Prominent features of NDDs include Autism Spectrum Disorder (ASD, affecting 1% of individuals), Intellectual Disability (ID, affecting 1-3% of individuals), and Attention-Deficit Disorder (ADD, affecting ~5% of individuals).

Individuals with NDDs typically need continuous care and support. Financial, emotional, and psychological impacts of NDDs on families can be profound.

Current clinical management of NDDs is multidisciplinary and tailored to the individual's needs. Interventions typically include behavioral, speech, occupational and physical therapies. Medications may be prescribed to manage symptoms like hyperactivity, inattention, mood disorders, and seizures. Due to the diversity and severity of symptoms, appropriate care and treatment of individuals with NDDs is challenging, sometimes inaccessible, expensive and not always effective.

One NDD is SYNGAP1-Related Disorder, a developmental and epileptic encephalopathy. SYNGAP1-Related Disorder is an autosomal dominant rare genetic disorder associated with developmental delay (DD) or intellectual disability (ID) (100% of affected individuals), generalized epilepsy (~84%), and autism spectrum disorder (ASD), and other behavioral abnormalities (≤50%).

SYNGAP1-Related Disorder is caused by a mutation in the SYNGAP1 gene. The SYNGAP1 gene is located on Chromosome 6 and encodes for a synaptic Ras-GTPase activating protein ("SynGAP protein") that is highly expressed in excitatory neurons. The pathogenic mutation in the SYNGAP1 gene leads to the gene not producing enough SynGAP protein, or a disrupted SynGAP protein.

Without the proper amount and function of SynGAP protein, an increase in excitability in the synapses occurs, making it difficult for neurons to communicate effectively. This leads to many neurological issues seen in SYNGAP1 individuals. For example, loss of SYNGAP1 in neurons may result in a loss of synaptic plasticity and increased excitability resulting in seizures. SynGAP protein is also found in cilia in many cell types. Aberrant cilia formation or function may also lead to and/or intensify neurologic and other issues in SYNGAP1-Related Disorder.

SYNGAP1 variants are surprisingly common, with the incidence reported as 6 per 100,000 or 1 per 16,000 individuals. This comprises approximately 1-2% of all Intellectual Disability (ID) cases, making it one of the most common genetic causes of ID, similar to more well-known syndromes like Fragile X, Angelman and Rett.

There is currently no cure or specific treatment for the underlying condition that causes SYNGAP1-Related Disorder. The most common therapies available are physical therapy, occupational therapy, speech therapy, developmental therapy and applied behavioral analysis (ABA) therapy. Other available therapies include antiepileptic, sleep, behavioral, and anxiety medications. For a percentage of those affected, feeding tubes and other surgeries or procedures are also standard.

Amino acids are building blocks that the human body uses to make proteins, repair tissues, create energy, and make hormones and neurotransmitters.

Leucine is one of the amino acids. Leucine exists in two forms: D-leucine and L-leucine. D-leucine and L-leucine are stereoisomers; they have the same chemical components but differ in their three-dimensional structures. The human body cannot produce leucine on its own and must obtain it through diet.

Acetylated leucine is created when an acetyl group (a chemical group made up of two carbon atoms, three hydrogen atoms, and one oxygen atom) is covalently conjugated to a leucine molecule. This modification can occur on either the D or L form of leucine, forming either N-acetyl-L-leucine (NALL) or N-acetyl-D-leucine. The combination of NALL and N-acetyl-D-leucine is called acetyl-DL-leucine or NAL.

NAL is available over-the-counter in France for treatment of vestibular-related imbalance and vertigo under the trade name Tanganil® (Pierre Fabre Laboratories). In addition to vestibular-related imbalance and vertigo, it has also been explored as a potential treatment for cerebellar ataxia, lysosomal storage disorders, migraine, restless legs syndrome, as well as a decline in cognition and mobility in the elderly, none of which are neurodevelopmental disorders.

N-acetyl-L-leucine (NALL), one of the stereoisomers of NAL, is approved by US FDA for treatment of Niemann-Pick disease type C. Niemann-Pick disease type C is a lysosomal storage disorder that affects the body's ability to break down and use fats (i.e., cholesterol and lipids) inside cells, it is not a neurodevelopmental disorder.

NALL is also being explored in clinical trials for the treatment of $GM_2$ gangliosidoses (Tay-Sachs and Sandhoff diseases) and Louis-Bar syndrome, which are not neurodevelopmental disorders.

A monocarboxylate transporter 1 (MCT1) is a transmembrane protein encoded by the SLC16 gene family involved in the proton-coupled transport of L-lactate, ketone bodies, and pyruvate. A deficiency MCT1 is an autosomal dominant and recessive disease on the SLC16A1/MCT1 gene on chromosome 1p13.2. Intellectual disability is one of the symptoms associated with MCT1 deficiency.

SUMMARY OF THE INVENTION

It is an object of the invention to provide pharmaceutical compositions and treatments for neurodevelopmental disorders including, e.g., SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Attention-Deficit Disorder (ADD), Intellectual Disability (ID), and other developmental and epileptic encephalopathies (DEEs). In the context of the present specification, neurodevelopmental disorders do not include Niemann-Pick diseases, Tay-Sachs disease, Sandhoff disease, GM1 gangliosidosis, Fabry disease, and Louis-Bar syndrome.

It is a further object of the invention to provide pharmaceutical compositions and treatments for a developmental and epileptic encephalopathy.

It is an additional object of the invention to provide pharmaceutical compositions and treatments for SYNGAP1-Related Disorder.

It is a further object of the invention to provide pharmaceutical compositions and treatments for Autism Spectrum Disorder.

It is a further object of the invention to provide pharmaceutical compositions and treatments for Attention-deficit Disorder.

It is a further object of the invention to provide pharmaceutical compositions and treatments for intellectual disability.

It is a further object of the invention to provide pharmaceutical compositions and treatments that improve communications of a subject with a neurodevelopmental disorder.

It is a further object of the invention to provide pharmaceutical compositions and treatments that improve physical abilities of a subject with a neurodevelopmental disorder.

It is a further object of the invention to provide pharmaceutical compositions and treatments that improve behavior of a subject with a neurodevelopmental disorder.

It is a further object of the invention to provide pharmaceutical compositions and treatments that decrease seizure frequency in a subject with a neurodevelopmental disorder.

It is a further object of the invention to provide pharmaceutical compositions and treatments that decrease sleep disturbances in a subject with a neurodevelopmental disorder.

It is an additional object of the invention to provide pharmaceutical compositions and treatments that improve quality of life of a subject with a neurodevelopmental disorder and/or his or her caregivers.

In accordance with these objects and others, the invention provides a method of treating a neurodevelopmental disorder in a subject in need thereof comprising administering to the subject a therapeutically effective amount of an acetylated amino acid, the acetylated amino acid comprising an acetyl group covalently bound to an amino acid having a carbon-nitrogen bond, the acetylated amino acid having a three-dimensional structure that allows the acetylated amino acid to enter cells and neurons and provide its therapeutic effects via a route or mechanism that is unavailable to and cannot be utilized by the amino acid.

The three-dimensional structure of the acetylated amino acid may, e.g., allow the acetylated amino acid to interact with and enter cells and neurons through a transport protein MCT1. This way, when MCT1 transports one molecule of the acetylated amino acid into the cell, it may transport one molecule of lactate out of the cell. The acetylated amino acid may, therefore, help cells to get rid of lactate, which in high concentrations can cause low pH levels responsible for one or more symptom(s) of a neurodevelopmental disorder, and, therefore, alleviate severity of one or more symptom(s) of a neurodevelopmental disorder.

The three-dimensional structure of the acetylated amino acid may also allow the acetylated amino to modulate how cells and neurons balance growth and clean up damaged parts. For example, once inside cells and neurons, the acetylated amino acid may inhibit a protein complex mTORC1. The inhibition of TOR1 may promote the process of autophagy. The promotion of autophagy may, in turn, help remove damaged or misfolded proteins and reduce inflammation in the brain and alleviate severity of one or more symptom(s) of a neurodevelopmental disorder. In addition, the inhibition of TOR1 may regulate the process of localized translation of RNA into protein within the cell. The regulation of localized translation may help protein to be expressed in the proper subcellular location and alleviate severity of one or more symptom(s) of a neurodevelopmental disorder.

The three-dimensional structure of the acetylated amino acid may further allow the acetylated amino to improve how cells and neurons utilize glucose for energy and thereby enhance brain activity and alleviate severity of one or more symptom(s) of a neurodevelopmental disorder. In one embodiment, the acetylated amino acid may improve glucose usage in areas of the brain responsible for the occurrence of symptoms of a neurodevelopmental disorder, leading to an alleviation severity of one or more symptom(s) of the neurodevelopmental disorder (e.g., leading to better balance and coordination and/or improved communications).

The administration of the acetylated amino acid in accordance with the present invention allows, e.g., for an alleviation of a severity of one or more symptom(s) of the neurodevelopmental disorder in the subject. The symptom the severity of which may be alleviated by the administration of the acetylated amino acid in accordance with the present invention include, e.g., frequency and type of seizures, sleep disturbances, ataxia, impairments of motor function, impairments in communication, apraxia, decreased social awareness, developmental delays, intellectual disability, autistic features, behavior abnormalities, and combinations of any of the foregoing.

The administration of the acetylated amino acid having the carbon-nitrogen bond and acetyl group covalently bound to the nitrogen of the carbon-nitrogen bond in accordance with the present invention may also improve communications and/or physical abilities and/or behavior of the subject with a neurodevelopmental disorder. Improvements in communications provided by the administration of the acetylated amino acid in accordance with the present invention include improvements in understanding and expressive language. Improvements in physical abilities provided by the administration of the acetylated amino acid in accordance with the present invention include improvements in fine and gross motor skills, coordination, and focus.

The administration of the acetylated amino acid having the carbon-nitrogen bond and acetyl group covalently bound to the nitrogen of the carbon-nitrogen bond in accordance with the present invention may therefore improve quality of life of the subject and/or caregiver(s) of the subject.

In the methods of the invention, the acetylated amino acid having a carbon-nitrogen bond and acetyl group covalently bound to the nitrogen of the carbon-nitrogen bond may be administered by itself or together with its stereoisomer. For example, the acetylated amino acid having a carbon-nitrogen bond and acetyl group covalently bound to the nitrogen of the carbon-nitrogen bond may be an L-enantiomer and be administered by itself, or it may be administered together with a D-enantiomer of the acetylated amino acid.

In the methods of the invention, the acetylated amino acid having a carbon-nitrogen bond and acetyl group covalently bound to the nitrogen of the carbon-nitrogen bond may also be administered in combination with one or more additional active pharmaceutical ingredients.

In one embodiment, the acetylated amino acid used in the method of the invention is a compound of Formula (I):

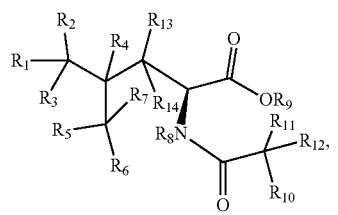
(I)

wherein
(i) $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D; or
(ii); $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, and at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is H; or
(iii) $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, and at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is D; or
(iv) $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each H;
or a pharmaceutically acceptable salt thereof.

In an additional embodiment, the acetylated amino acid used in the method of the invention is a compound of Formula (I):

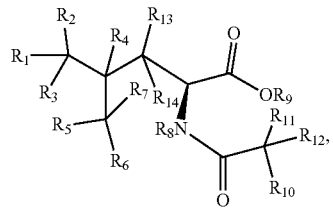
(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, or a pharmaceutically acceptable salt thereof.

In an additional embodiment, the acetylated amino acid is a compound of Formula (II):

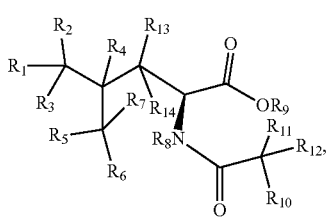
(II)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each H, or a pharmaceutically acceptable salt thereof.

In a further embodiment, the acetylated amino acid is a compound of Formula (III):

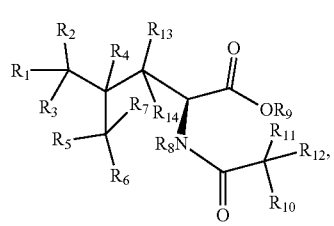
(III)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, and at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is D, or a pharmaceutically acceptable salt thereof.

In an additional embodiment, the acetylated amino acid is a compound of Formula (IV):

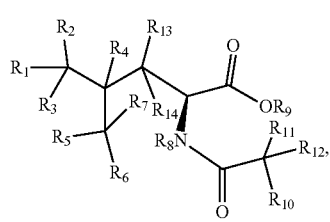
(IV)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D, and at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is H, or a pharmaceutically acceptable salt thereof.

In the methods of the invention, compounds of Formula (I), Formula (II), Formula (III), or Formula (IV) may be administered to a subject in need thereof (i) before the subject is experiencing or exhibiting any symptom(s) of the neurodevelopmental disorder and/or (ii) when the subject is experiencing or exhibiting one or more symptom(s) of the neurodevelopmental disorder and/or (iii) after the one or more symptom(s) of the neurodevelopmental disorder subsided in the subject and the subject is no longer exhibiting symptoms of the neurodevelopmental disorder.

The invention is directed in part to a method of treating a neurodevelopmental disease comprising administering a therapeutically effective amount of a compound of Formula (I), Formula (II), Formula (III), or Formula (IV) to a subject in need thereof, wherein the subject is a carrier of a SYNGAP1 gene mutation. The SYNGAP1 gene mutation may, e.g., be a DNA variant categorized as pathogenic or likely pathogenic, or a variant categorized as a variant of uncertain significance (VUS) which may be present in an individual exhibiting symptoms of SYNGAP1. In one embodiment, the SYNGAP1 gene mutation may, e.g., be a pathogenic mutation or a likely pathogenic mutation. In another embodiment, the SYNGAP1 gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is a carrier of a MED13L gene mutation. The MED13L gene mutation may, e.g., be a DNA variant categorized as pathogenic or likely pathogenic, or a variant categorized as a variant of uncertain significance (VUS) which may be present in an individual exhibiting symptoms of MED13L. In one embodiment, the MED13L gene mutation may, e.g., be a pathogenic mutation or a likely pathogenic mutation. In another embodiment, the MED13L gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is a carrier of a CTNNB1 gene mutation. The CTNNB1 gene mutation may, e.g., be a DNA variant categorized as pathogenic or likely pathogenic, or a variant categorized as a variant of uncertain significance (VUS) which may be present in an individual exhibiting symptoms of CTNNB1. In one embodiment, the CTNNB1 gene mutation may, e.g., be a pathogenic mutation or a likely pathogenic mutation. In another embodiment, the CTNNB1 gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is carrier of a DLG4 gene mutation. The DLG4 gene mutation may, e.g., be a DNA variant categorized as pathogenic or likely pathogenic, or a variant categorized as a variant of uncertain significance (VUS) which may be present in an individual exhibiting symptoms of DLG4. In one embodiment, the DLG4 gene mutation may, e.g., be a pathogenic mutation or a likely pathogenic mutation. In another embodiment, the DLG4 gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is carrier of a KCNT1 gene mutation. The KCNT1 gene mutation may, e.g., be a DNA variant categorized as pathogenic or likely pathogenic, or a variant categorized as a variant of uncertain significance (VUS) which may be present in an individual exhibiting symptoms of KCNT1 epilepsy. In one embodiment, the KCNT1 gene mutation may, e.g., be a pathogenic mutation or a likely pathogenic mutation. In another embodiment, the KCNT1 gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is carrier of a SLC6A1 gene mutation. The SLC6A1 gene mutation may, e.g., be a DNA variant categorized as pathogenic or likely pathogenic, or a variant categorized as a variant of uncertain significance (VUS) which may be present in an individual exhibiting symptoms of SLC6A1-Related disorder. In one embodiment, the SLC6A1 gene mutation may, e.g., be a pathogenic mutation or a likely pathogenic mutation. In another embodiment, the SLC6A1 gene mutation may be a variant of uncertain significance (VUS).

The invention is also directed to a method of treating a neurodevelopmental disease comprising administering a therapeutically effective amount of a compound of Formula (I), Formula (II), Formula (III), or Formula (IV) to a subject in need thereof, wherein the subject is carrier of a FOXG1 gene mutation. The FOXG1 gene mutation may, e.g., be a DNA variant categorized as pathogenic or likely pathogenic, or a variant categorized as a variant of uncertain significance (VUS) which may be present in an individual exhibiting symptoms of FOXG1 syndrome. In one embodiment, the FOXG1 gene mutation may, e.g., be a pathogenic mutation or a likely pathogenic mutation. In another embodiment, the FOXG1 gene mutation may be a variant of uncertain significance (VUS).

The invention is also directed in part to a method of treating SYNGAP1-Related Disorder in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating SLC6A1-Related disorder in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating MED13L syndrome in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating CTNNB1 syndrome in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating DLG4-related synaptopathy in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating FOXG1 syndrome in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating KCNT1 epilepsy in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating Autism Spectrum Disorder in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating Attention-Deficit Disorder (ADD) in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating Intellectual Disability (ID) in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating a developmental and epileptic encephalopathy in a subject in need thereof comprising administering to the subject a therapeutically effective amount of a compound of Formula (I), Formula (II), Formula (III), or Formula (IV), or a pharmaceutically acceptable salt thereof.

The invention is also directed in part to a method of treating a neurodevelopmental disorder in a subject in need thereof comprising administering to the subject a therapeutically effective amount of N-acetyl-L-leucine (NALL), or a pharmaceutically acceptable salt thereof.

The invention is also directed in part to a method of treating a neurodevelopmental disorder in a subject in need thereof comprising improving a symptom of the neurodevelopmental disorder in the subject by orally administering to the subject a therapeutically effective amount of N-acetyl-L-leucine (NALL), or a pharmaceutically acceptable salt thereof, wherein the symptom is selected from a group consisting of seizures, sleep disturbances, behavioral disturbances, and combinations thereof, and the neurodevelopmental disorder is a developmental and epileptic encephalopathy.

The invention is also directed in part to a method of treating a neurodevelopmental disorder in a subject in need thereof comprising improving physical abilities in the subject by orally administering to the subject a therapeutically effective amount of N-acetyl-L-leucine (NALL), or a pharmaceutically acceptable salt thereof, wherein the neurodevelopmental disorder is a developmental and epileptic encephalopathy.

The invention is also directed in part to a method of treating a neurodevelopmental disorder in a subject in need thereof comprising improving a symptom of the neurodevelopmental disorder in the subject by orally administering to the subject a therapeutically effective amount of N-acetyl-L-leucine (NALL), or a pharmaceutically acceptable salt thereof, wherein the symptom is selected from a group consisting of seizures, sleep disturbances, behavioral disturbances, and combinations thereof, and the neurodevelopmental disorder is selected from a group consisting of SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Attention-Deficit Disorder (ADD), and Intellectual Disability (ID).

The invention is also directed in part to a method of treating a neurodevelopmental disorder in a subject in need thereof comprising improving communications in the subject by orally administering to the subject a therapeutically effective amount of N-acetyl-L-leucine (NALL), or a pharmaceutically acceptable salt thereof, wherein the neurodevelopmental disorder is a developmental and epileptic encephalopathy.

The invention is also directed in part to a method of treating a neurodevelopmental disorder in a subject in need thereof comprising improving communications in the subject by orally administering to the subject a therapeutically effective amount of N-acetyl-L-leucine (NALL), or a pharmaceutically acceptable salt thereof, wherein the neurodevelopmental disorder is selected from a group consisting of SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Attention-Deficit Disorder (ADD), and Intellectual Disability (ID).

The invention is also directed in part to a method of treating a neurodevelopmental disorder in a subject in need thereof comprising improving physical abilities in the subject by orally administering to the subject a therapeutically effective amount of N-acetyl-L-leucine (NALL), or a pharmaceutically acceptable salt thereof, wherein the neurodevelopmental disorder is selected from a group consisting of SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Attention-Deficit Disorder (ADD), and Intellectual Disability (ID).

The invention is also directed in part to a method of treating a neurodevelopmental disorder in a subject in need thereof comprising improving behaviors in the subject by orally administering to the subject a therapeutically effective amount of N-acetyl-L-leucine (NALL), or a pharmaceutically acceptable salt thereof, wherein the neurodevelopmental disorder is a developmental and epileptic encephalopathy.

The invention is also directed in part to a method of treating a neurodevelopmental disorder in a subject in need thereof comprising improving behaviors in the subject by orally administering to the subject a therapeutically effective amount of N-acetyl-L-leucine (NALL), or a pharmaceutically acceptable salt thereof, wherein the neurodevelopmental disorder is selected from a group consisting of SYNGAP1-Related Disorder, SLC6A1-Related disorder, MED13L syndrome, CTNNB1 syndrome, DLG4-related synaptopathy, FOXG1 syndrome, KCNT1 epilepsy, Autism Spectrum Disorder (ASD), Attention-Deficit Disorder (ADD), and Intellectual Disability (ID).

The total daily amount of NALL, or a pharmaceutically acceptable salt thereof, administered to the subject in accordance with the methods of the invention may be individualized for the needs of the individual subject and may generally range from about 10 mg to about 5 grams, about 100 mg to about 5 grams, about 250 mg to about 4 grams, or about 500 mg to about 4 grams. The daily amount may be divided into 2 to 8 sub-doses and administered as the sub-doses throughout the day, or may be administered as one dose.

In one embodiment, NALL is administered in a pharmaceutical composition formulated for oral administration. The pharmaceutical composition for oral administration may, e.g., be a tablet, a capsule, a powder formulation (e.g., granules that could be sprinkled on or incorporated in food and/or dissolved in a liquid prior to administration).

In one embodiment, the pharmaceutical compositions for oral administration are provided in the form, shape, size, and dose to be easily hidden or added to a food liked by the individual being treated (e.g., a sandwich cookie filling or a nutella cookie).

The pharmaceutical composition for oral administration may also be provided in the form of a solution consisting of NALL, a solvent and optional pharmaceutically acceptable excipients, wherein NALL is completely dissolved in the solvent.

The frequency of oral administration may range from one to eight times a day. Thus, the pharmaceutical composition formulated for oral administration may, e.g., be administered twice-a-day, three times a day, four times a day, six times a day, or seven times a day.

The invention is also directed in part to a method of treating SYNGAP1-Related Disorder in a subject in need thereof comprising orally administering to the subject from about 50 mg to about 5 grams or 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL is administered orally to the subject per day.

The invention is also directed in part to a method of treating SLC6A1-Related disorder in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL, or a pharmaceutically acceptable salt thereof, is administered to the subject per day.

The invention is also directed in part to a method of treating MED13L syndrome in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL is administered to the subject per day.

The invention is also directed in part to a method of treating CTNNB1 syndrome in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL, or a pharmaceutically acceptable salt thereof, is administered to the subject per day.

The invention is also directed in part to a method of treating DLG4-related synaptopathy in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL, or a pharmaceutically acceptable salt thereof, is administered to the subject per day.

The invention is also directed in part to a method of treating FOXG1 syndrome in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered to the subject per day. In some embodiments, from about 100 mg to about 1.5 grams, about 250 mg to about 2 grams or about 500 mg to about 1.5 grams of NALL, or a pharmaceutically acceptable salt thereof, is administered orally to the subject per day.

The invention is also directed in part to a method of treating Autism Spectrum Disorder in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered to the subject per day. In some embodiments, from about 100 mg to about 1.5 grams, about 250 mg to about 2 grams or about 500 mg to about 1.5 grams of NALL is administered orally to the subject per day.

The invention is also directed in part to a method of treating Attention-Deficit Disorder in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL is administered orally to the subject per day.

The invention is also directed in part to a method of treating intellectual disability in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL, or a pharmaceutically acceptable salt thereof, is administered orally to the subject per day.

The invention is also directed in part to a method of treating a developmental and epileptic encephalopathy in a subject in need thereof comprising orally administering to the subject from about 100 mg to about 5 grams of N-acetyl-L-leucine (NALL), or a pharmaceutically acceptable salt thereof, per day. In some embodiments, from about 100 mg to about 4 grams, about 100 mg to about 3 grams or about 100 mg to about 2 grams of NALL, or a pharmaceutically acceptable salt thereof, is administered orally to the subject per day. In some embodiments, from about 100 mg to about 1.5 grams, about 250 mg to about 2 grams or about 500 mg to about 1.5 grams of NALL, or a pharmaceutically acceptable salt thereof, is administered orally to the subject per day.

The invention is also directed in part to a method of treating a neurodevelopmental disorder in a subject in need thereof comprising orally administering to the subject N-acetyl-L-leucine (NALL), or a pharmaceutically acceptable salt thereof, at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating SYNGAP1-Related Disorder in a subject in need thereof comprising orally administering to the subject N-acetyl-L-leucine (NALL), or a pharmaceutically acceptable salt thereof, at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating SLC6A1-Related disorder in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating MED13L syndrome in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating CTNNB1 syndrome in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating DLG4-related synaptopathy in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating FOXG1 syndrome in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating Autism Spectrum Disorder in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating Attention-Deficit Disorder in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

The invention is also directed in part to a method of treating intellectual disability in a subject in need thereof comprising orally administering to the subject N-acetyl-L-leucine (NALL) at a dose of from about 5 mg/kg/day to about 300 mg/kg/day, about 5 mg/kg/day to about 200 mg/kg/day or about 10 mg/kg/day to about 200 mg/kg/day.

In some of the embodiments of the method of the invention, the daily dose of NALL may be divided into two, three, four, five, six, seven or eight doses and administered orally throughout the day. For example, the daily dose of NALL may be divided into two sub-doses, three sub-doses, four sub-doses, five-sub-doses, six sub-doses, seven-sub-doses, or eight sub-doses and administered two times a day, three times a day, four times a day, five times a day, six times a day, seven times a day, or eight times a day.

In the methods of the invention, NALL may be administered for as long as its therapeutic efficacy is maintained. In some of the embodiments, NALL is administered for 1 to 52 weeks, 2 to 26 weeks or 3 to 26 weeks.

In the methods of the invention, NALL may also be administered intermittently or on as needed basis.

The invention is also directed in part to a method of treating a neurodevelopmental disorder in a subject in need thereof comprising administering to the subject a therapeutically effective amount of N-acetyl-DL-leucine (NAL), or a pharmaceutically acceptable salt thereof. NAL contains N-acetyl-L-leucine (NALL), which has therapeutic efficacy for treatment of neurodevelopmental disorders. In some of the embodiments, N-acetyl-DL-leucine in NAL may potentiate therapeutic effects of N-acetyl-L-leucine in NAL. For example, N-acetyl-D-leucine (NADL) contained in NAL may minimize or slow down degradation of NALL prior to NALL being transported through the MCT1 receptor (e.g., by acting as a competitive inhibitor of the enzymes responsible for degradation of NALL). NAL may also be cheaper and easier to manufacture than NALL and, consequently, more readily available than NALL.

In the methods of the invention, the therapeutically effective amount of NAL, or a pharmaceutically acceptable salt thereof, that is administered per day will generally range from about 200 mg to about 10 grams. In some embodiments, from about 200 mg to about 5 grams, about 500 mg to about 4 grams or about 1000 mg to about 3 grams of NAL is administered to the subject per day.

NAL may be administered orally in a pharmaceutical composition consisting of NAL, or a pharmaceutically acceptable salt thereof, and pharmaceutically acceptable excipients. The pharmaceutical composition may, e.g., be a tablet, a capsule or a powder formulation (e.g., granules that could be sprinkled on food and/or dissolved in a liquid prior to administration). The pharmaceutical composition may also be in the form of a solution consisting of NAL, a solvent and optional pharmaceutically acceptable excipients, wherein NAL is completely dissolved in the solvent. The frequency of NAL administration may range from one to four times a day.

The invention is also directed in part to a method of treating SYNGAP1-Related Disorder in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating SYNGAP1-Related Disorder in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating SLC6A1-Related disorder in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating MED13L syndrome in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating CTNNB1 syndrome in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating DLG4-related synaptopathy in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating FOXG1 syndrome in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating Autism Spectrum Disorder in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating Attention-Deficit Disorder in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating intellectual disability in a subject in need thereof comprising orally administering to the subject from about 200 mg to about 10 grams of N-acetyl-DL-leucine (NAL), or a pharmaceutically acceptable salt thereof, per day. In some embodiments, from about 200 mg to about 5 grams, about 250 mg to about 5 grams or about 400 mg to about 3 grams of NAL is administered to the subject per day.

The invention is also directed in part to a method of treating a neurodevelopmental disorder in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating a developmental and epileptic encephalopathy in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating SYNGAP1-Related Disorder in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating SLC6A1-Related disorder in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating MED13L syndrome in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating CTNNB1 syndrome in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating DLG4-related synaptopathy in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating FOXG1 syndrome in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating KCNT1 epilepsy in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating Autism Spectrum Disorder in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating Attention-Deficit Disorder in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

The invention is also directed in part to a method of treating intellectual disability in a subject in need thereof comprising orally administering to the subject N-acetyl-DL-leucine (NAL), or a pharmaceutically acceptable salt thereof, at a dose of from about 10 mg/kg/day to about 600 mg/kg/day, from about 10 mg/kg/day to about 400 mg/kg/day or from about 20 mg/kg/day to about 400 mg/kg/day.

In the methods of the invention, NAL may be administered for as long as its therapeutic efficacy is maintained. In some of the embodiments, NAL is administered for 1 to 52 weeks, 2 to 26 weeks or 3 to 26 weeks.

In the methods of the invention, NAL may also be administered intermittently or on as needed basis.

In addition to the administration of a compound of Formula (I), Formula (II), Formula (III), or Formula (IV), including NALL or NAL, any one of the methods of the invention may further comprise a step of administering an additional active pharmaceutical ingredient to the subject.

The additional active pharmaceutical ingredient may be a small molecule or a biologic.

In certain embodiments, the additional active pharmaceutical ingredients may be selected from a group consisting of drugs affecting localized translation of RNA into protein (subcellular localization, which requires energy, tubulin dynamics, and other specialized cell cycle processes); drugs affecting glucose and energy usage; drugs affecting mitochondrial function, efficiency, inhibition, activation, balance changes, and other effects; drugs that increase, balance or regulate any process of autophagy or time in autophagy; precision medicines; drugs that decrease, regulate, or otherwise affect the expression of proinflammatory cytokines; drugs that increase, change, balance, or modulate the complex multi-region process of vestibular compensation; drugs that decrease or regulate or balance the tyrosine catabolic processes drugs; and combinations of any of the foregoing.

In certain embodiments, the additional active pharmaceutical ingredients may be selected from a group consisting of antidepressants, antipsychotics, benzodiazepines, antihypertensives, stimulant and non-stimulant ADD medications, antiepileptic medications, estrogens, anticholinergics, antimuscarinics, antispasmodics, antacids, steroids, muscle relaxants, beta-blockers, statins, gamma aminobutyric acid (GABA) analogues, acetylcysteine, cannabinoids, laxatives, stool softeners, bulking agents, antibiotics, antifungals, antivirals, probiotics, vitamins, and nutritional supplements.

In certain embodiments, the additional active pharmaceutical ingredient may be selected from a group consisting of benzodiazepines, serotonin reuptake inhibitors, antidepressants, antipsychotics, antiepileptics; amphetamines, gamma aminobutyric acid (GABA) analogues, statins, and pharmaceutically acceptable salts of any of the foregoing.

Antiepileptics that could be used in combination with compounds of Formula (I), Formula (II), Formula (III), or Formula (IV), including NALL and NAL, in the methods of the invention include, e.g., brivaracetam, carbamazepine, clonazepam, cenobamate, ethosuximide, gabapentin, phenobarbital, phenytoin, primidone, valproate, valproic acid, felbamate, brivaracetam, eslicarbazepine, ethosuximide, lamotrigine, lacosamide, levetiracetam, oxcarbazepine, perampanel, pregabalin, cannabidiol, clobazam, fenfluramine, perampanel, rufinamide, stiripentol, topiramate, tiagabine, vigabatrin, zonisamide, and pharmaceutically acceptable salts of any of the foregoing. In some of the embodiments the antiepileptic is selected from a group consisting of valproate, lamotrigine, topiramate, levetiracetam, zonisamide, gabapentin, ethosuximide, and pharmaceutically acceptable salts thereof.

Antiepileptics that could be used in combination with compounds of Formula (I), Formula (II), Formula (III), or Formula (IV), including NALL and NAL, in the methods of the invention include, e.g., aripiprazole, aripiprazole, asenapine, olanzapine, paliperidone, quetiapine, risperidone, risperidone, haloperidol, and pharmaceutically acceptable salts thereof.

Antidepressants that could be used in combination with compounds of Formula (I), Formula (II), Formula (III), or Formula (IV), including NALL and NAL, in the methods of the invention include, e.g., tricyclic antidepressants and selective serotonin reuptake inhibitors. The antidepressant may, e.g., be selected from a group consisting of protriptyline, nortriptyline, trazodone, sertraline, fluoxetine, escitalopram, citalopram, venlafaxine, and pharmaceutically acceptable salt thereof.

Benzodiazepines that could be used in combination with compounds of Formula (I), Formula (II), Formula (III), or Formula (IV), including NALL and NAL, in the methods of the invention include, e.g., clobazam, lorazepam, alprazolam, diazepam, and pharmaceutically acceptable salts thereof.

Antihypertensive that could be used in combination with compounds of Formula (I), Formula (II), Formula (III), or Formula (IV), including NALL and NAL, in the methods of the invention include, e.g., clonidine and pharmaceutically acceptable salts thereof.

Non-stimulant ADD medications that could be used in combination with compounds of Formula (I), Formula (II), Formula (III), or Formula (IV), including NALL and NAL, in the methods of the invention include, e.g., guanfacine and pharmaceutically acceptable salts thereof.

Stimulant ADD medications that could be used in combination with compounds of Formula (I), Formula (II), Formula (III), or Formula (IV), including NALL and NAL, in the methods of the invention include, e.g., lisdexamfetamine, methylphenidate, and pharmaceutically acceptable salts thereof.

Laxatives that could be used in combination with compounds of Formula (I), Formula (II), Formula (III), or Formula (IV), including NALL and NAL, in the methods of the invention include, e.g., bisacodyl, PolyEthyleneGlycol 3350, lactulose, and pharmaceutically acceptable salts thereof.

Stool softeners that could be used in combination with compounds of Formula (I), Formula (II), Formula (III), or Formula (IV), including NALL and NAL, in the methods of the invention include, e.g., docusate and pharmaceutically acceptable salts thereof.

Bulking agents that could be used in combination with compounds of Formula (I), Formula (II), Formula (III), or Formula (IV), including NALL and NAL, in the methods of the invention include, e.g., methylcellulose and *psyllium*.

Nutritional supplements that could be used in combination with compounds of Formula (I), Formula (II), Formula (III), or Formula (IV), including NALL and NAL, include, e.g., melatonin and pharmaceutically acceptable salts thereof.

Muscarinic agents that could be used in combination with compounds of Formula (I), Formula (II), Formula (III), or Formula (IV), including NALL and NAL, in the methods of the invention include, e.g., tridihexethyl chloride.

Gamma aminobutyric acid (GABA) analogues that could be used in combination with compounds of Formula (I), Formula (II), Formula (III), or Formula (IV), including NALL and NAL, in the methods of the invention include, e.g., alfadolone, gabapentin, and pharmaceutically acceptable salts thereof.

Statins that could be used in combination with compounds of Formula (I), Formula (II), Formula (III), or Formula (IV), including NALL and NAL, in the methods of the invention include, e.g., atorvastatin, rosuvastatin, simvastatin, pravastatin, lovastatin, fluvastatin, and pharmaceutical salts thereof.

In certain embodiments, the additional active pharmaceutical ingredient is selected from a group consisting of onfi, valproate, lamortagine, melatonin, butyrate, risperidone, sertraline, polyethylene glycol 3350, CBD, guanfacine, trazadone, clonidine, gabapentin, levitracetam, epidialex, bisacodyl, citalopram, clonazepam, MCT/C8 oil, methylphenidate, memantine, quetiapine, epidyolex, brivaracetam, midazolam, zonisade, and pharmaceutically acceptable salts thereof.

In certain embodiments, the combined administration of the compound of Formula (I), Formula (II), Formula (III), or Formula (IV), including NALL and NAL, together with the additional pharmaceutical ingredient provides a synergistic effect that allows for an improved therapeutic efficacy and/or administration of a lower dose of the compound of Formula (I), Formula (II), Formula (III), or Formula (IV) and/or the additional pharmaceutical ingredient that would normally be required to achieve an equivalent therapeutic effect.

In one embodiment, the compound of Formula (I), Formula (II), Formula (III), or Formula (IV), including NALL and NAL, is administered together with together with butyrate or a pharmaceutical acceptable salt thereof and provides a therapeutic effect that is synergistic.

The combined administration in accordance with the present invention may improve QOL of the patient and his or her caregivers, e.g., by reducing unwanted side effects and/or improved efficacy and/or simply by reducing the number of medicines that the patient needs to take.

In the methods of the invention, the additional active pharmaceutical ingredient may be administered either separately or together with the compound of Formula (I), Formula (II), Formula (III), or Formula (IV) via a route selected from the group consisting of orally, parenterally, sublingually, via suppository, nasally, topically, transdermally, intravenously, subcutaneously, intraperitoneally and via implant under the skin in the same or a different composition.

The invention is further directed to a pharmaceutical composition comprising a compound of Formula (I), Formula (II), Formula (III), or Formula (IV) and a pharmaceutically acceptable excipient, the pharmaceutical composition for use in the treatment of a neurodevelopmental disorder. Compounds of Formula (I) and Formula (II) encompass NALL.

The invention is further directed to a pharmaceutical composition comprising a compound of Formula (I), Formula (II), Formula (III), or Formula (IV) and a pharmaceutically acceptable excipient, the pharmaceutical composition for use in the treatment of SYNGAP1-Related Disorder.

The invention is further directed to a pharmaceutical composition comprising NALL and a pharmaceutically acceptable excipient, the pharmaceutical composition for use in the treatment of a neurodevelopmental disorder.

The invention is further directed to a pharmaceutical composition comprising NALL and a pharmaceutically acceptable excipient, the pharmaceutical composition for use in the treatment of a developmental and epileptic encephalopathy.

The invention is further directed to a pharmaceutical composition comprising NALL and a pharmaceutically acceptable excipient, the pharmaceutical composition for use in the treatment of SYNGAP1-Related Disorder.

The invention is further directed to a pharmaceutical composition comprising NALL and a pharmaceutically acceptable excipient, the pharmaceutical composition for use in the treatment of MED13L syndrome.

The invention is further directed to a pharmaceutical composition comprising NALL and a pharmaceutically acceptable excipient, the pharmaceutical composition for use in the treatment of CTNNB1 syndrome.

The invention is further directed to a pharmaceutical composition comprising NALL and a pharmaceutically acceptable excipient, the pharmaceutical composition for use in the treatment of DLG4-related synaptopathy.

The invention is further directed to a pharmaceutical composition comprising NALL and a pharmaceutically acceptable excipient, the pharmaceutical composition for use in the treatment of FOXG1 syndrome.

The invention is further directed to a pharmaceutical composition comprising NALL and a pharmaceutically acceptable excipient, the pharmaceutical composition for use in the treatment of SLC6A1-Related disorder.

The invention is further directed to a pharmaceutical composition comprising NALL and a pharmaceutically acceptable excipient, the pharmaceutical composition for use in the treatment of KCNT1 epilepsy.

The invention is further directed to a pharmaceutical composition comprising NALL and a pharmaceutically acceptable excipient, the pharmaceutical composition for use in the treatment of Autism Spectrum Disorder.

The invention is further directed to a pharmaceutical composition comprising NALL and a pharmaceutically acceptable excipient, the pharmaceutical composition for use in the treatment of Attention-Deficit Disorder (ADD).

The invention is further directed to a pharmaceutical composition comprising NALL and a pharmaceutically acceptable excipient, the pharmaceutical composition for use in the treatment of Intellectual Disability.

In addition to NALL and NAL, the pharmaceutical compositions of the invention may comprise one or more additional active pharmaceutical ingredient(s) as outlined above.

The invention is also directed in part to a *Drosophila melanogaster* (fruit fly) model of SYNGAP1. The model is based on eye-specific RNAi knockdown of SYNGAP1, which is called raskol gene in flies. RNAi knockdown of the raskol gene in the eye of *Drosophila* results in a smaller, degenerate eye (FIG. 1). In one embodiment, the model is used to screen drug that rescue the degenerate eye phenotype in *Drosophila melanogaster.*

Definitions

It is noted that in this disclosure and particularly in the claims and/or paragraphs, terms such as "comprises", "comprised", "comprising", and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

As used above, and throughout the specification, the following terms, unless otherwise indicated, shall be understood to have the following meanings:

The singular forms "a," "an," and "the" include plural referents unless the context clearly dictates otherwise. Thus, for example, reference to "a pathogen" includes reference to one or more of such materials and reference to "the test" refers to one or more of such processes.

The term "about" in the present specification means a value within 20% (±20%) of the value recited immediately after the term "about," including the value equal to the upper limit (i.e., +20%) and the value equal to the lower limit (i.e., −20%) of this range. For example, the phrase "about 100" encompasses any numeric value that is between 80 and 120, including 80 and 120.

The term "NAL" means acetyl-DL-leucine.

The term "NALL" means N-acetyl-L-leucine.

The symbol "D" means deuterium.

The terms "effective amount" or "therapeutically effective amount" are used interchangeably herein, and refer to an amount of a compound, formulation, material, or composition, as described herein effective to achieve a particular therapeutic result. Such results may include, but are not limited to, the treatment of a disease or condition, or one or more symptoms of a disease or condition, described herein as determined by any means suitable in the art.

The term "mutation" as used herein means a DNA variant that is classified as pathogenic, likely pathogenic or a variant of uncertain significance (VUS) with clinical features of the disease, as recognized in the art.

In the context of the present specification SYNGAP1 "pathogenic" variants include, e.g., c.333delA, c.339del, c.397_427dup31, c.410delT, c.411_418delAAAAAGCT, c.434_447dup14, c.535delG, c.557_567dup, c.654_655del, c.673delT, c.698_699dupGT, c.745del, c.768_770delCAGinsAA, c.781_784delGACA, c.828dup, c.857_864dupTGGATGAC, c.878delG, c.883_884delAC, c.883_884del, c.949delC, c.1022_1030delinsTA, c.1057_1072del, c.1127del, c.1139del, c.1142_1143insT, c.1154_1161del, c.1167_1168del, c.1167_1168delAG, c.1167delA, c.1167_1168del, c.1292del, c.1329_1333delCAAGG, c.1441_1444dup, c.1463delC, c.1685dupC, c.1744del, c.1792delC, c.1935dupT, c.2152delC, c.2152delC, c.2293delA, c.2350_2354dup, c.2354dupG, c.2438delT, c.2438delT, c.2438del, c.2516dup, c.2523_2524del, c.2561_2577del, c.2591_2592del, c.2701dup, c.2774del, c.2776_2777del, c.2843del, c.2916delT, c.2955_2958del, c.2970del, c.3167_3188dup, c.3179dup, c.3186_3199del14insAGG, c.3227delT, c.3233_3236delTCAG, c.3233_3236delTCAG, c.3233_3236del, c.3273_3274del, c.3295delT, c.3303del, c.3416dupA, c.3642delG, c.3665_3669dupGGCTG, c.1760_1792del33, c.190-15_206delins28, c.190-2A>G, c.762+1G>T, c.1676+1G>T, c.1913+2T>G, c.1913+1G>A, c.3583-6G>A, c.3583-9G>A, c.484C>T, c.812C>A, c.980T>C, c.1084T>C, c.1685C>T, c.388C>T, c.403C>T, c.427C>T, c.490C>T, c.843C>A, c.937G>T, c.1089C>A, c.1166C>A, c.1284T>A, c.1507C>T, c.1735C>T, c.1744G>T, c.1861C>T, c.2059C>T, c.2104C>T, c.2197C>T, c.2266C>T, c.2450C>G, c.2494C>T, c.2755C>T, c.2899C>T, c.2946T>A, c.3124C>T, c.3190C>T, c.3277C>T, c.3316C>T, c.3370G>T, c.3452_3453del, c.3553A>T, c.3706C>T, and c.3718C>T.

In the context of the present specification SYNGAP1 "likely pathogenic" variants include, e.g., c.333delA, c.404_411delGACGGCTAinsT, c.838dup, c.3384dup, Gain (Exon 3), c.704_707delinsTTTT, c.388-3C>G, c.1532-1G>C, c.3583-9G>A, c.3583-9G>A, c.3583-9G>A, c.3795-1G>C, c.662A>T, c.851T>C, c.968T>A, c.1030G>A, c.1292T>C, c.1394T>C, c.1403T>A, c.1706T>C, c.1714T>C, c.1797C>G, c.1802C>A, c.1847A>G, c.1889T>A, c.1898T>C, c.1946T>G, c.1958T>C, c.1988T>C, c.922C>T, c.984C>G, and c.3534C>A.

In the context of the present specification SYNGAP1 "variants of uncertain Significance" include, e.g., c.3653A>T, c.28C>T, c.250C>G, c.971G>C, c.1715G>C, c.2003C>T, c.2305C>G, c.2693C>G, c.3345_3353dupTGGGGGCAG, c.3380G>C, c.4006G>A, and Gain (Entire coding sequence).

The term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to a subject. Multiple techniques of administering a compound exist in the art including, but not limited to oral and parenteral (e.g., intravenous) administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "subject" as used herein means "a human".

The term "treat" or "treating", as used herein, includes but is not limited to, alleviation or amelioration of one or more symptoms or conditions; diminishment of extent of disease, disorder, or condition; stabilized (i.e., not worsening) state of disease, disorder, or condition, or improvement in Quality of Life for the patient, family and caregivers.

The term "Quality of Life" (QOL), as used herein, refers to a measure in one or more symptoms that make a meaningful impact on the ease, comfort, happiness, or abilities of the patient, especially as they impact both the patient, the family, and the primary caregivers. Determination of QOL measures incorporates the values and the lived experience of the family, such that some symptoms, e.g. sleep or safety, may be valued above other symptoms, e.g. seizures. QOL is rated by each individual and will depend on the medical and practical specifics of each situation, along with values. The determination of changes in the Quality of Life incorporates individual choice.

The term Developmental and Epileptic Encephalopathies (DEEs) describes any of at least 825 genetic disorders with neurodevelopmental and epileptic symptoms.

As used herein, "alleviate" is used interchangeably with the term "treat." Treating a disease, disorder or condition may or may not include complete eradication or elimination of the symptom.

The term "salt" means a compound that results from replacement of part or all of the acid hydrogen of an acid by a metal or a radical acting like a metal: an ionic or electrovalent crystalline compound.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, or combinations of each.

The term "precision medicine" is used herein to describe a treatment that utilizes gene sequence information of the target in order to engineer, construct or build the medicine.

The term "active pharmaceutical ingredient" is a component of the pharmaceutical composition or dosage form that provides a therapeutic effect. Active pharmaceutical ingredients encompass drugs approved by the US FDA and drugs approved by European Medicines Agency (EMA) for use in humans.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

BRIEF DESCRIPTION OF THE DRAWINGS

FIG. 9 summarizes patient characteristics, medications and responses to acetyl-DL-leucine of Example 3.

FIG. 25 summarizes results of Example 20.

FIG. 42C depicts mechanism of NALL effect determined by RNAseq in Example 38. Enzymes TAT, HPD, FAA highlight the differences in RNA expression in the presence of NALL treatment; molecules are all associated with the tyrosine catabolic process.

Figure 1:
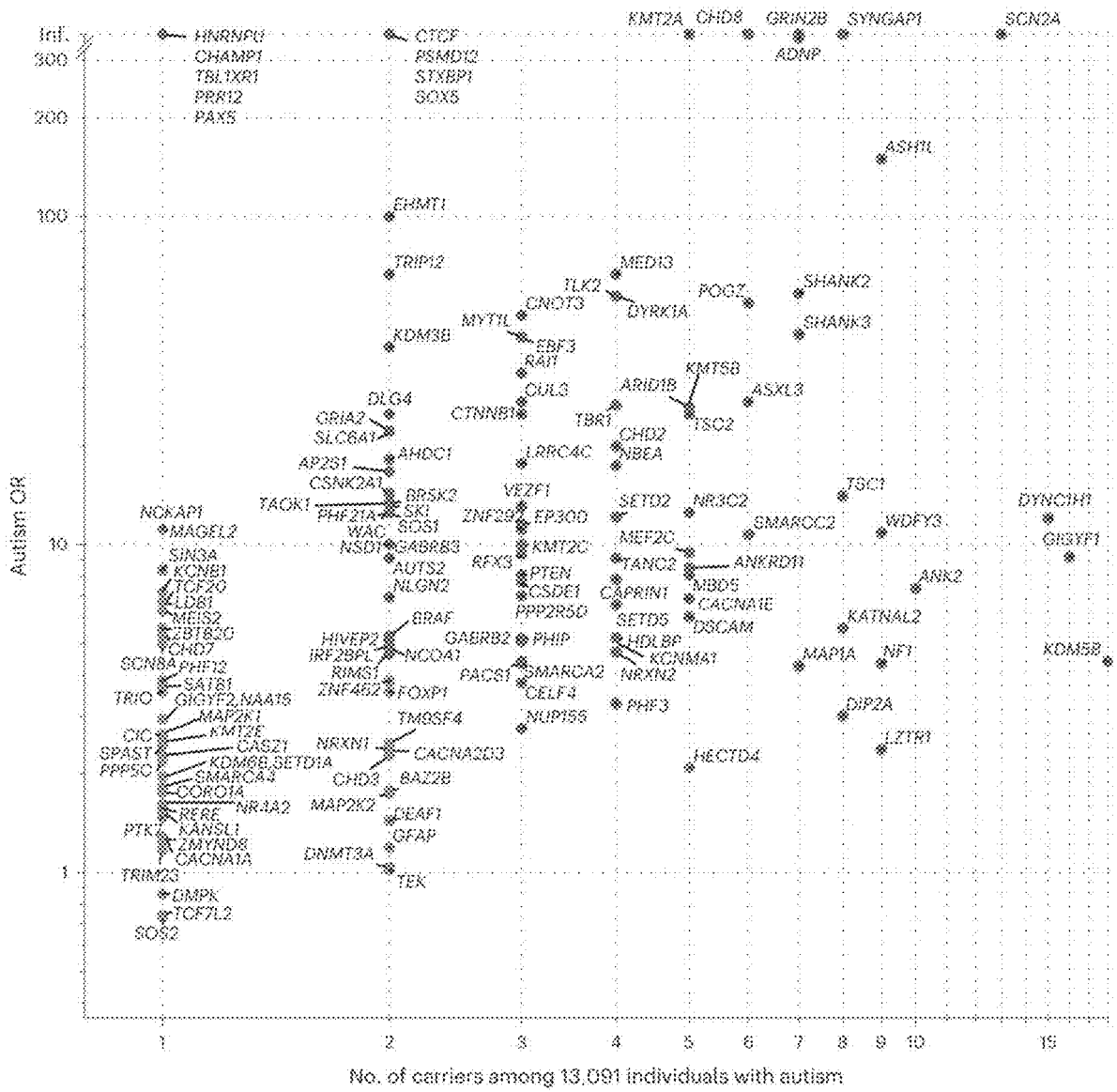
FIG. 1 is a graph of gene-level autism odds ratio (OR) for autism associated genes. Number of genetic carriers among individuals with autism and autism OR, which is the enrichment of loss of function variants among individuals with autism compared to undiagnosed individuals, are shown. Genes with autism ORs significantly higher than expected by chance are shown in in the same color/shade as SYN-GAP1. Genes associated with 5 of the 6 neurodevelopmental disorders are associated with increased autism OR. Modified from Rolland, et al, Phenotypic effects of genetic variants associated with autism. Nat. Med. 29, 1671-1680 (2023).

These drawings are provided to illustrate various aspects of the invention and are not intended to be limiting of the scope in terms of dimensions, materials, configurations, arrangements or proportions unless otherwise limited by the claims.

DETAILED DESCRIPTION

Over 1,500 genes have been associated with NDDs. These genes are involved in various signaling pathways and genetic mechanisms that contribute to the development and function of the nervous system.

The genes associated with NDDs include, e.g., SYNGAP1, SLC6A1, MED13L, CTNNBI, DLG4, KCNT1, FOXG1, and genes associated with other developmental and epileptic encephalopathies. The gene function, clinical features and prevalence of some of the NDDs associated with these genes are shown in Table 1.

TABLE 1

| Gene (disorder) | Prevalence | Gene Description and Function | Clinical Features |
| --- | --- | --- | --- |
| SYNGAP1 | 1530 known 1-2 per 100,000 individuals | The SYNGAP1 gene encodes synaptic Ras GTPase-activating protein 1 (SynGAP), which is essential for normal brain function and development. SynGAP is involved in the regulation of synaptic function and plasticity. It plays a critical role in the maturation and function of dendritic spines in neurons. SynGAP1 function is crucial for learning and memory. | ASD; ID; Developmental delays in motor and language skills; Behavioral issues; Sensory processing deficits; Movement disorders and hypotonia; Seizures of various types |

TABLE 1-continued

| Gene (disorder) | Prevalence | Gene Description and Function | Clinical Features |
|---|---|---|---|
| SLC6A1 | 204 known ~2.6 per 100,000 births | The SLC6Al gene encodes the GABA transporter protein type 1 (GAT1), which is responsible for the reuptake of GABA, the primary inhibitory neurotransmitter in the brain, from the synaptic cleft back into presynaptic neurons and glia. GAT1 terminates the action of GABA by its high-affinity sodium-dependent reuptake into presynaptic terminals, thus maintaining inhibitory tone in the central nervous system. This process is crucial for regulating neuronal excitability and preventing seizures. | ASD; ID; Developmental delays; Behavioral issues; Speech and language impairment, Early onset seizures of various type |
| MED13L | ~100 known | The MED13L gene encodes for a subunit of the Mediator complex, a large complex of proteins that functions as a transcriptional coactivator for most RNA polymerase II-transcribed genes. This complex is crucial for the early development of the heart and brain. | ASD; ID; Developmental delays in motor and language skills; Distinct facial features; Congenital heart defects; Seizures |
| DLG4 | <100 known | The DLG4 gene, also known as PSD-95 or SAP-90, encodes the discs large MAGUK scaffold protein 4, which is a postsynaptic scaffolding protein. This protein plays a critical role in synaptic plasticity, which is crucial for learning and memory. It helps organize synaptic signaling complexes at neuronal synapses, ensuring proper synaptic function and development. | ASD; ID; Developmental delays; Behavioral issues; Hypotonia, Sleep disturbances, GI difficulties; Seizures |
| CTNNB1 | ~430 known | The CTNNB 1 gene encodes the beta-catenin protein, which is integral to the Wnt signaling pathway. Beta-catenin plays a critical role in cell adhesion and gene transcription regulation, and it is part of the protein complexes that form adherens junctions necessary for maintaining epithelial cell layers. | ASD; ID; Developmental delays; Behavioral issues; Speech delays and language disorders; Abnormal muscle tone; Vision impairments; Distinct facial features; Feeding difficulties and growth abnormalities |
| KCNT1 | 493 known | The KCNT1 gene encodes a sodium-activated potassium channel in brain nerve cells. Mutations in KCNT1 cause seizures and developmental delays in children. Seizures can start in infancy and be difficult to control with medication. They can include focal stiffening, shaking, or epileptic spasms. Children may not be able to walk or talk. Children may have poor muscle tone (hypotonia), dystonia, choreoathetosis, or dyskinesia. Children may also have microcephaly, autonomic instability, abnormal heart rhythms, and abnormal blood vessels in the lungs. | ID; epilepsy, motor difficulties, speech and language disorder; cardiovascular abnormalities; increased risk of early death |
| FOXG1 | ~1000 known 3.33 per individuals | The FOXG1 gene encodes the forkhead box protein G1, a transcription factor crucial for brain development. This protein regulates the activity of other genes, particularly during the development of the telencephalon, which eventually forms the cerebrum. Mutations or deletions in this gene can disrupt normal brain development, leading to significant developmental issues and structural brain abnormalities. | ASD; ID; Neurodevelopmental delays; Behavioral issues; Motor skill and visual impairments: Speech and language delays; Physical symptoms such as scoliosis, hypotonia; GI issues; Structural brain abnormalities; Seizures |

Genes responsible for 5 of these 6 NDDs have been shown to be associated with development of ASD. Many more monogenic NDDs associated with ASD are shown in FIG. 1 (same color and shade as SYNGAP1).

NDDs are associated with several imbalances in the brain, including decreased pH and increased lactate levels, impaired removal of cellular waste, and altered energy use. Acetyl-leucine (e.g., NALL) may help correct these imbalances in the following ways.

N-acetyl-D-Leucine and N-acetyl-L-Leucine have the same chemical components but differ in the direction of a chemical bond. The carbon-nitrogen bond is shown as a dashed line for N-acetyl-D-leucine, indicating an inward orientation (heading through the page away from the reader), while the same bond for N-acetyl-L-leucine is shown as a filled triangle, indicating an outward orientation (coming out of the page toward the reader).

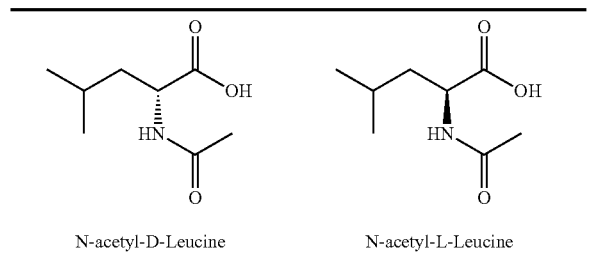

N-acetyl-D-Leucine     N-acetyl-L-Leucine

Figure 2:
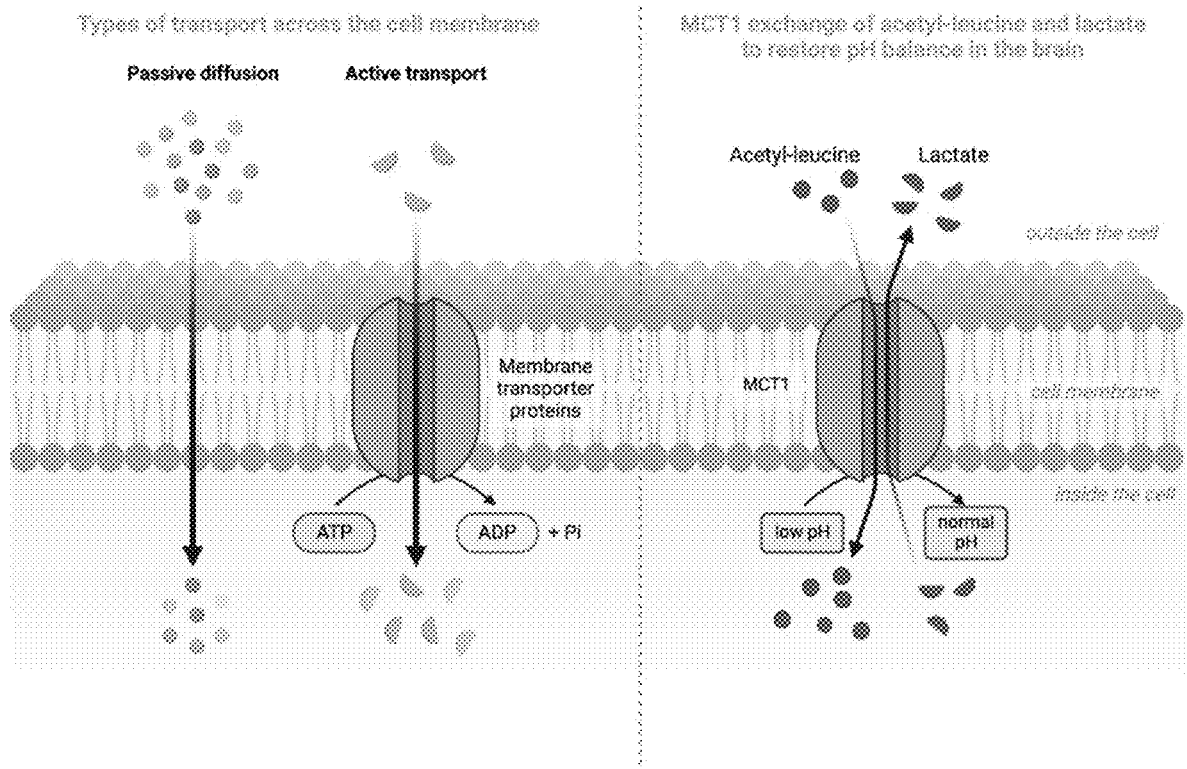
FIG. 2 shows transport of molecules across the cell membrane. Left) Small, uncharged molecules can pass directly through the cell membrane by passive diffusion. "Acetyl-leucine" in FIG. 2 is meant to represent "N-acetyl-L-leucine". Large or charged molecules must be transported by a membrane transporter protein in a process that requires energy (ATP). Right) The monocarboxylate transporter type 1 (MCT1) actively transports molecules across the cell membrane using an exchange mechanism, one molecule goes into the cell and another molecule goes out of the cell. MCT1 transports N-acetyl-L-leucine into the cell and transports lactate out of the cell. Many neurological conditions are associated with a low pH in the brain. When N-acetyl-L-leucine (negatively charged at neutral pH) and lactate (positively charged at neutral pH) are exchanged, the imbalanced pH in the neurons is restored.

L-leucine is a charged molecule at all physiologic pH ranges and, therefore, requires active transport across cell membranes. Active transport occurs when a transporter protein in the cell membrane binds to a target molecule, in this case L-leucine, and moves it from one side of the cell membrane to the other (FIG. 2, left). The L-type amino Acid Transporter (LAT1) is known to transport L-leucine and other large essential amino acids into cells.

While L-leucine is a natural and common amino acid, the chemical modification of L-leucine to make N-acetyl-L-leucine changes its properties and biological functions. Acetylation of L-leucine into N-acetyl-L-leucine allows N-acetyl-L-leucine to enter neurons and other cells more efficiently and by a different route. N-acetyl-L-leucine is uncharged at low pH and can enter cells through passive diffusion in the stomach. Passive diffusion occurs when a molecule can enter a cell directly, without a transporter protein. At higher pH ranges, N-acetyl-L-leucine enters cells through active transport.

N-acetyl-L-leucine neither binds nor blocks LAT1. Instead, N-acetyl-L-leucine has been shown to be transported by the organic anion transporters, OAT1 and OAT3, and the monocarboxylate transporter type 1 (MCT1). MCT1 transports several key monocarboxylates across cell membranes, including lactate, pyruvate, ketone bodies and acetate. A monocarboxylate is a type of organic molecule that contains one carboxylic acid group (—COOH) in its structure.

MCT1 can transport monocarboxylates in two different ways. It can function through a proton-linked cotransport mechanism, in which one monocarboxylate and one proton are transported across the membrane in the same direction. This type of transport can occur as a substrate influx into the cell or efflux out of the cell, depending on the substrate concentrations and pH gradients across the plasma membrane. MCT1 can also function as a bidirectional exchanger, by exchanging one substrate for another across the plasma membrane without the movement of a proton. In this way, MCT1 can function like a revolving door, as it lets one molecule into the cell it also lets one molecule out of the cell. MCTs are ubiquitously distributed in the body. MCT1 is notably at high concentrations in muscle tissue, brain, red blood cells, liver, kidney, intestinal epithelium and the retina. Additionally, MCT1 is expressed at the blood brain barrier, in the endothelial cells of the cerebral blood vessels.

MCT1 is a known transporter of several drugs, including salicylate and valproic acid, which are monocarboxylate derivatives.

The exchange mode of MCT1 transport could be one mechanism in which n-acetyl-L-leucine exerts its therapeutic effects. FIG. 2 shows that, as N-acetyl-L-leucine is transported into the cell, the metabolic monocarboxylate end-product lactate could be transported out (FIG. 2, right).

Accumulation or increased levels of lactate in the brain have been reported for several neurological disorders, including Parkinson's, Alzheimer's, Huntington's, major depressive disorder, anxiety, bipolar disorder, schizophrenia, as well as in stroke and traumatic brain injury. For several of these conditions, accumulation of lactate lowers the brain pH and subsequently affects the release of neurotransmitters and neuronal activity. Cells with elevated lactate levels could enhance the uptake of N-acetyl-L-leucine through an exchange mechanism; this process would allow for increased delivery of the drug to cells experiencing metabolic dysfunction. Therefore, as MCT1 exchanges N-acetyl-L-leucine and lactate it may help to rebalance the pH of the brain, which may result in an alleviation of one or more symptoms of a neurodevelopmental disorder.

Figure 3:
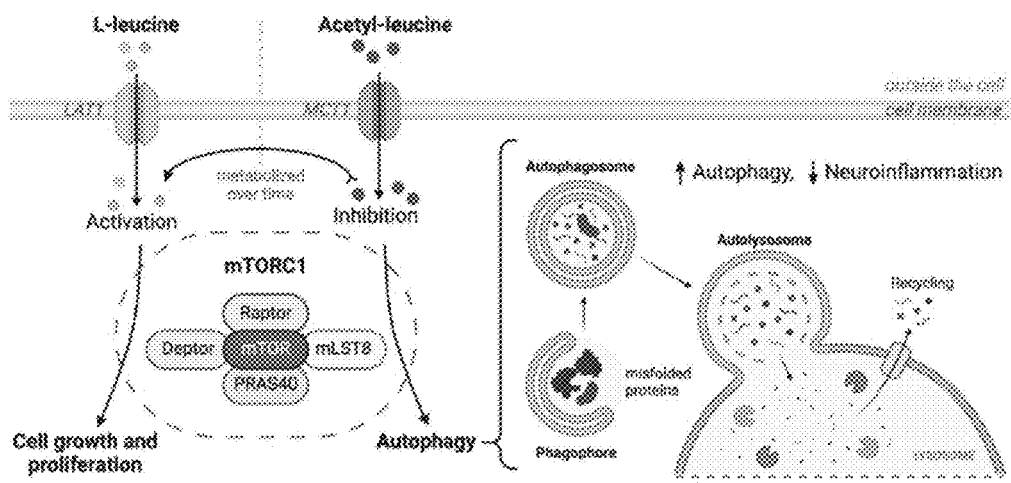
FIG. 3 shows regulation of the mechanistic Target of Rapamycin Complex 1 (mTORC1) by L-leucine and N-acetyl-L-leucine, which is shown as "acetyl-leucine" in FIG. 3. Left) L-leucine activates mTORC1, resulting in cell growth. N-Acetyl-L-leucine inhibits mTORC1, resulting in autophagy. The balance of intracellular L-leucine and N-acetyl-L-leucine regulate mTORC1 activity. Metabolism of N-acetyl-L-leucine to leucine eventually curtails mTORC1 inhibition in favor of cell growth and proliferation. Right) Autophagy is a process by which misfolded proteins and other unnecessary components of the cell are degraded and recycled. Misfolded proteins are engulfed by a phagophore which develops into an autophagosome then fuses with the lysosome where the contents are broken down for reuse. Increased autophagy results in reduced inflammation of the brain.

L-leucine activates mTORC1 (FIG. 3). The metabolic derivative of leucine, known as acetyl-coenzyme A (Ac-CoA), has been shown to positively regulate mTORC1 by facilitating the acetylation of an important protein, Raptor. Conversely, N-acetyl-L-leucine has been shown to inhibit or negatively regulate mTORC1 in a mechanism similar to that of rapamycin. The concentrations of these two compounds in the cell therefore direct the cell to focus on either anabolic (building up complex molecules and tissues) or catabolic (breaking down and recycling damaged molecules) processes. The proper balance of catabolic and anabolic processes is important for health, so chronic activation or inhibition of mTORC1 can lead to disease.

Once inside the cell, N-acetyl-L-leucine is metabolized to L-leucine. Therefore, it is possible that N-acetyl-L-leucine initially inhibits mTORC1, promoting autophagy and allowing neurons and other cells to eliminate damaged or misfolded proteins, in a process that is self-limited by its metabolic product, leucine.

Dysregulation of autophagy has been shown to be associated with epilepsy.

N-acetyl-L-leucine has been shown to upregulate autophagy. In mice with controlled cortical impact induced experimental traumatic brain injury (TBI), N-acetyl-L-leucine treatment led to an increase in autophagy. This was demonstrated as a reduction in accumulation of autophagosome markers in cortical tissue of treated mice as compared to controls. Increase in autophagy was associated with a reduction in neuronal death, reduced expression of proinflammatory cytokines, and ultimately a significant improvement in motor and cognitive outcomes. Therefore, N-acetyl-L-leucine inhibition of the mTORC1 pathway may increase autophagy, resulting in removal of misfolded or damaged proteins and reduced neuroinflammation.

Leucine has many important functions in cells, including metabolic and regulatory roles in neurons. Leucine can also function as an alternative energy source and has been shown to improve glucose metabolism. Altered or dysfunctional energy metabolism in the brain have been shown for varying neurological conditions, including Alzheimer's disease, stroke, traumatic brain injury and epilepsy. The metabolism of N-acetyl-L-leucine into leucine inside cells and neurons L-Leucine for modulation of metabolism and may overcome or alleviate neurological impairments.

Figure 4:
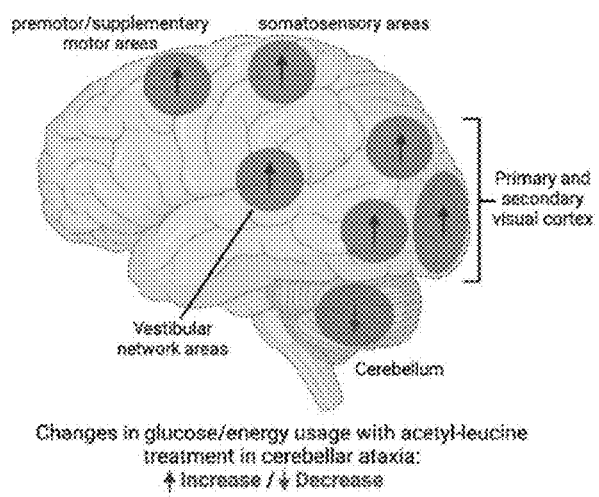
FIG. 4 shows N-acetyl-L-leucine treatment modulates glucose and energy usage in the brain. N-Acetyl-L-leucine treatment in patients with cerebellar ataxia resulted in modified glucose metabolism in the brain. Increases in glucose metabolism were observed in visual and vestibular cortices. Decreased glucose metabolism was observed in the cerebellum. This indicates increased sensory functioning and enhanced compensatory processes. Reconstructed from Becker-Bense, et al, 2023.

In patients with cerebellar ataxia, a disorder that manifests as a lack of muscle control during voluntary movements, acetyl-leucine has been shown to impact the central vestibular compensatory processing of the brain. Vestibular compensation is a complex process by which the brain adapts to changes in the inner ear following vestibular injury or dysfunction, aiming to restore balance and normal function. Whole-brain imaging studies with patients with cerebellar ataxia have shown that acetyl-leucine treatment activates or increases glucose usage in the somatosensory (postcentral), visual (temporo-parietal-occipital cortex, primary and secondary visual areas, V5, and the precuneus), and secondary vestibular (middle/superior temporal gyrus, anterior insula). Conversely, acetyl-leucine treatment was shown to deactivate or reduce glucose usage in the cerebellum (FIG. 4). However, not all individuals responded to acetyl-leucine treatment, with 12 out of 20 individuals (60%) demonstrating significant improvements in ataxia, which correlated with altered glucose metabolism patterns in the brain.

While acetyl-leucine has been shown to accelerate vestibular compensation in animals following unilateral labyrinthectomy, a surgical procedure for the management of poorly compensated unilateral peripheral vestibular dysfunction, it has shown only minor effects on normal vestibular function. Intracellular recordings from vestibular neurons showed the response to acetyl-leucine was dependent on the cell's resting membrane potential. Acetyl-leucine has been shown to act on abnormally hyperpolarized and/or depolarized vestibular neurons by restoring membrane potential to normal values. Therefore, N-acetyl-L-leucine may have utility in balancing energy and neuronal function within the brain.

Pharmaceutical Compositions

Pharmaceutical compositions that are useful in the methods of invention may be prepared, packaged, or sold in formulations suitable for oral, parenteral, topical, buccal, or another route of administration. Other contemplated formulations include, e.g., nanoparticles and liposomal preparations, exosomal (including targeted exosomal) preparations, orally disintegrable preparations (e.g., tablets and films), and formulations that have an appearance of or could be added to candies, cookies, cereals, and snacks.

In certain embodiments, the pharmaceutical compositions are provided in the form, shape, size, and dose to be easily hidden or added to a food liked by the individual being treated (e.g., a sandwich cookie filling or a Nutella cookie).

The pharmaceutical compositions of the invention comprise or consist of a compound of Formula (I), Formula (II), Formula (III), or Formula (IV) and one or more pharmaceutically acceptable excipients.

A pharmaceutical composition of the invention may be prepared, packaged, or sold in bulk, as a single unit dose (e.g., a packet), or as a plurality of single unit doses of, e.g., NAL, NALL or pharmaceutically acceptable salts thereof. As used herein, a "unit dose" is discrete amount of NALL or NAL. The amount of NALL or NAL is generally equal to the dosage of NALL or NAL that would be administered to a subject or a convenient fraction of such a dosage such as, for example, one-half or one-third of such a dosage.

In certain embodiments, the compositions of the invention may consist of (i) NALL or a pharmaceutically acceptable salt thereof, (ii) NALL, or a pharmaceutically acceptable salt thereof, and one or more pharmaceutically acceptable excipient(s), (iii) NAL, or a pharmaceutically acceptable salts thereof, or (IV) NAL, or a pharmaceutically acceptable salt thereof, and one or more pharmaceutically acceptable excipient(s), and be in a form suitable for administration to a subject (e.g., in a form of a tablet, a capsule or a solution). The compositions of the invention may also comprise NALL or NAL, or a pharmaceutically acceptable salt of NALL or NAL, and at least one additional active ingredient.

In one embodiment, the compositions of the invention may be formulated using one or more pharmaceutically acceptable carriers. Pharmaceutically acceptable carriers that are useful, include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), herein incorporated by reference. The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, compositions of the invention may contain NALL or NAL in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations containing the compositions of the invention may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. In one embodiment, a preservative comprises a combination of about 0.5% to 2.0% benzyl alcohol and 0.05% to 0.5% sorbic acid.

The composition may include an antioxidant and a chelating agent that inhibits the degradation of the compound. Preferred antioxidants for some compounds are BHT, BHA, alpha-tocopherol, and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions of the invention may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing, or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredients in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Controlled- or sustained-release formulations of a composition of the invention may be made using conventional technology, in addition to the disclosure set forth elsewhere herein. In some cases, the dosage forms to be used can be provided as slow or controlled release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Routes of administration of any of the compositions of the invention include oral, nasal, rectal, parenteral, sublingual, transdermal, transmucosal (e.g., sublingual, lingual, (trans) buccal, (intra)nasal, and (trans)rectal, intrapulmonary, intraduodenal, intragastric, intrathecal, subcutaneous, intramuscular, intradermal, intra-arterial, intravenous, intrabronchial, inhalation, and topical administration.

For oral administration, particularly suitable are tablets, dragees, liquids, powders (e.g., granules), drops, solutions, suspensions, emulsions, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more inert, non-toxic pharmaceutically excipients. Such excipients include, for example an inert diluent such as lactose; granulating and disintegrating agents such as cornstarch; binding agents such as starch; and lubricating agents such as magnesium stearate. The oral compositions of the invention in the form of tablets or capsules prepared by conventional means with pharmaceutically acceptable excipients such as binding agents; fillers; lubricants; disintegrates; or wetting agents.

Tablets may be non-coated, or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically controlled release tablets. Tablets may further comprise a sweetening agent, a flavoring agent, a coloring agent, a preservative, or some combination of these in order to provide for pharmaceutically elegant and palatable preparation. For oral administration, if desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Hard capsules comprising the active ingredients may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid preparation for oral administration may be in the form of solutions, syrups, or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters, or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

A pharmaceutical composition of the invention may be prepared, packaged, or sold in a formulation suitable for oral administration.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications.

Dosage Forms

The compositions of the invention may be formulated into a pharmaceutically acceptable oral dosage form. Oral dosage forms may include but are not limited to, oral solid dosage forms and oral liquid dosage forms. Oral solid dosage forms may include but are not limited to, tablets, capsules, caplets, powders, pellets, multiparticulates, beads, spheres and/or any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof as outlined in detail above. Each of these excipient(s) may, e.g., comprise from about 0.1% to about 99.9%, from about 0.5% to about 95%, from about 1% to about 95%, from about 2% to about 95%, from about 3% to about 95%, or from about 5% to about 95% of the formulation by weight.

The compositions of the invention may also be formulated into a pharmaceutically acceptable parenteral dosage form.

The compositions of the invention may also be formulated into a pharmaceutically acceptable transdermal dosage form.

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Administration

The compounds and compositions of the present invention may be used as therapy to treat neurodevelopmental disorders. Neurodevelopmental disorders amenable to treatment by the methods of the present invention include, e.g., SYNGAP1-Related Disorder, SLC6A1-Related disorder, MED13L syndrome, CTNNB1 syndrome, DLG4-related synaptopathy, KCNT1 epilepsy, and FOXG1 syndrome, Autism Spectrum Disorder (ASD), Attention-Deficit Disorder (ADD), Intellectual Disability (ID), and other developmental and epileptic encephalopathies.

The compounds and compositions of the present invention may be administered by any pharmaceutically effective route. For example, the compounds and compositions of the invention can be administered in liquid, tablet, parenteral, transrectal, transdermal or in any other form of administration or formulation suitable in order to achieve a therapeutic effect. Such formulations may contain additional fillers, carriers, excipient or excipients, inert or not, as outlined above or known to those skilled in the art of pharmaceutical preparations, in order to provide appropriate dose, volume, and/or facilitate absorption of the active drug(s).

Subjects amenable to treatment include individuals showing symptoms of neurodevelopmental disorders and individuals having a mutation in SYNGAP1, SLC6A1, MED13L, CTNNB1, DLG4, KCNT1, or FOXG1 gene associated with clinical manifestations of a neurodevelopmental disorder but not showing symptoms. Thus, in certain embodiments, the treatment includes prophylactic administration of the compounds of the invention to an individual not exhibiting symptoms of neurodevelopmental disorders, e.g., in an effort to prevent and/or delay appearance of symptoms of a neurodevelopmental disorder in the subject or to prolong symptom-free period.

Treatment typically entails multiple dosages over a period of time. The period of time may, e.g., be from 1 week to 52 weeks, from 1 week to 26 weeks, from 2 weeks to 26 weeks, or from 3 weeks to 26 weeks. The treatment may also continue for as long as a therapeutic benefit is observed. Treatment may also be provided on an intermittent or on as needed basis.

Therapeutically effective doses of the compositions of the present invention, for the treatment of the above-described conditions may vary depending upon many different factors, including means of administration, target site, physiological state of the subject, other medications administered, but would generally range between about 5 mg to 10 grams. In view of the information provided herein, therapeutically effective amounts or doses can be determined and optimized using standard clinical techniques by a person of ordinary skill in the art.

Example 1

*Drosophila* Model of SYNGAP1-Related Disorder

*Drosophila* (fruit fly) model of SYNGAP1 was generated. This model is partial loss of function of SYNGAP1, similar to what is observed in humans.

Figure 5:
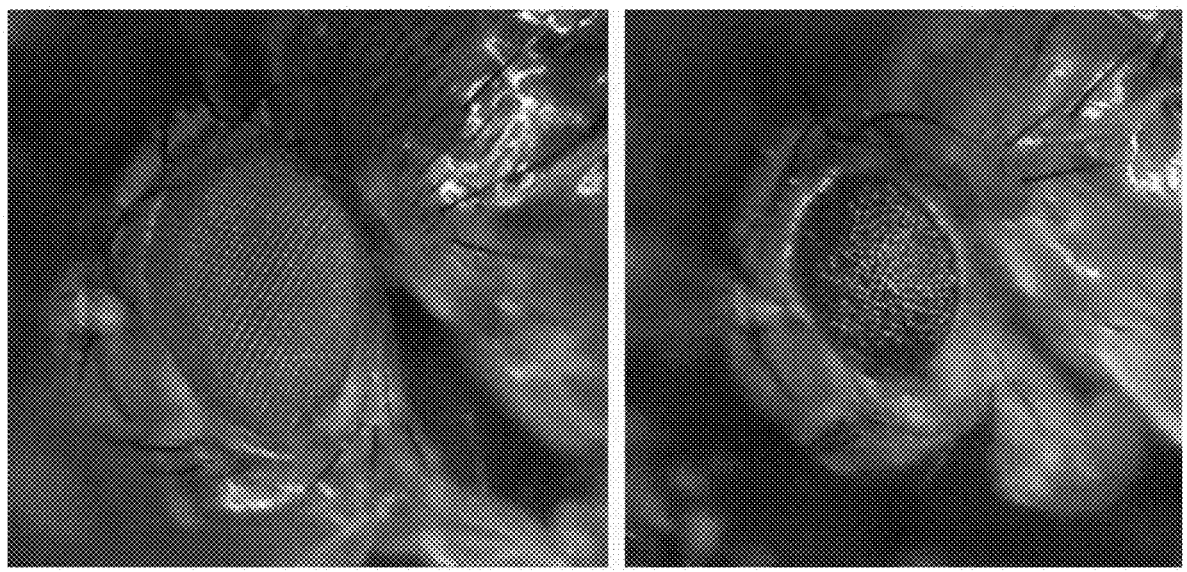
FIG. 5 is a graph of effects of SYNGAP1 knockdown on eye size in *Drosophila* in accordance with one example.

To generate the model, fruit flies were engineered to eliminate SYNGAP1 gene expression in the eye. In flies, the gene is called raskol but herein referred to as SYNGAP1 for clarity. Eye-specific knockdown of SYNGAP1 using RNAi was used. RNAi knockdown of SYNGAP in the eye results in a smaller, disorganized and degenerate eye (FIG. 5).

The model allows for ascertaining therapeutic efficacy of a compound. The efficacy is evidenced by restoration of normal eye appearance upon treatment with the compound.

In addition to the degenerate eye phenotype, raskol *Drosophila* are prone to induced seizures, as compared to wild type *Drosophila*.

Example 2

Drug Screen

Figure 6:
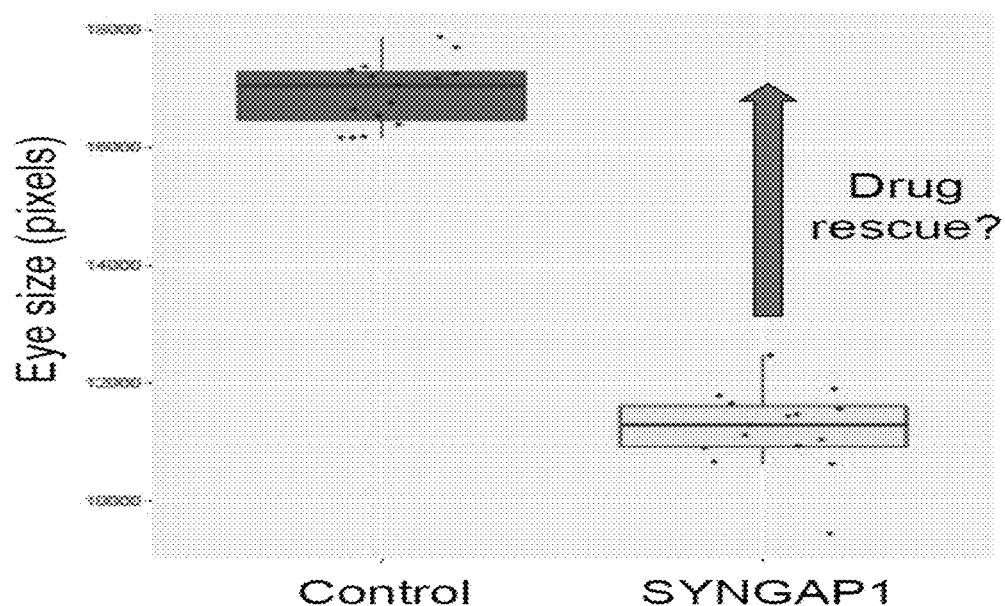
FIG. 6 is a graph of the drug screen overview in accordance with another example.

Using *Drosophila* model of SYNGAP1, a drug screen of over 1520 drugs in the Prestwick Chemical Library was performed. The drug screen was based on the rescue of this degenerate eye phenotype (FIG. 6).

A prioritized list of top hits was developed to further validate. Priority was place on actionable, safe, and biologically relevant drugs. To validate a top hit, the effect of each drug was tested over three doses. Three concentrations (1, 5, and 25 uM) were compared to a no drug control.

Figure 7:
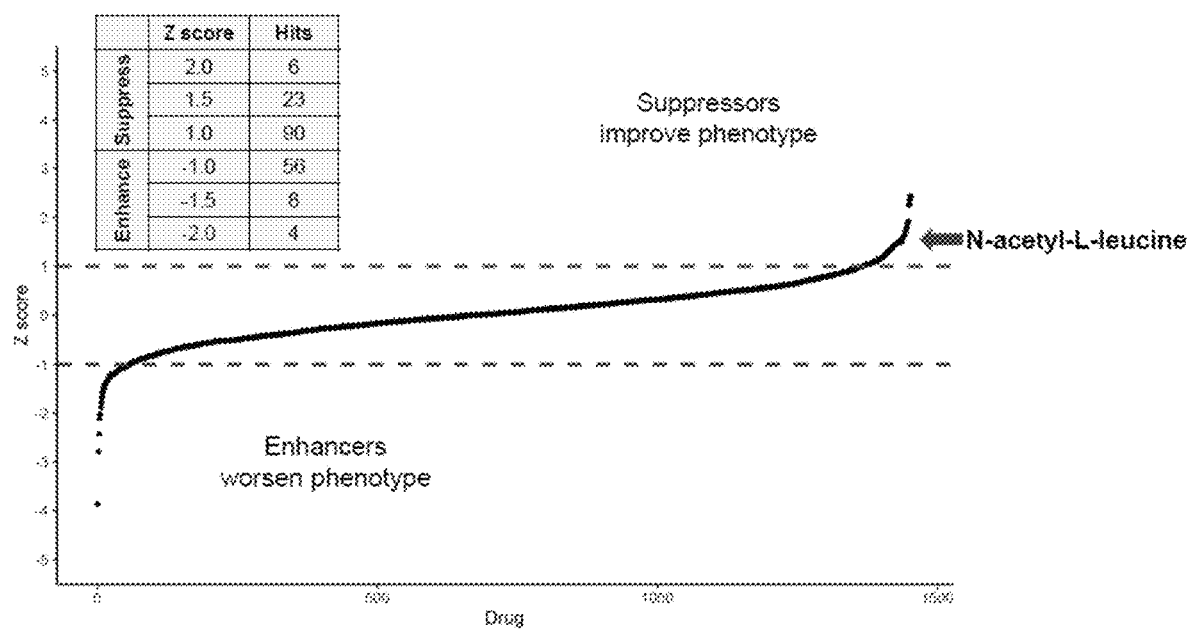
FIG. 7 is a graph of the Z-score of chemical effects on raskol *Drosophila* eye phenotype. Z scores >1 indicated improved phenotype; Z scores <1 indicated worsened phenotype. The arrow indicates the Z-score positioning of N-Acetyl-L-leucine (NALL).

N-acetyl-L-leucine (NALL) was among the top hits (Z=1.35) and showed a strong validation (FIG. 7). Across all three tested concentrations, NALL consistently produced a larger, more organized, less degenerate eye in the SYNGAP1 model. Together, these data indicate that NALL has utility as a therapeutic for SYNGAP1-related disorder.

Example 3

Validation of Efficacy in Humans

Thirty patients with 4 different genetic conditions used acetyl-DL-leucine and self-reported outcomes using standardized caregiver reported outcome forms. Patients' genetic conditions included SYNGAP1 (N=21), SLC6A1 (N=4), MED13L (N=3) and CTNNB1 (N=2) NDDs.

Rated functional categories evaluated included seizures, sleep, communication, behaviors and physical abilities.

Patient responses to acetyl-DL-leucine were categorized as positive, mixed (including positive and negative responses), negative or no response. Responses were defined as "positive" if notable improvements were observed in one or more functional categories, with minimal decline or worsening of symptoms (with the exception of unrelated illnesses and unusual activities). Negative responses were defined as sustained worsening of symptoms with no improvement. Responses were defined as "mixed" if 1) both positive and negative responses were observed at the same time, or 2) sustained improvements were observed followed by loss of effect or worsening of symptoms resulting in discontinuation of acetyl-DL-leucine treatment. Mixed responses were further separated by type of response: 1) including increased behaviors and aggression, or 2) not inducing increased behaviors or aggression. No responses were defined as minimal or unsustained improvements or worsening of symptoms, or no effect as compared to baseline.

Of the 30 patients included in this analysis, 57% (17/30) had a positive response, 27% (8/30) had a mixed response, and 16% (5/30) had no response (none); no negative responses were observed. Of the 13 patients that reported mixed or no response, 85% stopped taking acetyl-DL-leucine prior to the completion of this analysis.

Communication and physical abilities were shown to improve for most patients in the SynGAP1, MED13L and CTNNB1 NDD groups. Only communication improved for most patients for the SLC6A1 NDD group.

Figure 8:
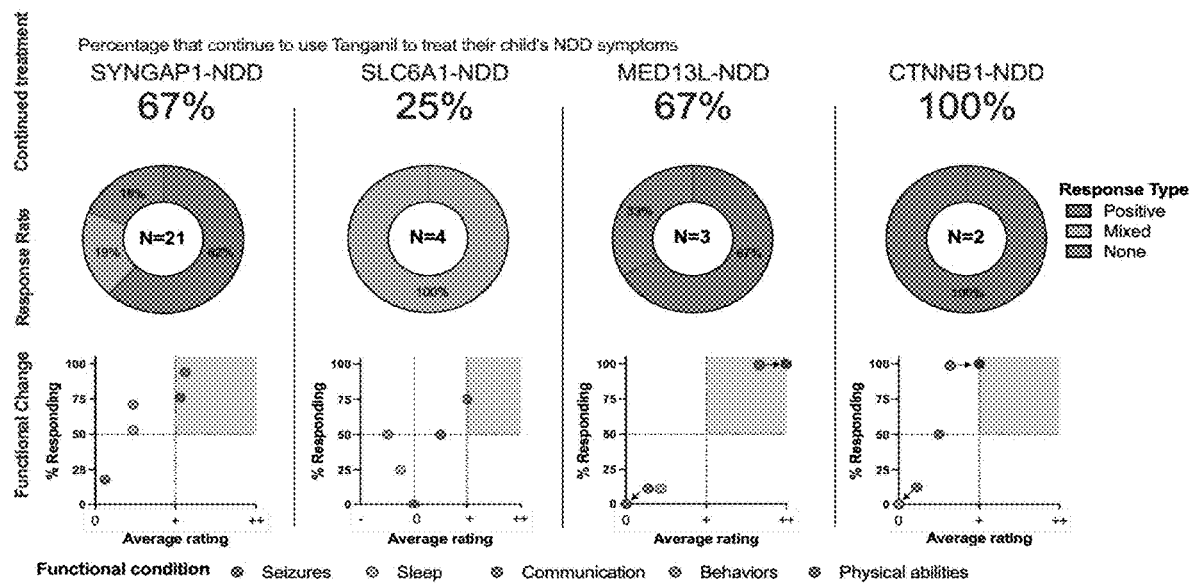
FIG. 8 is a graph showing summary of response and ratings for 4 neurodevelopmental disorders (NDD) of Example 3. Responses to acetyl-DL-leucine treatment were categorized as having a positive, mixed or no response. Responses for each evaluated NDD are shown in columns, including SynGAP1, SLC6A1, MED13L and CTNNB1 NDD groups from left to right. Top) The percentage of patients continuing to use acetyl-DL-leucine at the time of this analysis are shown. Middle) The percentage of patients with each response type were determined. Bottom) The overall areas of functional change were determined for each NDD for response group only, including positive and mixed response groups. The average rating (-=worsening, 0=no change, +=improvement, ++=significant improvement) and percentage of patients reporting a change in each functional condition of seizures, sleep, communication, behaviors or physical abilities are shown.

Patient characteristics, medications and responses to acetyl-DL-leucine are summarized in FIGS. 8 and 9 and Table 2.

Genetic variant type, either protein truncating or missense variant, was reported for 17 patients, 88% had protein truncating variants and 12% had missense variants.

100% (2 out of 2) of the missense variants did not respond to treatment; Patients with protein truncating variants had variable responses to acetyl-DL-leucine treatment.

TABLE 2

|  | Positive response | Mixed response, −agg. | Mixed response, +agg. | No Response |
|---|---|---|---|---|
| % patients | 57% (17/30) | 13% (4/30) | 13% (4/30) | 17% (5/30) |
| Positive changes | Communication Physical abilities | Communication Physical abilities | Communication Physical abilities | None |
| Negative changes | None | Sleep Lost effect | Behaviors | None |
| Age (y): ave (range) | 6 (2-21) | 11 (8-14) | 6 (4-9) | 10 (3-18) |
| Weight (kg): ave (range) | 24 (13-61) | 42 (23-93) | 27 (20-40) | 37 (14-95) |
| Gender: % Female; % Male | 65% F; 35% M | 25% F; 75% M | 75% F; 25% M | 50% F; 50% M; 1 was not reported |
| Variant type (SYNGAP1 only) | 100% PT | 100% PT | 100% PT | 50% PT; 50% MS |
| Max dose (mg/kg): ave (range) | 65 (13-259) | 37 (10-55) | 81 (25-110) | 63 (11-126) |
| Weeks on acetyl-DL-leucine: ave (range) | 9.4 (2-26) | 9.8 (3-17) | 4.0 (2-7) | 4.2 (2-9) |
| # total medications: ave (range) | 2.5 (0-7) | 5.0 (3-9) | 4.5 (3-6) | 1.8 (0-4) |
| # meds for sleep, seizures or beh/anx: ave (range) | 1.4 (0-7) | 2.8 (1-4) | 4.0 (3-5) | 1.0 (0-2) |
| # conditions (sleep, seizures or beh/anx): ave (range) | 0.8 (0-2) | 1.5 (1-2) | 3.0 (3) | 1.0 (0-2) |
| % treated for seizures | 53% | 75% | 100% | 60% |
| % treated for sleep | 12% | 0% | 100% | 40% |
| % treated for beh/anx | 12% | 75% | 100% | 0% |

It was concluded that acetyl-DL-leucine was safe and effective at improving communication and physical abilities with no negative outcomes in 57% of patients. Reported improvements in communication included improvements in understanding and expressive language. Reported improvements in physical abilities included improvements in fine and gross motor skills, coordination, and focus.

It was observed that 26% of patients experienced similar improvements in communication and physical abilities but also had negative outcomes, including loss of effect or increased behaviors/aggressions and concluded that negative outcomes, specifically increased aggressions, were associated with increased range and severity of NDD, as determined by the type and number of existing medications.

It was also concluded that acetyl-DL-leucine is expected to be most beneficial at improving NDD conditions for patients that have minimal issues with sleep, behaviors or anxiety.

Example 4

Impact of Genetic Variant Type on Acetyl-DL-Leucine Response

Impact of genetic variant type on acetyl-DL-leucine response for the SynGAP1 NDD group was evaluated.

Figure 10:
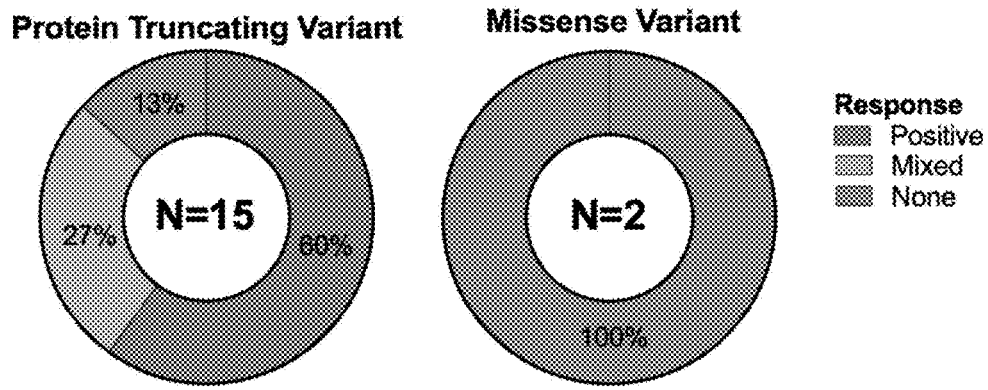
FIG. 10 summarizes the impact of genetic variant type on acetyl-DL-leucine response of Example 4. The percentage of patients in each response group is shown for each genetic variant type.

The results are summarized in FIG. 10.

Example 5

Impact of Patient Characteristics and Dosing on Acetyl-DL-Leucine Response

Figure 11:
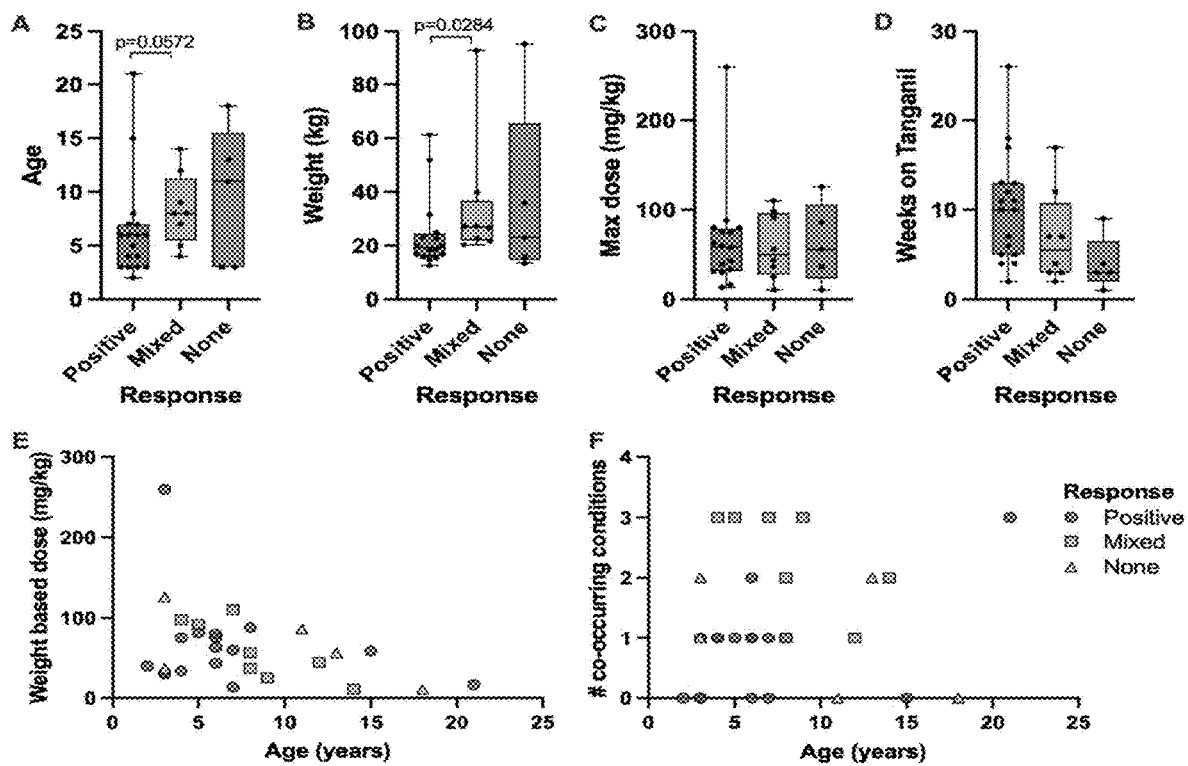
FIG. 11 summarizes impact of patient characteristics and dosing on acetyl-DL-leucine response of Example 5. Differences between acetyl-DL-leucine response groups were evaluated by patient A) age, B) weight, C) maximum acetyl-DL-leucine weight-based dose, and D) acetyl-DL-leucine treatment duration. Statistical differences were determined by Mann Whitney U test. Correlations between patients age and E) maximum acetyl-DL-leucine weight-based dose or F) number of co-occurring conditions, including seizures, sleep, and behaviors or anxiety, were assessed. Statistical analysis was performed using Spearman correlation analysis.

Differences between acetyl-DL-leucine response groups based on patient's age, weight, maximum acetyl-DL-leucine weight-based dose, and acetyl-DL-leucine treatment duration were evaluated. Statistical differences were determined by Mann Whitney U test. Correlations between patients age and maximum acetyl-DL-leucine weight-based dose or number of co-occurring conditions, including seizures, sleep, and behaviors or anxiety, were assessed. The results are summarized in FIG. 11.

No significant difference in patient gender was observed between response groups. Patients that had a positive response to acetyl-DL-leucine treatment were significantly younger and weighed less than the mixed response group. The maximum weight-based dose did not vary significantly between groups. Additionally, the duration of treatment between acetyl-DL-leucine response groups was compared. Individuals with no responses or mixed responses with increased aggression terminated treatment early and therefore had lower treatment durations.

To better understand the impact of age on acetyl-DL-leucine treatment, the correlation between age and weight-based dosing of acetyl-DL-leucine, as well as the number of co-occurring conditions (FIGS. 11E and F, respectively) were evaluated. For the analysis of co-occurring conditions, existing medications used to treat the conditions of seizures, behaviors, anxiety, and sleep were also evaluated. While certain drugs may be used to treat more than one condition, they were sorted based on the condition they are most likely used to treat.

Weight-based acetyl-DL-leucine doses tended to be higher for younger patients, however this overall trend was not significant (FIG. 11E; p=0.1023, r=0.3095). No significant correlation between age and the number of co-occurring conditions overall was observed (FIG. 11F). However, patients with positive response to acetyl-DL-leucine tended to have somewhat lower doses and fewer co-occurring conditions overall, when compared to age matched peers in the mixed response group.

Example 6

Impact of Medications and Treated Conditions on Acetyl-DL-Leucine Response

Figure 12:
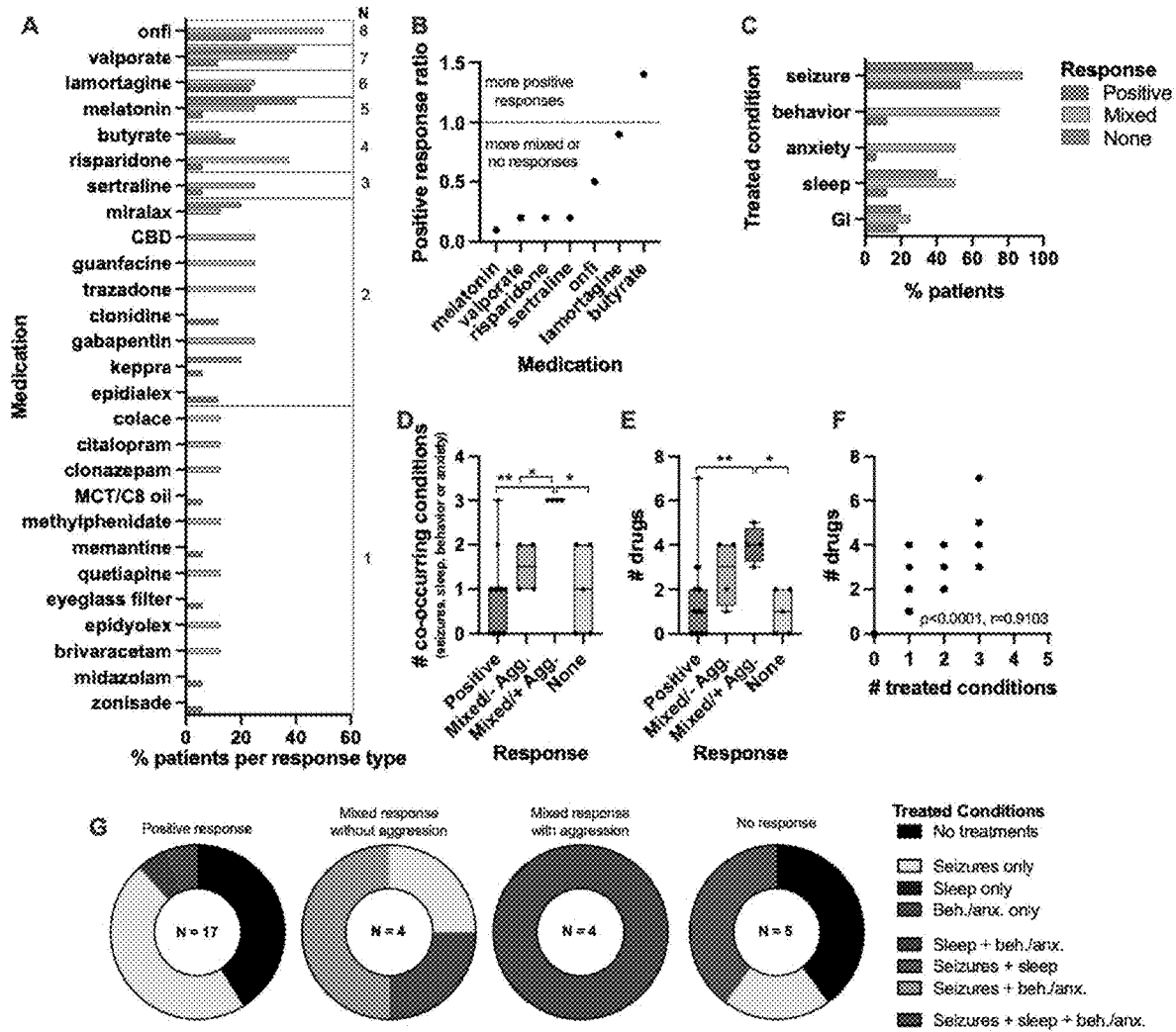
FIG. 12 summarizes impact of medications and treated conditions on acetyl-DL-leucine response of Example 6. A) The percent of patients per response group taking each medication are shown. The number of patients taking each medication is shown to the right of the chart and medications are boxed accordingly. B) A positive response ratio was determined by dividing the percent positive responses by the mixed and no responses for each medication. A positive response ratio >1 indicates the medication associated with positive responses to acetyl-DL-leucine treatment. A positive response ratio <1 indicates the medication associated with mixed or no responses to acetyl-DL-leucine treatment. C) Medications were sorted by treated condition and percentages of patients treated for each condition are shown by response group. D) The number of co-occurring conditions per patient (including seizures, sleep and behavior or anxiety [beh./anx/]) are shown. E) The number of medications taken per patient to treat the conditions of seizures, sleep and behavior or anxiety are shown. Statistical differences were determined by Mann Whitney U test; *=p<0.05, **=p<0.005. F) The correlation between the number of treated conditions and number of drugs was determined. Statistical analysis was performed using Spearman correlation analysis. G) The percentages of patients with individual or co-occurring conditions is shown by the patient's acetyl-DL-leucine response group.

The impact of medication and treated conditions on the patient's response to acetyl-DL-leucine was evaluated. For the analysis of existing medications, only drugs used to treat the conditions of seizures, behaviors or anxiety, and sleep were considered. While certain drugs may be used to treat more than one condition, they were sorted based on the condition they are most likely used to treat. The results are summarized in FIG. 12.

The percentage of patients in each response group taking drugs to treat seizures, behaviors, anxiety, sleep or GI issues are shown in FIG. 12A. The chart is boxed based on the number (N; shown on the right) of patients taking each individual medication. For medications taken by 3 or more patients, a positive response ratio was generated by dividing the percentage of positive responses by the percentage of mixed and no responses. A medication with a positive response ratio >1 was more likely associated with a positive response to acetyl-DL-leucine; a medication with a positive response ratio <1 was more likely associated with a mixed or no response to acetyl-DL-leucine (FIG. 4B). Melatonin, valproate, risperidone and sertraline are associated with mixed or no response to acetyl-DL-leucine, while butyrate is associated with positive responses. These results may indicate contraindications (<1 positive response ratio) or synergy (>1 positive response ratio) with acetyl-DL-leucine or may be associated with increased symptom severity requiring these treatments.

To evaluate the association between symptom severity and response to acetyl-DL-leucine, the treated conditions for each response type were compared (FIG. 12C). Patients with mixed response to acetyl-DL-leucine were more likely to be treated with medications for seizures, behaviors, anxiety and sleep. Few patients with a positive response to acetyl-DL-leucine 1 were being treated for behaviors, anxiety or sleep. This indicates a potential association between NDD symptom range and severity and the outcome of acetyl-DL-leucine treatment.

Next, focusing on the three discriminating conditions of seizures, behaviors or anxiety, and sleep, the number of co-occurring conditions and number of drugs used to treat those conditions for each response group were evaluated (FIGS. 12D and E, respectively). For this analysis, the mixed response group by those that did not have increased aggression (−Agg.) and those that had increased aggression (+Agg.) during acetyl-DL-leucine treatment were separated. The group with mixed response with aggression had significantly higher co-occurring conditions and were using the greatest number of medications for symptom control. The no response group was similar to the positive response group. The number of treated conditions correlated directly with the number of medications (FIG. 12F, p<0.0001, r=0.9103).

To further refine how existing NDD conditions may affect patient response to acetyl-DL-leucine the individual and combinations of conditions by response type were characterized (FIG. 12G). 88% (15/17) of patients with a positive response to acetyl-DL-leucine had no other existing medications or treated conditions or were only being treated for seizures. 12% (2/17) of patients with a positive response to acetyl-DL-leucine were being treated for behaviors or anxiety in combination with other conditions. 88% (7/8) of patients with mixed responses to acetyl-DL-leucine were being treated for behaviors or anxiety in combination with other conditions; 100% of patients with a mixed response with increased aggression were being treated for seizures, sleep and behaviors or anxiety.

These results may indicate that patients with greater range and severity of NDD symptoms, including issues with seizures, behavior or anxiety, or sleep, or those with greater number of existing medications, are more likely to experience a mixed response to acetyl-DL-leucine. Patients that experience issues with all conditions, including seizures, behavior or anxiety, and sleep, may experience increased aggression in response to acetyl-DL-leucine.

Example 7

SYNGAP1-NDD Case Report #1

An 8-year-old boy with SynGAP1-RD was treated orally with 1 gram of acetyl-DL-leucine twice daily (2 grams per day). Parents recorded changes in the patient's seizures, sleep, behaviors, communication, sensory, and GI issues before and during the use of acetyl-DL-leucine for the first 5 weeks.

The medication was well-tolerated, and no safety concerns were noted. Significant improvements in seizure frequency, sleep, and problematic behaviors were observed within the first month of treatment. Within 2 weeks of treatment, the patient had no identifiable seizures during the day. Within 3 weeks of treatment, the patient began sleeping through the night. Within 4 weeks, marked improvements in behaviors were observed by multiple caregivers at home, at school, and during group activities. Improvements in communication and sensory issues were also observed. Minimal improvements were observed for GI issues; an upset stomach was reported at week 5 but may have been unrelated to the administration of acetyl-DL-leucine.

An electroencephalogram (EEG) was performed 7 weeks after starting acetyl-DL-leucine. The patient's neurologist compared results of the post-treatment EEG to the pre-treatment EEG to identify potential differences and provided the following statement: "The patient had an EEG on 9/15/23, then a repeat study on 3/19/24. Both studies were routine in nature and between 35-45 minutes in order to capture sleep. While both studies were abnormal with some slowing and generalized discharges, the second study had a significant decrease in spike burden noted during stage 2 sleep. I would estimate an improvement of about 60-70 percent."

Figure 13:
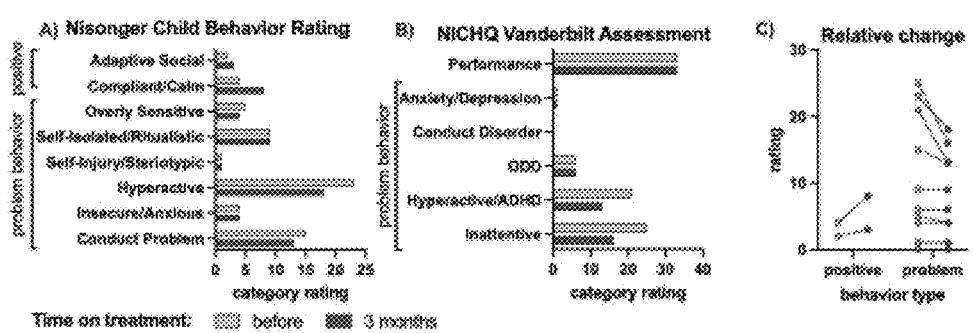
FIG. 13 summarizes results of standardized assessments taken before and 3 months after starting acetyl-DL-leucine treatment of Example 7.

Before and 3 months after starting acetyl-DL-leucine, the parents completed the Nisonger Child Behavior Rating Form and the National Institute for Children's Health Quality (NICHQ) Vanderbilt Assessment Scale. The assessment forms were used to rate positive and problem behaviors as listed in FIG. 13, using the instruction outlined for each assessment. An increase in positive behaviors and decrease in problem behaviors indicate improved function.

Function and behavior changes were rated by parents before and 3 months after starting acetyl-DL-leucine using the Nisonger Child Behavior Rating Form (FIG. 13A) and NICHQ Vanderbilt Assessment Scale (FIG. 13B). The assessment forms were used to rate positive and problem behaviors, then relative changes in overall behaviors were evaluated (FIG. 13C). An overall increase in positive behaviors were observed, most notably an increase in compliant and calm demeanor. A decrease in problem behaviors were observed, most notably a reduction in hyperactivity and inattention.

Notable improvements in the electrical activity in the brain were observed by EEG at 7 weeks. At 3 months the child was calmer, more compliant and showed less inattentive and hyperactive behaviors. After 3 months, the parents were highly satisfied with their child's improvements and continued to include acetyl-DL-leucine in their medication regimen.

Example 8

SYNGAP1-NDD Case Report #2

An 8-year-old boy with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 8 | 27 | SYNGAP1 | PT, c.490 C > T | 17 | 1-1.5 | Guanfacine Sertraline CBD | Mixed response over time |

Figure 14:
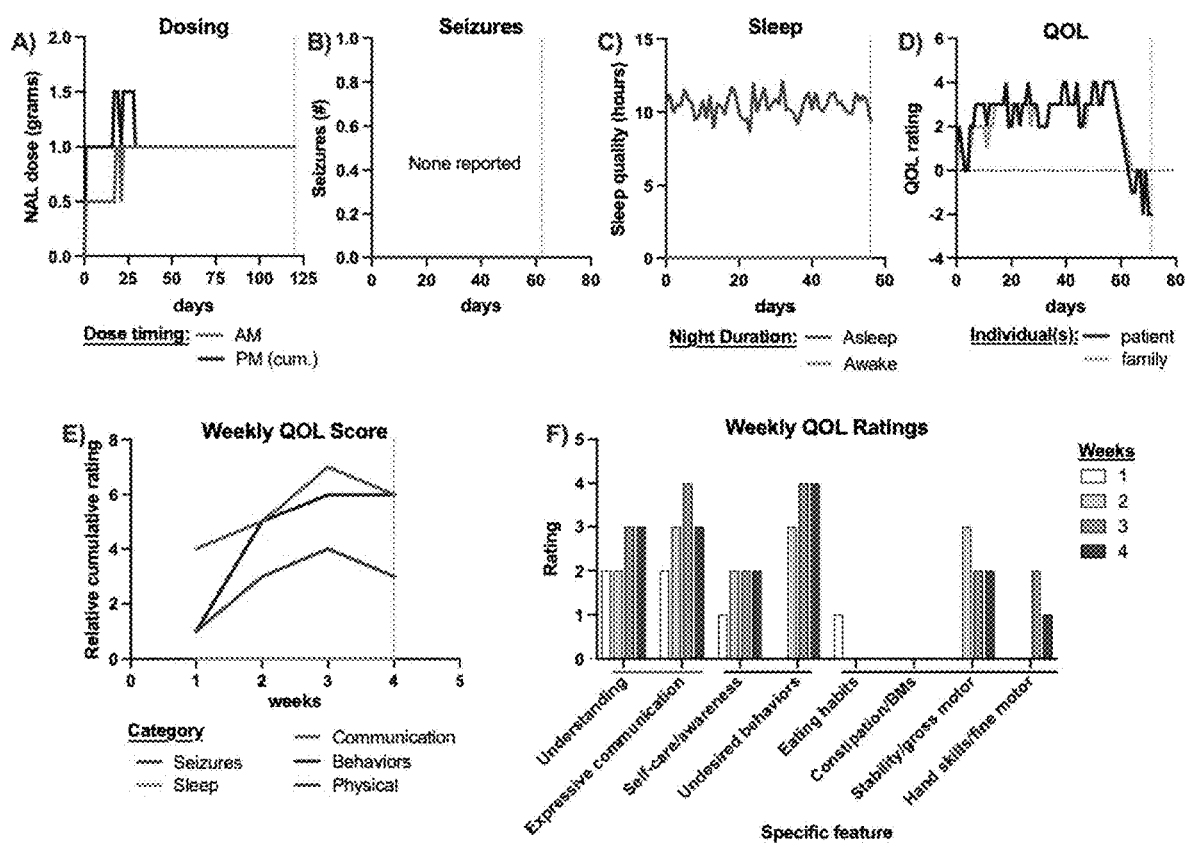
FIG. 14 summarizes results from daily and weekly monitoring of acetyl-DL-leucine effects of Example 8.

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; d) quality of life (QOL) ratings for the patient (blue) and family (pink); +5 (great day) to −5 (terrible day). Parents also provided weekly ratings for changes in features of seizures, sleep, communication, behaviors and physical activities. The ratings were reported on a scale from +5 (really improved) to −5 (much worse). Cumulative ratings for each category and longitudinal ratings for specific features for each category were generated. The results are summarized in FIG. 14.

It was concluded that acetyl-DL-leucine appeared to be safe, well-tolerated, and effective at improving cognition, communication, maladaptive behaviors and physical abilities over the first 8 weeks of treatment.

Example 9

SYNGAP1-NDD Case Report #3

A 21-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 21 | 61 | SYNGAP1 | PT, c.1167_1168delAG | 17 | 0.5-1 | Lamortagine Onfi Midazolam Clonidine Memantine MCT/C8 oil Sertraline | Positive Response |

Parents provided daily monitoring for the following: a) drug dosing, morning dose (AM) and the cumulative (cum.) daily dose after evening (PM); b) number of seizures; c) sleep quality; number of hours asleep and awake during the normal nighttime sleeping period; d) Quality of life (QOL) ratings for the patient and family, +5 (great day) to −5 (terrible day).

Parents also provided weekly ratings for changes in features of seizures, sleep, communication, behaviors and physical activities. The ratings were also reported on a scale from +5 (really improved) to −5 (much worse).

Cumulative ratings for each category and longitudinal ratings for specific features for each category were also generated.

Function and behavior changes were rated by parents before and 3 months after drug treatment using the Nisonger Child Behavior Rating Form and NICHQ Vanderbilt Assessment Scale. The assessment forms were used to rate positive and problem behaviors, then relative changes in overall behaviors were evaluated. An increase in positive behaviors and decrease in problem behaviors indicate improved function. The reduction in problem behaviors was determined to be statistically significant (; p=0.0312 by Wilcoxon matched-pairs signed rank test).

Figure 15:
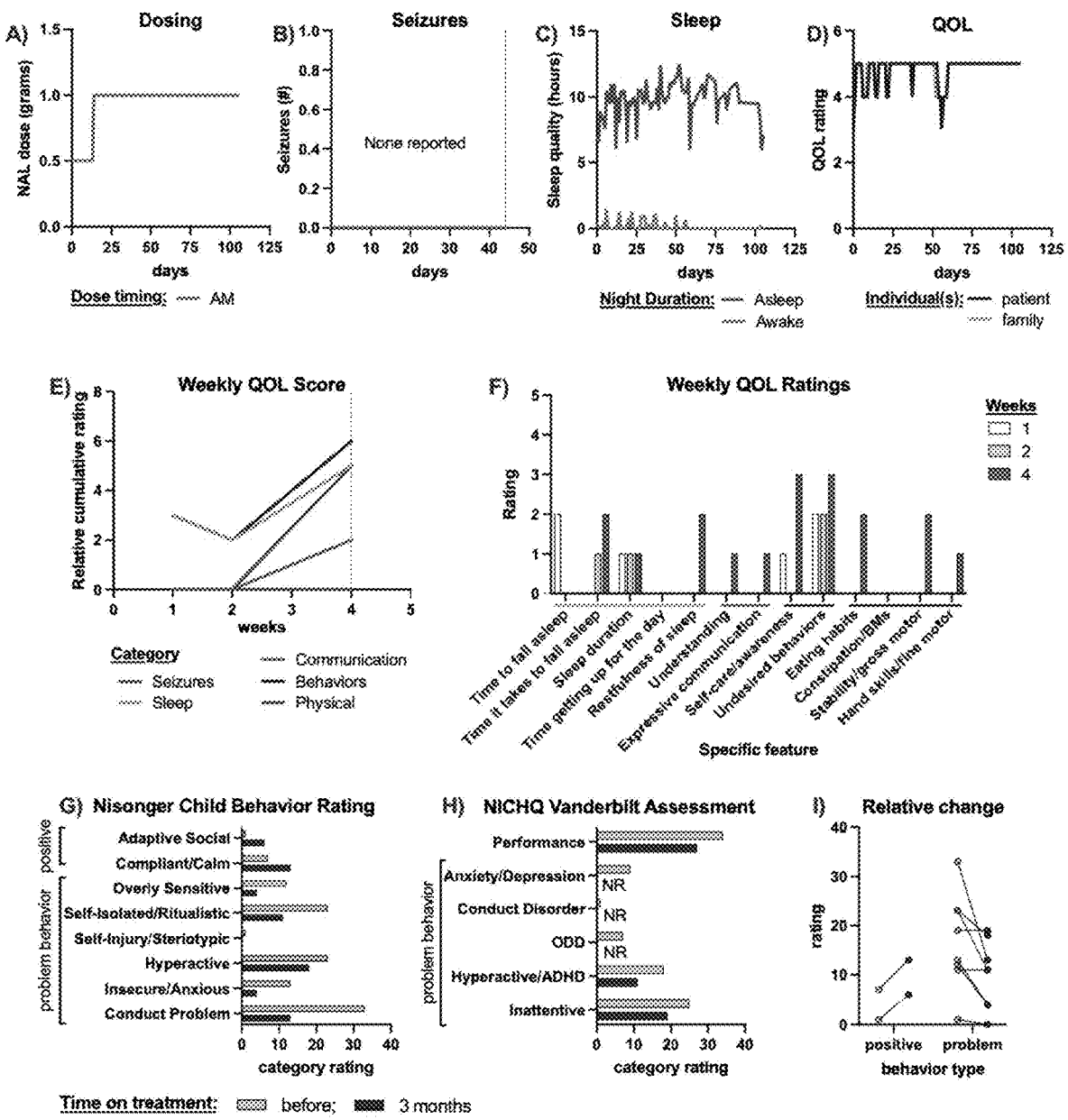
FIG. 15 summarizes results from daily, weekly, and 3-month monitoring of acetyl-DL-leucine effects of Example 9.

The results are summarized in FIG. 15.

It was concluded that acetyl-DL-leucine appeared to be safe, well-tolerated, and effective at improving sleep, cognition, communication, maladaptive behaviors and physical abilities. After 17 weeks, the parents were highly satisfied with their child's improvements and continued to include acetyl-DL-leucine in their medication regimen.

Example 10

SYNGAP1-NDD Case Report #4

A 6-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 6 | 25 | SYNGAP1 | PT, c.1760_1792del33 | 18 | 1-2 | Lamortagine Epidialex | Positive Response |

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse).

Figure 16:
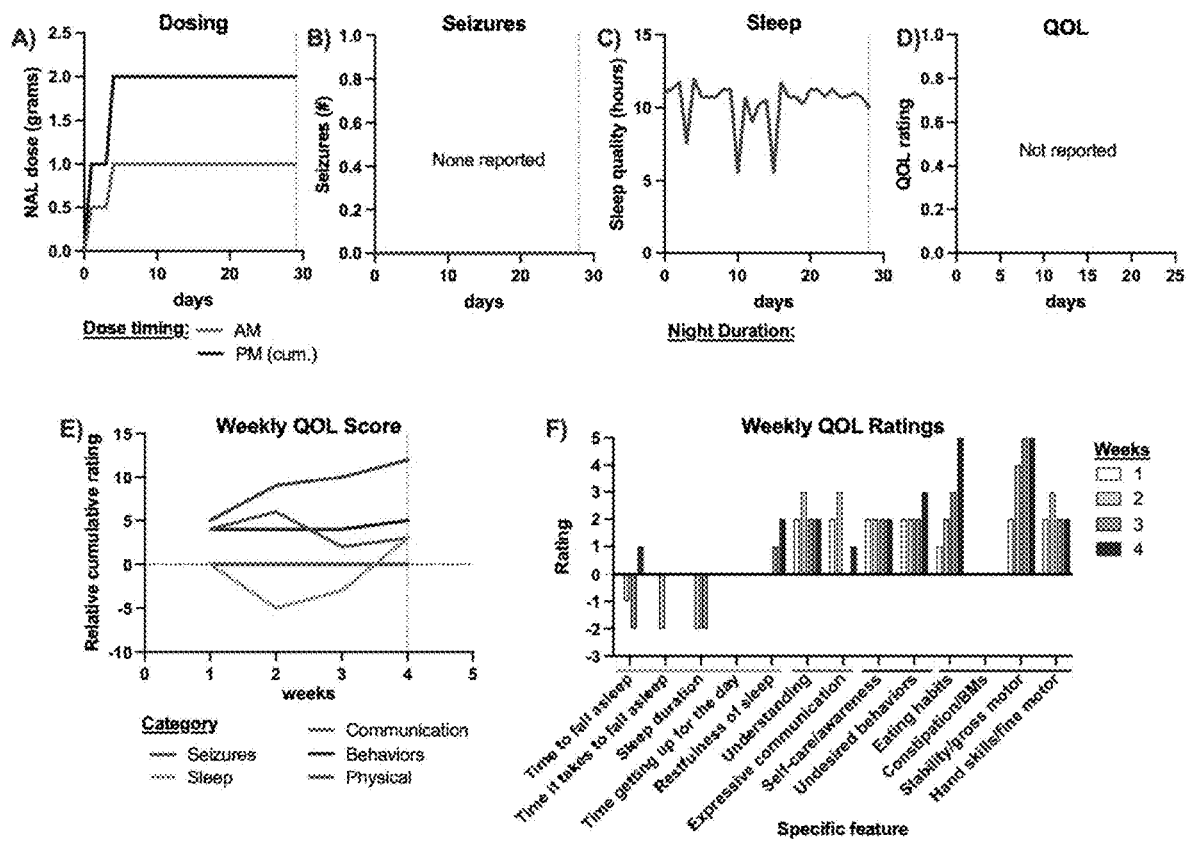
FIG. 16 summarizes results from daily and weekly monitoring of acetyl-DL-leucine effects Of Example 10.

Cumulative ratings for each category and longitudinal ratings for specific features for each category were generated. The results are summarized in FIG. 16.

It was concluded that acetyl-DL-leucine appeared to be safe, well-tolerated, and effective at improving cognition, communication, maladaptive behaviors and physical abilities. After 17 weeks, the parents were highly satisfied with their child's improvements and continued to include acetyl-DL-leucine in their medication regimen.

Example 11

SYNGAP1-NDD Case Report #5

A 13-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 13 | 36 | SYNGAP1 | MS, c.662 A > T | 9 | 0.5-2 | Valporate Melatonin Miralax Vitamin D | No Response |

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; and d) quality of life (QOL) ratings for the patient and family, +5 (great day) to −5 (terrible day). Parents also provided weekly ratings for changes in features of seizures, sleep, communication, behaviors and physical activities; Ratings were also reported on a scale from +5 (really improved) to −5 (much worse). Cumulative ratings and longitudinal ratings for specific features for each category were generated for each category.

Figure 17:
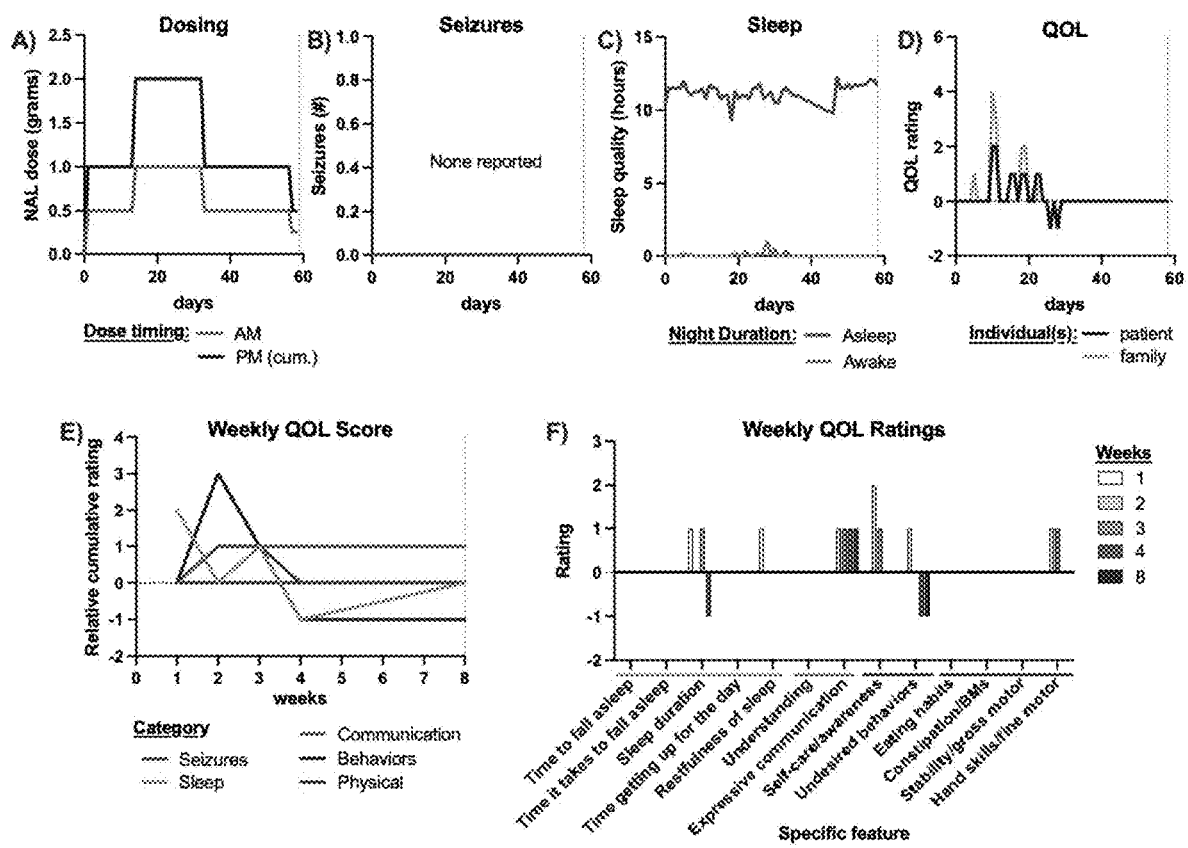
FIG. 17 summarizes results of Example 11.

The results are summarized in FIG. 17.

Example 12

SYNGAP1-NDD Case Report #6

A 7-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 7 | 27 | SYNGAP1 | PT, c.333del | 7 | 1-3 | Valporate Melatonin CBD | Mixed response |

Figure 18:
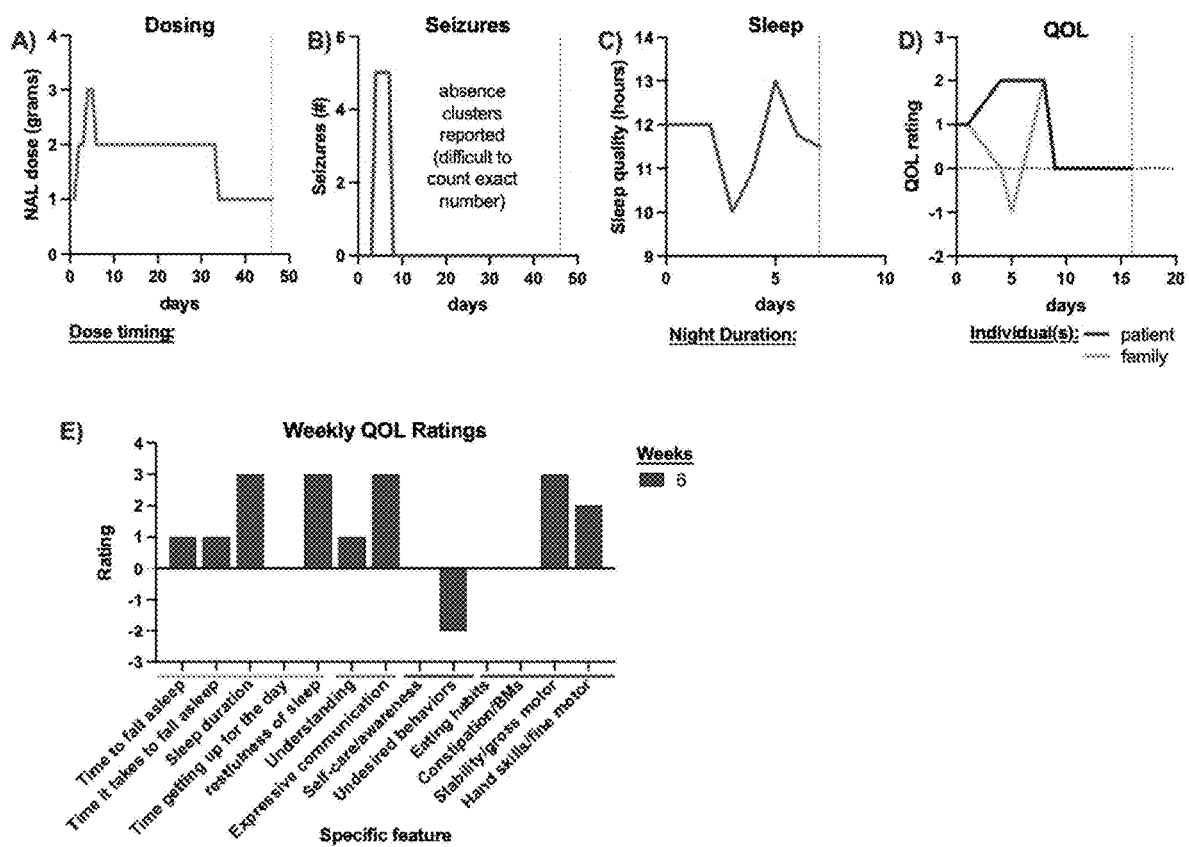
FIG. 18 summarizes results of Example 12.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Longitudinal ratings for specific features for each category were generated. The results are summarized in FIG. 18.

Example 13

SYNGAP1-NDD Case Report #7

A 9-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 9 | 40 | SYNGAP1 | PT, c.3233_32 36delTCAG | 3 | 0.5-1 | Valporate Quetiapine Risparidone Sertraline Miralax | Mixed response |

Figure 19:
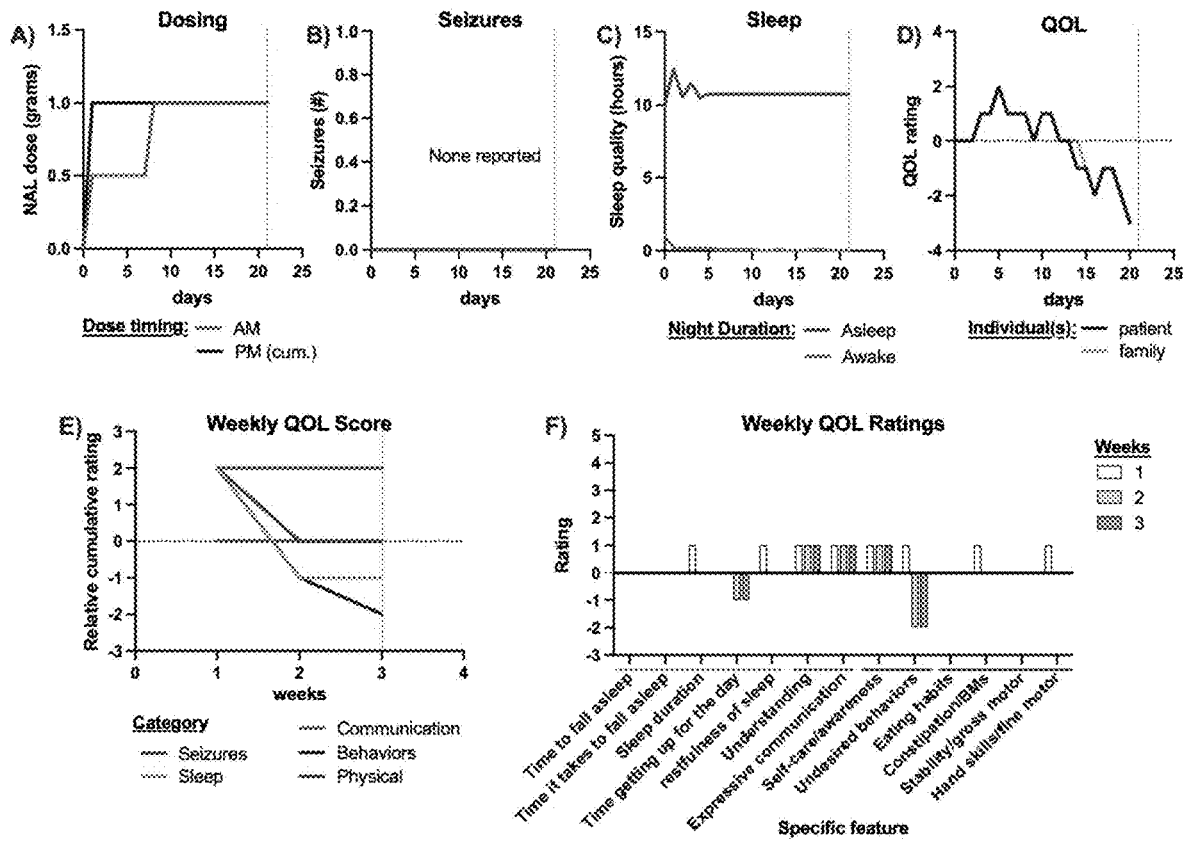
FIG. 19 summarizes results of Example 13.

Parents provided daily monitoring for the following: a) drug dosing, morning dose (AM) and the cumulative (cum.) daily dose after evening (PM); b) number of seizures; c) sleep quality, number of hours asleep and awake during the normal nighttime sleeping period; and d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Cumulative ratings for each category and longitudinal ratings for specific features for each category were generated. The results are summarized in FIG. 19.

Example 14

SYNGAP1-NDD Case Report #8

A 14-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 14 | 93 | SYNGAP1 | PT, c.698_699 dupGT | 7 | 1 | Lamortagine Guanfacine Clonazepam Citalopram Colace Butyrate Iron supplement Mag. Supplement Multivitamin | Mixed response |

Figure 20:
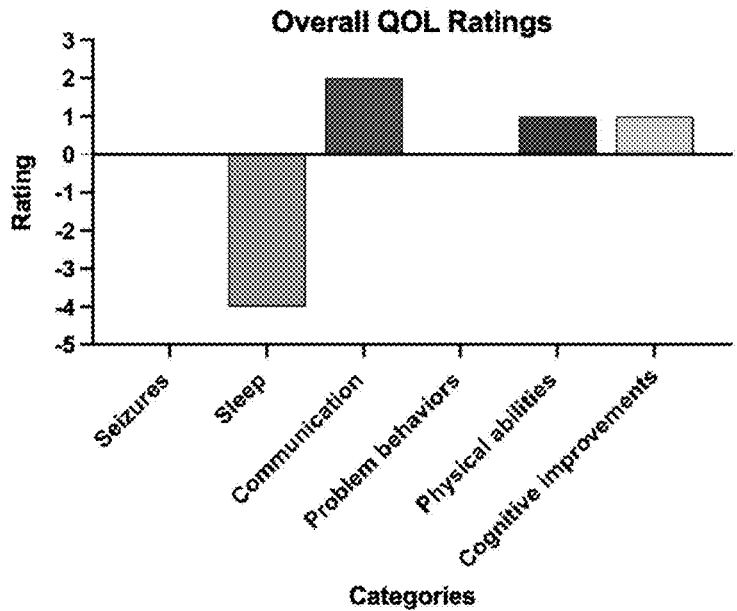
FIG. 20 summarizes results of Example 14.

Parents completed a quick assessment after 7 weeks of treatment. QOL measures, including seizures, sleep, communication, behaviors, physical abilities, and other, were reported. Communication, physical abilities and cognition were reported to have improved. Sleep quality has worsened over the course of the treatment. The results are summarized in FIG. 20.

Example 15

SYNGAP1-NDD Case Report #9

A 2-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 2 | 13 | SYNGAP1 | PT | 11 | 0.5 | Iron supplement | Positive response |

Figure 21:
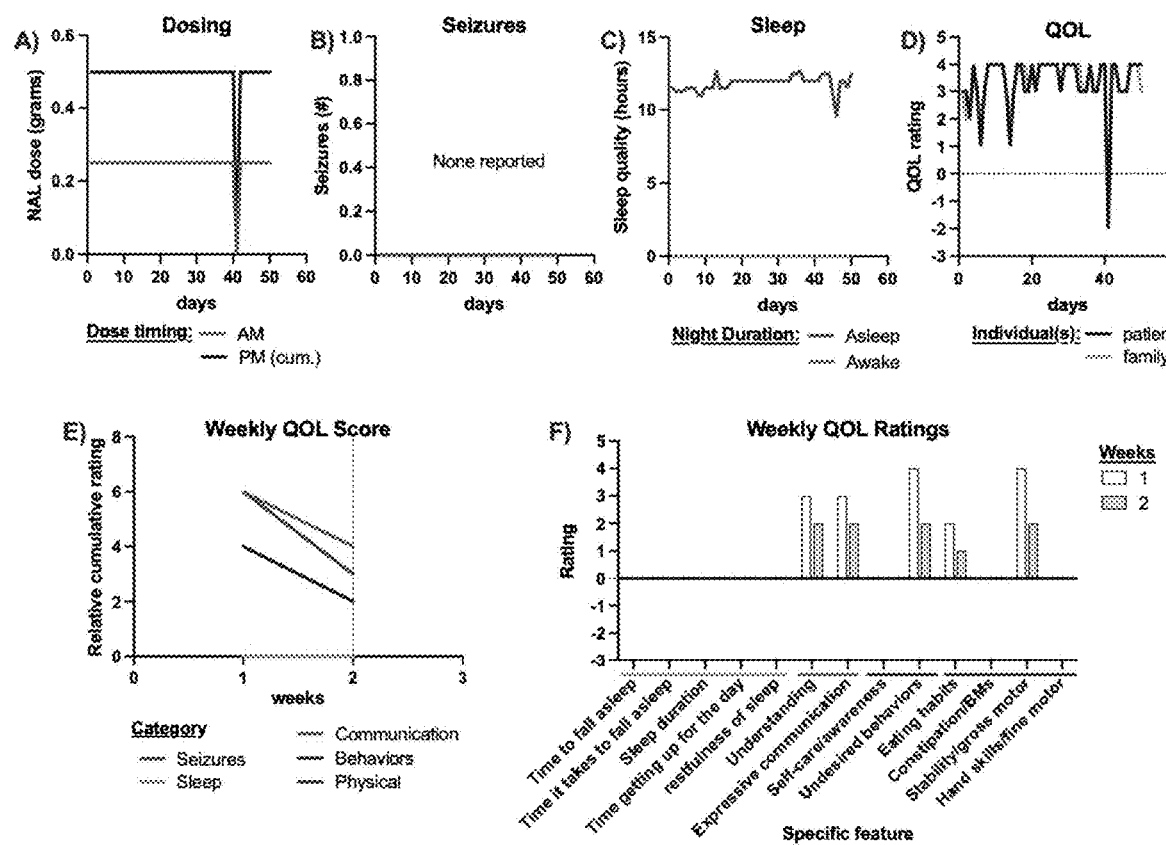
FIG. 21 summarizes results of Example 15.

Parents provided daily monitoring for the following: a) drug dosing, morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Cumulative ratings for each category and longitudinal ratings for specific features for each category were generated. The results are summarized in FIG. 21.

Example 16

SYNGAP1-NDD Case Report #10

A 4-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 4 | 15 | SYNGAP1 | Not reported | 11 | 0.25-0.5 | Lamortagine Onfi | Positive response |

Figure 22:
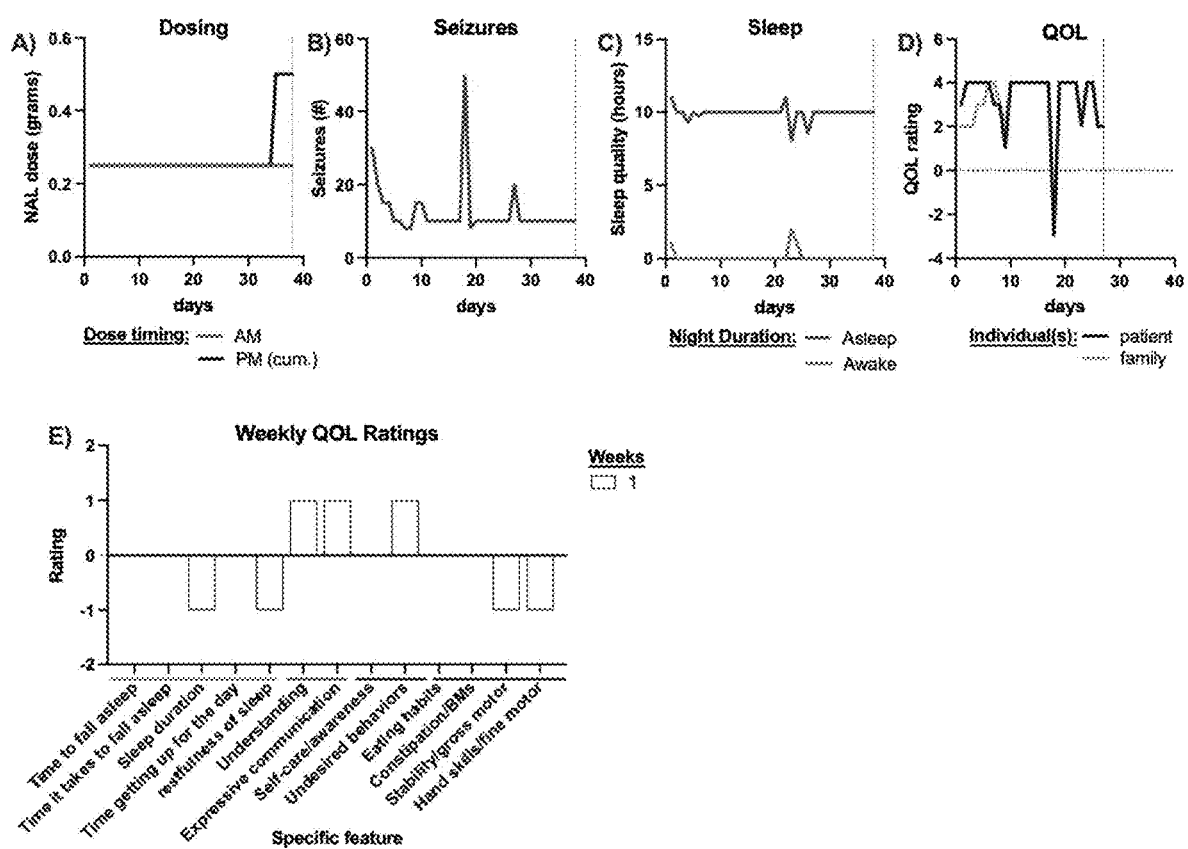
FIG. 22 summarizes results of Example 16.

Parents provided daily monitoring for the following: a) drug dosing, morning dose (AM) and the cumulative (cum.) daily dose after evening (PM); b) number of seizures; c) sleep quality, number of hours asleep and awake during the normal nighttime sleeping period, and d) quality of life (QOL) ratings for the patient and family, +5 (great day) to −5 (terrible day). Parents also provided weekly ratings for changes in features of seizures, sleep, communication, behaviors and physical activities at 1 week only. Ratings were also reported on a scale from +5 (really improved) to −5 (much worse). Longitudinal ratings for specific features for each category demonstrating change over time were generated. The results are summarized in FIG. 22.

Example 17

SYNGAP1-NDD Case Report #11

A 15-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 15 | 52 | SYNGAP1 | PT, c.1677 G > C | 10 | 1-3 | Vitamin D Multivitamin | Positive response |

Figure 23:
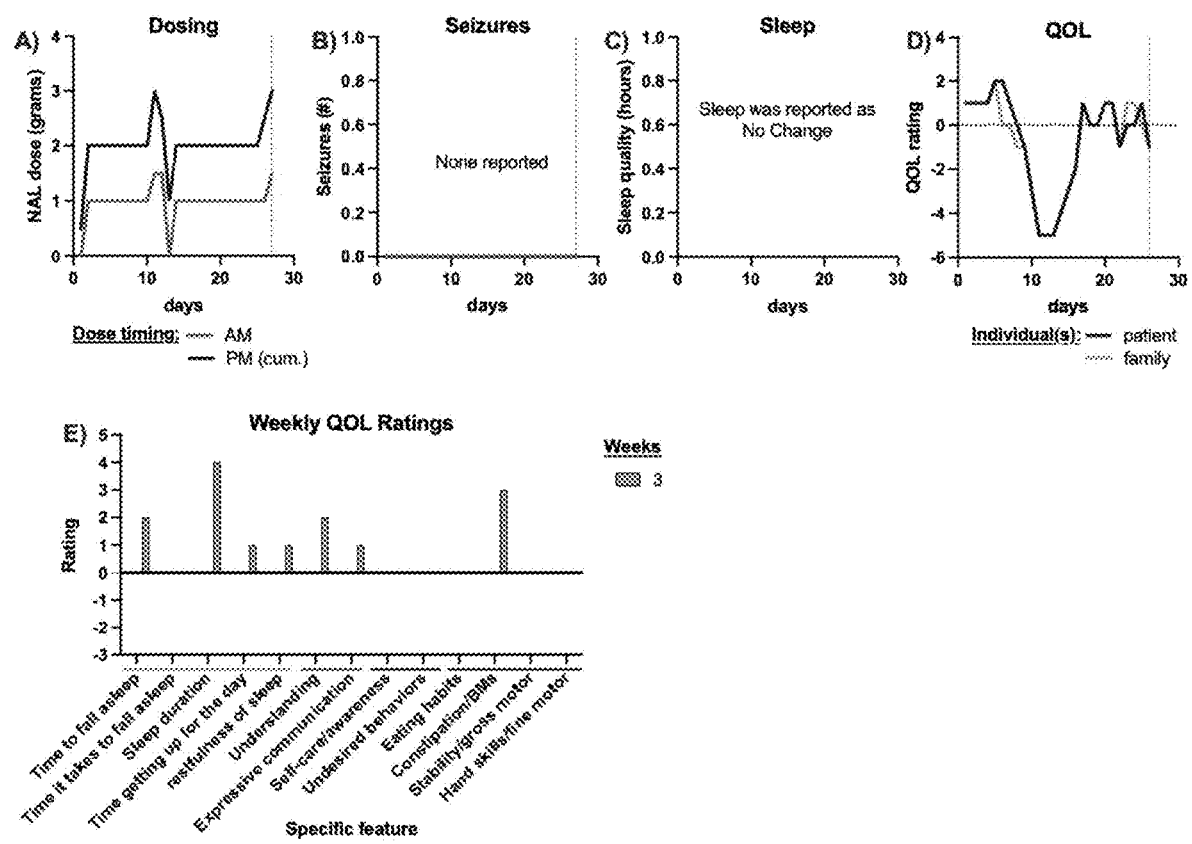
FIG. 23 summarizes results of Example 17.

Parents provided daily monitoring for the following: a) drug dosing, morning dose (AM) and the cumulative (cum.) daily dose after evening (PM); b) number of seizures; c) sleep quality, number of hours asleep and awake during the normal nighttime sleeping period, and d) quality of life (QOL) ratings for the patient and family, +5 (great day) to −5 (terrible day). Parents also provided weekly ratings for changes in features of seizures, sleep, communication, behaviors and physical activities at 1 week only. Ratings were also reported on a scale from +5 (really improved) to −5 (much worse). Longitudinal ratings for specific features for each category were generated. The results are summarized in FIG. 23.

Example 18

SYNGAP1-NDD Case Report #12

A 3-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 3 | 17 | SYNGAP1 | PT, c.2970del | 10 | 0.25-0.5 | Valporate Onfi Zonisade Carnitine | Positive response |

Figure 24:
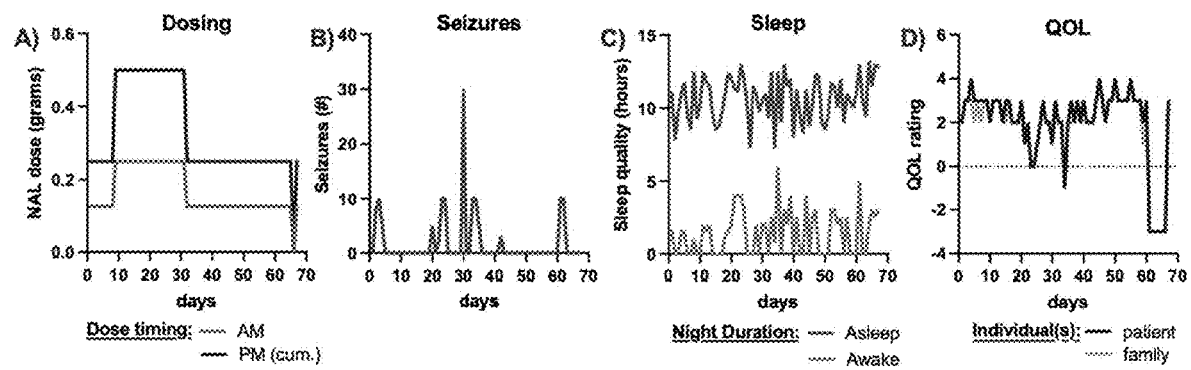
FIG. 24 summarizes results of Example 18.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; and d) quality of life (QOL) ratings for the patient and family, +5 (great day) to −5 (terrible day). The results are summarized in FIG. 24.

Example 19

SYNGAP1-NDD Case Report #13

An 18-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 18 | 95 | SYNGAP1 | MS, c.1030 G > A | 2 | 0.5-1 | None Reported | No response |

Parents used an escalating dose up to 1 gram per day for about 2 weeks and then decided to discontinue treatment. Parents indicated only very minor effects were observed; an increase in oral aversion led to the decision to stop taking acetyl-DL-leucine.

Example 20

SYNGAP1-NDD Case Report #14

A 6-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 6 | 23 | SYNGAP1 | PT | 4 | 1 | Clonidine Melatonin Risparidone | Positive response |

Figure 25:
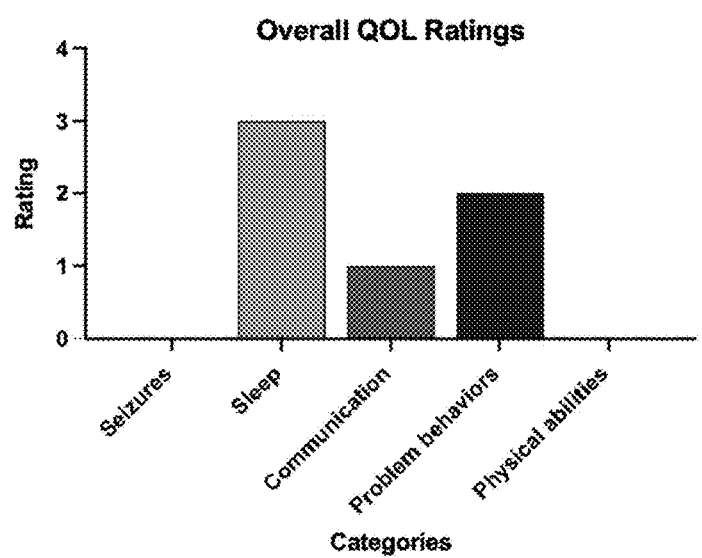
FIG. 25 summarizes results of Example 19.

Parents completed a quick assessment after 4 weeks of acetyl-DL-leucine treatment. QOL measures, including seizures, sleep, communication, behaviors, physical abilities, and other, were reported. The results are summarized in FIG. 25.

Example 21

SYNGAP1-NDD Case Report #15

A 6-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 6 | 20 | SYNGAP1 | PT, p.Gly1126 ValfsTer4 | 12 | 1.5 | Valporate Butyrate | Positive response |

Figure 26:
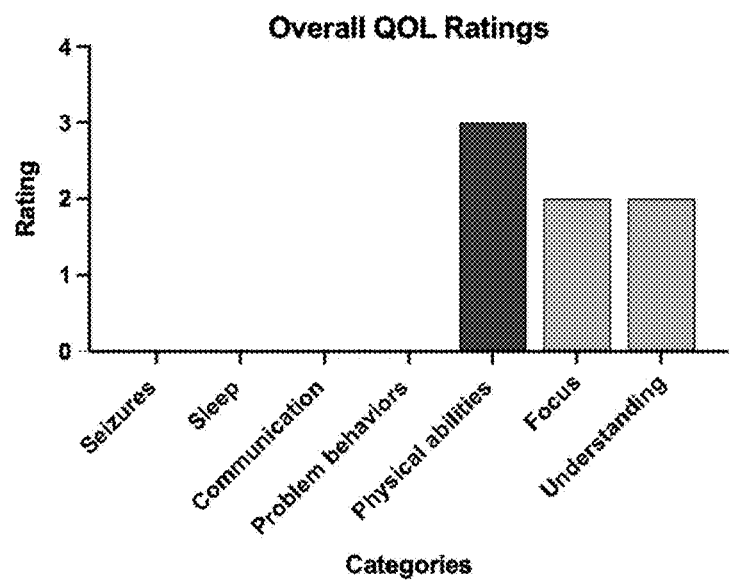
FIG. 26 summarizes results of Example 21.

Parents completed a quick assessment after 12 weeks of acetyl-DL-leucine treatment. QOL measures, including seizures, sleep, communication, behaviors, physical abilities, and other, were reported. The results are summarized in FIG. 26.

Example 22

SYNGAP1-NDD Case Report #16

A 3-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 3 | 16 | SYNGAP1 | PT, c.2320del | 3 | 0.5-2 | Valporate | No response |

Figure 27:
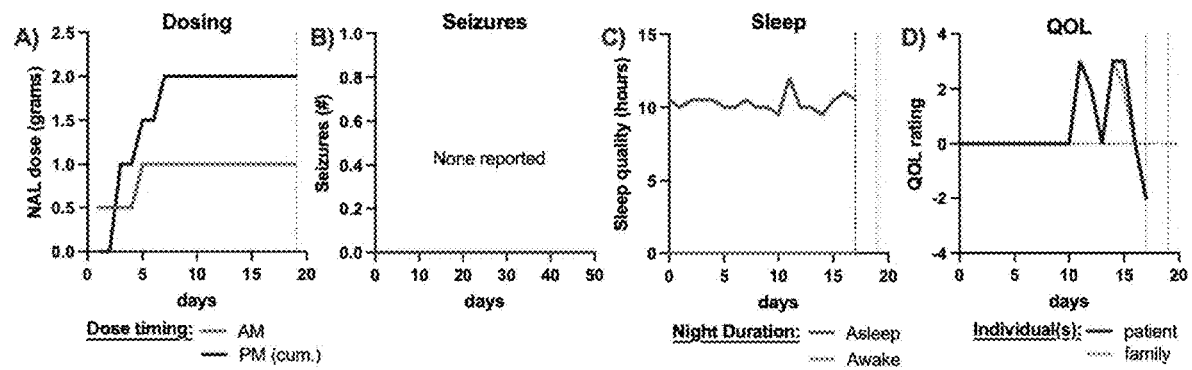
FIG. 27 summarizes results of Example 22.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family, +5 (great day) to −5 (terrible day). The results are summarized in FIG. 27.

Example 23

SYNGAP1-NDD Case Report #17

A 4-year-old male with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 4 | 20 | SYNGAP1 | PT, c.3718 C > T | 13 | 0.5-1.5 | ML41 anti-epileptic eyeglass filter Butyrate | Positive response |

Figure 28:
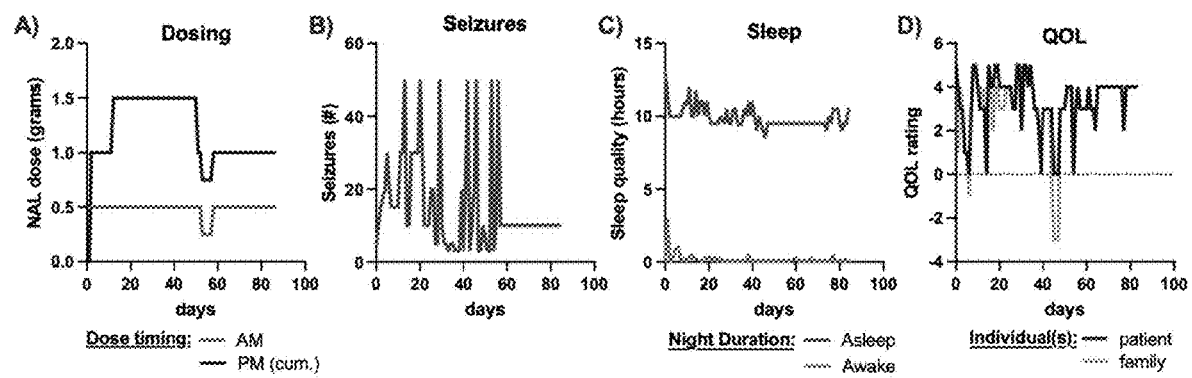
FIG. 28 summarizes results of Example 23.

Parents provided daily monitoring for the following: a) drug dosing; morning dose (AM) and the cumulative (cum.) daily dose after evening (PM); b) number of seizures; c) sleep quality; number of hours asleep and awake) during the normal nighttime sleeping period; d) quality of life (QOL) ratings for the patient and family, +5 (great day) to −5 (terrible day). The results are summarized in FIG. 28.

Example 24

SYNGAP1-NDD Case Report #18

A 5-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 5 | 19 | SYNGAP1 | Not reported | 4 | 0.5-1.5 | Keppra Butyrate Mag. Supplement Vitamin D Multivitamin Carnitine Levocetirizine | Positive response |

Figure 29:
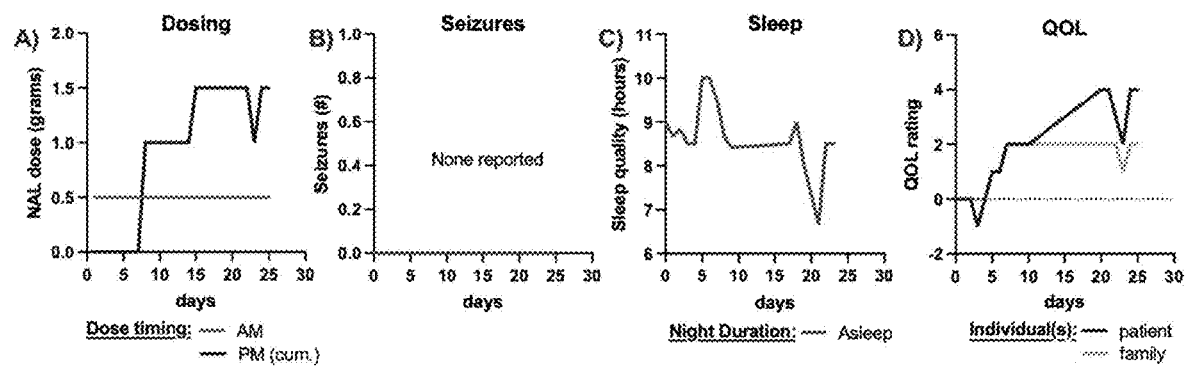
FIG. 29 summarizes results of Example 24.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; and d) Quality of life (QOL) ratings for the patient and family, +5 (great day) to −5 (terrible day). The results are summarized in FIG. 29.

Example 25

SYNGAP1-NDD Case Report #19

A 3-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 3 | 14 | SYNGAP1 | PT, c.2776_2777del | 4 | 0.5 | Keppra Melatonin Multivitamin | No Response |

Figure 30:
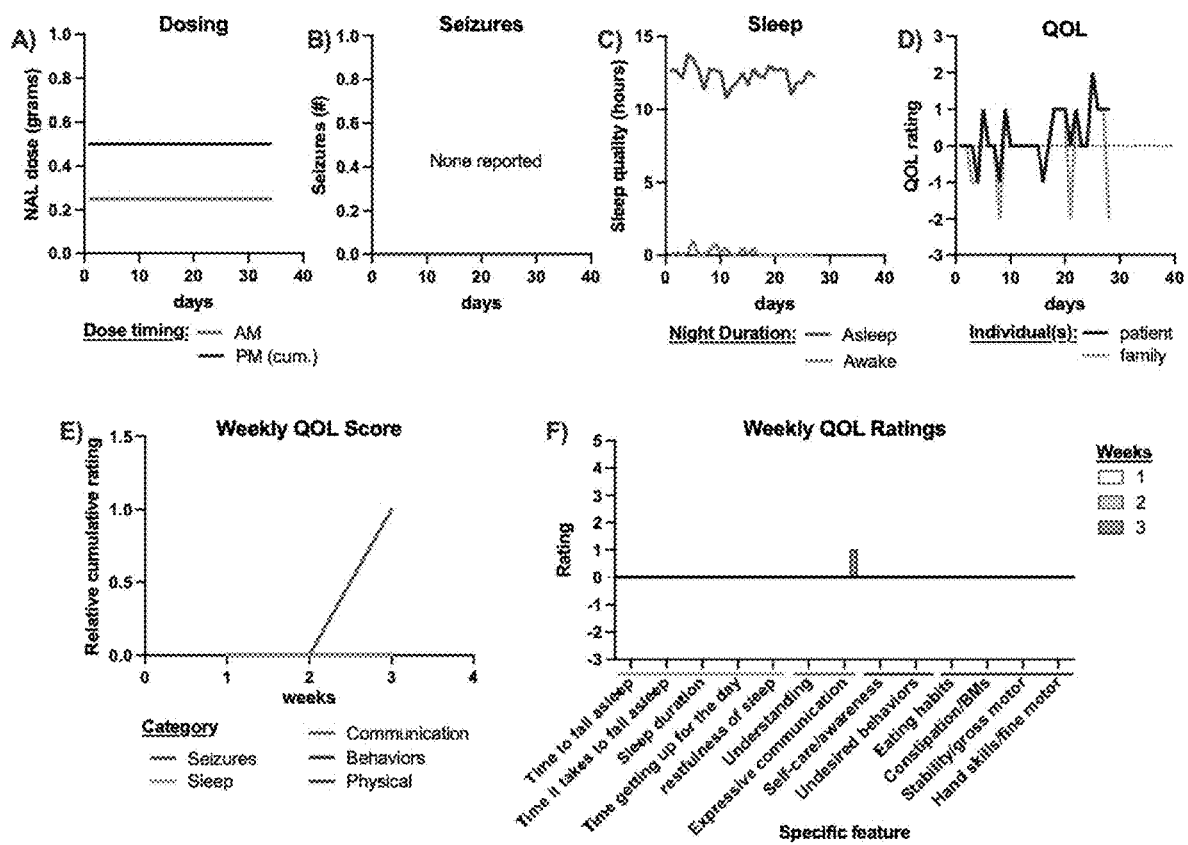
FIG. 30 summarizes results of Example 25.

Parents provided daily monitoring for the following: a) drug dosing; morning dose (AM) and the cumulative (cum.) daily dose after evening (PM); B) number of seizures; c) sleep quality, number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Cumulative ratings for each category and longitudinal ratings for specific features for each category were generated. The results are summarized in FIG. 30.

Example 26

SYNGAP1-NDD Case Report #20

A 3-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 3 | 16 | SYNGAP1 | Not reported | 6 ongoing | 0.25-0.5 | None | Positive response |

Figure 31:
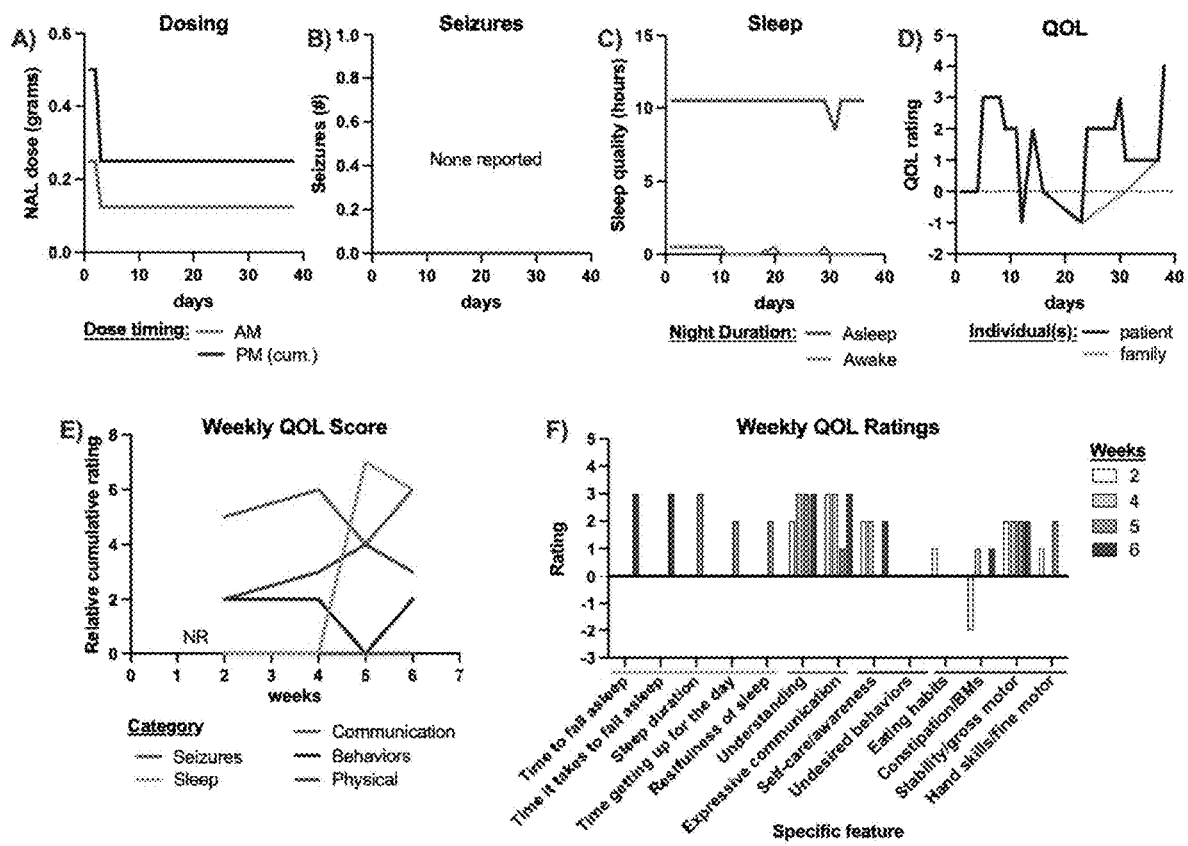
FIG. 31 summarizes results of Example 26.

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Cumulative ratings for each category and longitudinal ratings for specific features for each category were generated. The results are summarized in FIG. 31.

Example 27

SYNGAP1-NDD Case Report #21

A 7-year-old female with SynGAP1-RD was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 7 | 19 | SYNGAP1 | chr6: 3340 9151 G > A | 2 | 0.125-0.25 | Lamortagine | Positive response |

Figure 32:
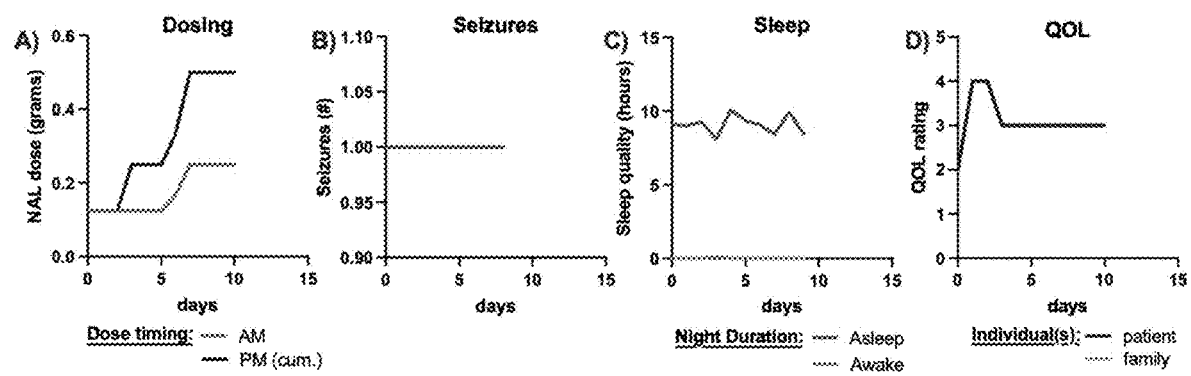
FIG. 32 summarizes results of Example 27.

Parents provided daily monitoring for the following: a) Drug dosing; morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family, +5 (great day) to −5 (terrible day). The results are summarized in FIG. 32.

Example 28

SLC6A1-NDD Case Report #1

A 4-year-old female with SLC6A1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 4 | 20 | SLC6A1 | Not reported | 4 | 2 | Onfi Gabapentin Trazadone Melatonin Risparidone Amantadine | Mixed response |

Figure 33:
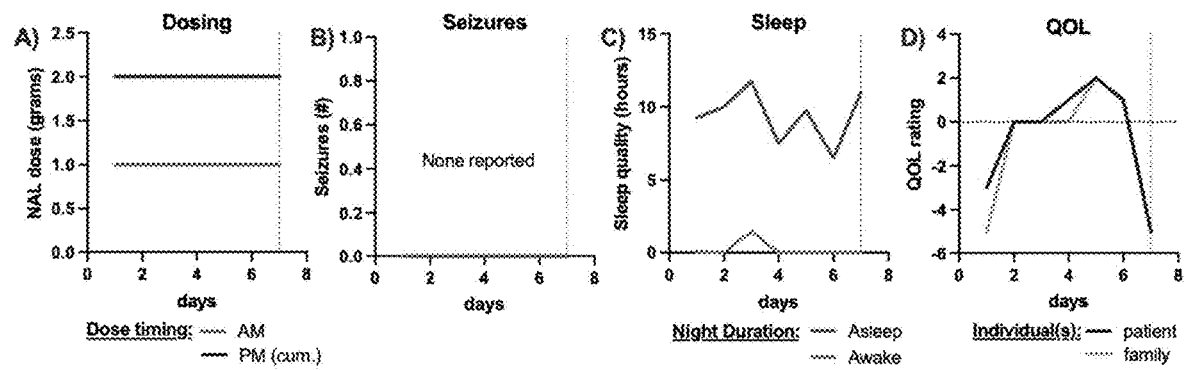
FIG. 33 summarizes results of Example 28.
Figure 34:
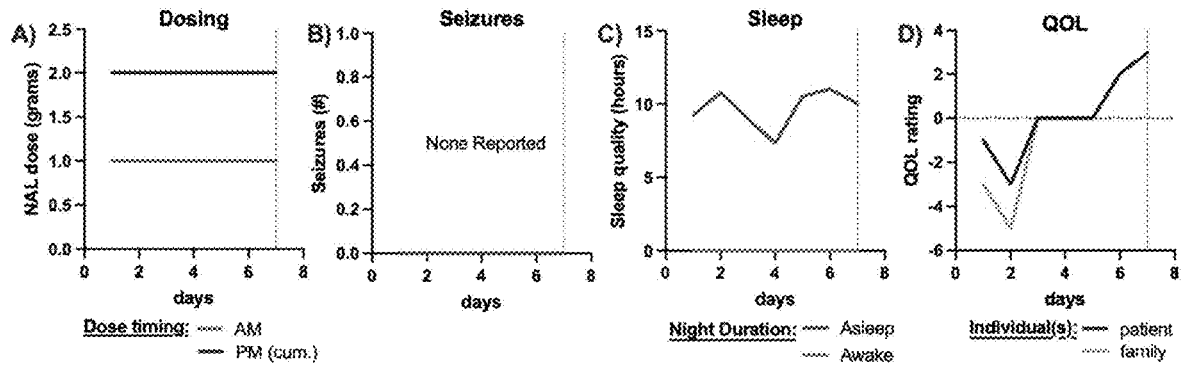
FIG. 34 summarizes results of Example 29.

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period, and d) quality of life (QOL) ratings for the patient (blue) and family (pink), +5 (great day) to −5 (terrible day). The results are summarized in FIG. 33.

Example 29

SLC6A1-NDD Case Report #2

A 5-year-old female with SLC6A1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 5 | 22 | SLC6A1 | Not reported | 2 | 2 | Onfi Gabapentin Trazadone Risparidone | Mixed response |

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; d) quality of life (QOL) ratings for the patient and family, +5 (great day) to −5 (terrible day). The results are summarized in FIG. 29.

Example 30

SLC6A1-NDD Case Report #3

A 12-year-old female with SLC6A1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 12 | 23 | SLC6A1 Down Syn. | MS, Ala 357 Val | 12 | 0.25-1 | Valporate Onfi Brivaracetam Epidyolex Keto Diet | Mixed response |

Figure 35:
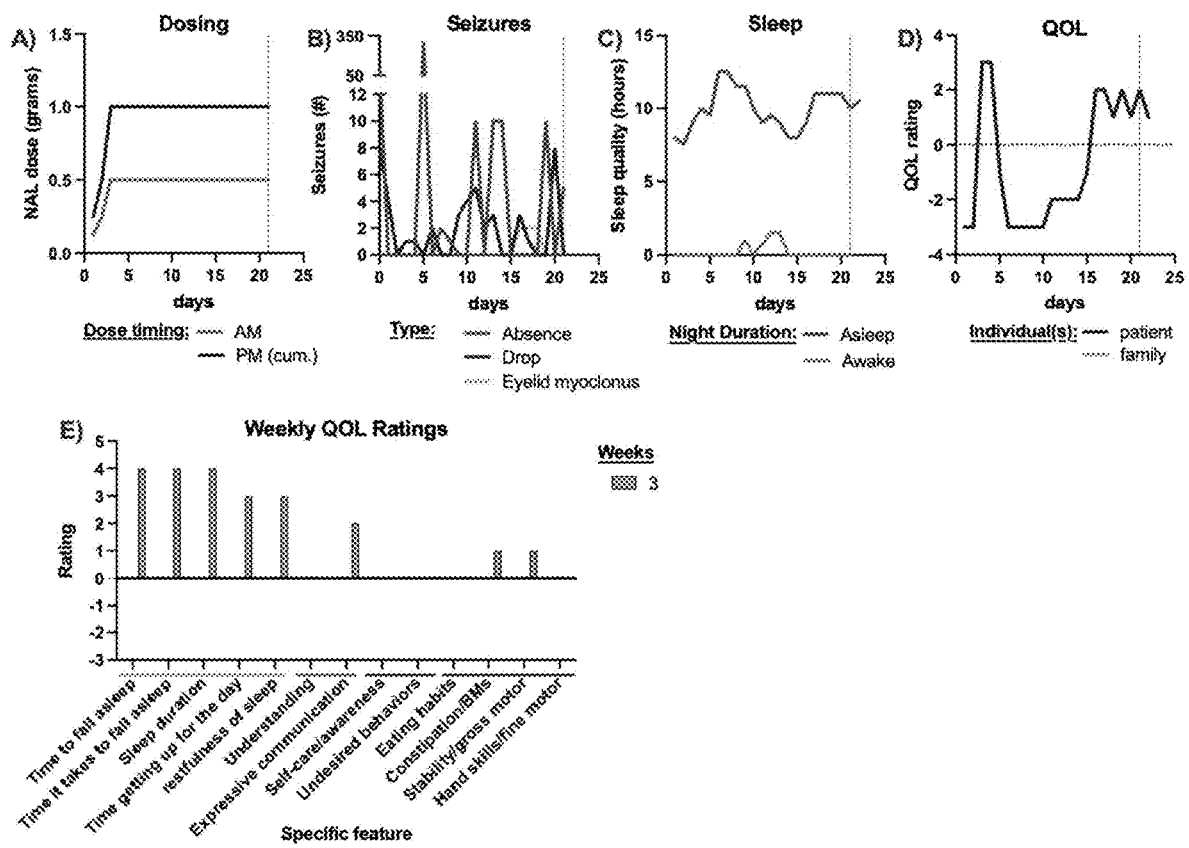
FIG. 35 summarizes results of Example 30.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family, +5 (great day) to −5 (terrible day). Parents also provided weekly ratings for changes in features of seizures, sleep, communication, behaviors and physical activities. Ratings were also reported on a scale from +5 (really improved) to −5 (much worse). Longitudinal ratings for specific features for each category were generated. The results are summarized in FIG. 35.

Example 31

SLC6A1-NDD Case Report #4

An 8-year-old male with SLC6A1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 8 | 27 | SLC6A1 | LOF, c. 1096G > A | 3 | 0.15-1 | Lamortagine Onfi Methylphenidate Aciclovir | Mixed response |

Figure 36:
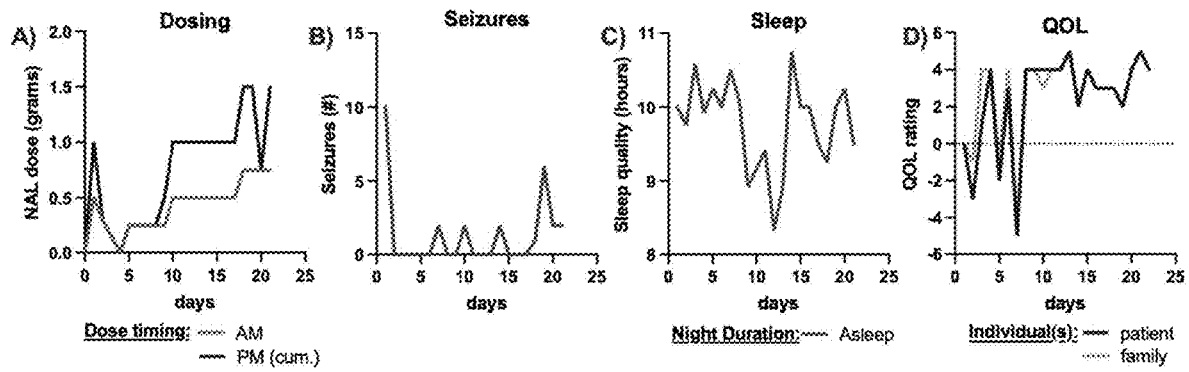
FIG. 36 summarizes results of Example 31.

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; and d) Quality of life (QOL) ratings for the patient (blue) and family (pink), +5 (great day) to −5 (terrible day). The results are summarized in FIG. 36.

Example 32

MED13L-NDD Case Report #1

A 3-year-old male with MED13L was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| M | 3 | 15 | MED13L | Frameshift | 13 | 1-4 | Multivitamin N-acetyl glucosamine N-acetyl cysteine Fish oil Montelukast | Positive response |

Figure 37:
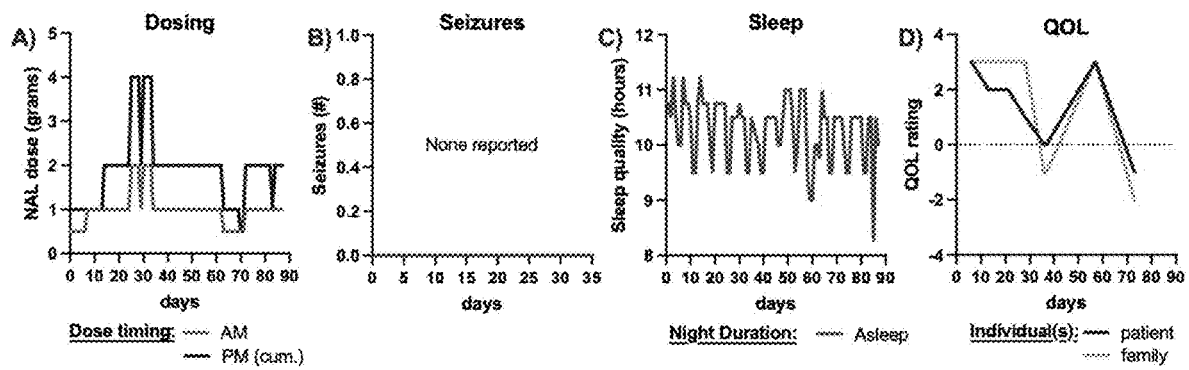
FIG. 37 s summarizes results of Example 32.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; and d) quality of life (QOL) ratings for the patient and family, +5 (great day) to −5 (terrible day). The results are summarized in FIG. 37.

Example 33

MED13L-NDD Case Report #2

An 11-year-old with MED13L was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| NR | 11 | 23 | MED13L | Frameshift/ InDel (VUS) | 3 stopped | 0.5-2 | Levothyroxine | No response |

Figure 38:
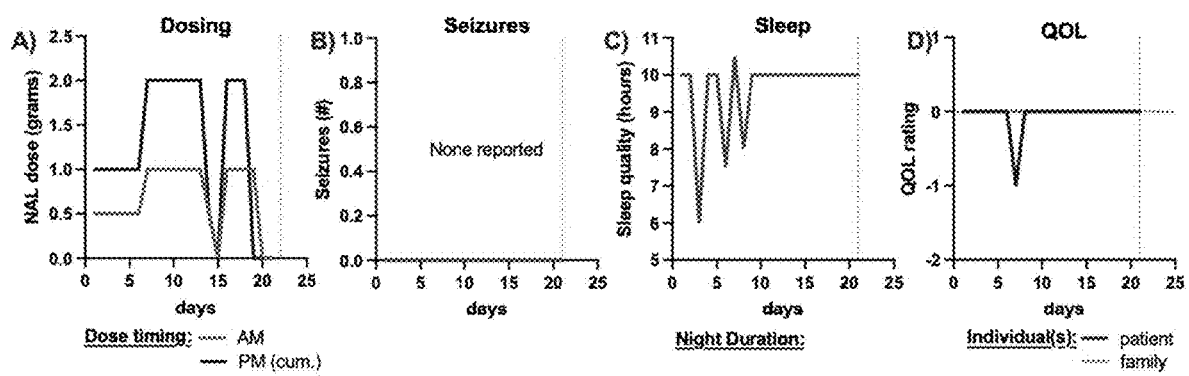
FIG. 38 summarizes results of Example 33.

Parents provided daily monitoring for the following: a) drug dosing; morning dose (AM) and the cumulative (cum.) daily dose after evening (PM); b) number of seizures; c) sleep quality, number of hours asleep and awake during the normal nighttime sleeping period; and d) quality of life (QOL) ratings for the patient and family, +5 (great day) to −5 (terrible day). The results are summarized in FIG. 38.

Example 34

MED13L-NDD Case Report #3

A 3-year-old female with MED13L was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 3 | Not reported | MED13L | Not reported | 5 ongoing | 1-1.5 | None | Positive response |

Figure 39:
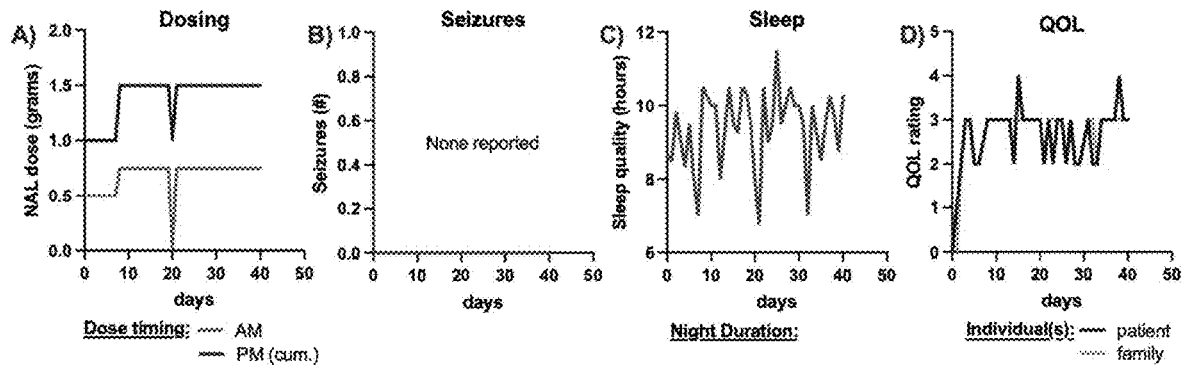
FIG. 39 summarizes results of Example 34.

Parents provided daily monitoring for the following: a) drug dosing; morning dose (AM) and the cumulative (cum.) daily dose after evening (PM); b) number of seizures; c) sleep quality; number of hours asleep and awake during the normal nighttime sleeping period; and d) quality of life (QOL) ratings for the patient (blue) and family (pink), +5 (great day) to −5 (terrible day). The results are summarized in FIG. 39.

Example 35

CTNNB1-NDD Case Report #1

A 7-year-old female with CTNNB1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 7 | 17 | CTNNB1 | Not reported | 5 | 0.5-1 | Trihexyphenidyl Levodopa/carbidopa | Positive response |

Figure 40:
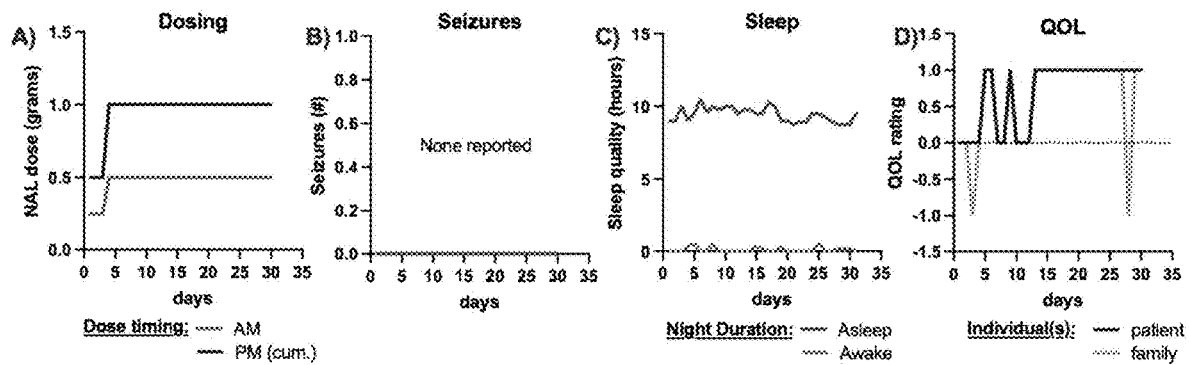
FIG. 40 summarizes results of Example 35.

Parents provided daily monitoring for the following: a) drug dosing; morning dose (AM) and the cumulative (cum.) daily dose after evening (PM); b) number of seizures; c) sleep quality, number of hours asleep (green) and awake (gray) during the normal nighttime sleeping period; d) quality of life (QOL) ratings for the patient and family, +5 (great day) to −5 (terrible day). The results are summarized in FIG. 40.

Example 36

CTNNB1-NDD Case Report #2

A 6-year-old female with CTNNB1 was treated orally with acetyl-DL-leucine as summarized in the following table.

| Sex | Age | Weight (kg) | Condition | Mutation | Weeks on NAL | NAL dose (g) | Existing medications | NAL response |
|---|---|---|---|---|---|---|---|---|
| F | 6 | 32 | CTNNB1 | Nonsense | 7 ongoing | 2 | None | Positive response |

Figure 41:
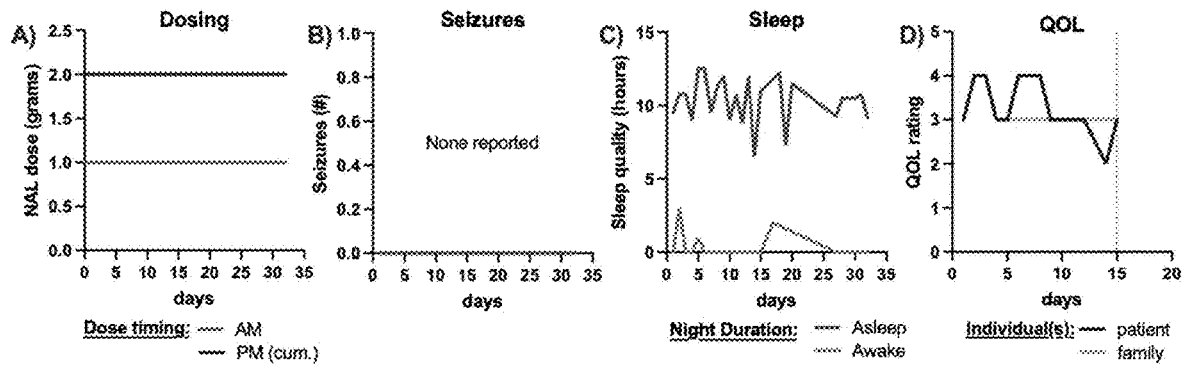
FIG. 41 summarizes results of Example 36.

Parents provided daily monitoring for the following: a) drug dosing, morning dose (AM) and the cumulative (cum.) daily dose after evening (PM); b) number of seizures; c) sleep quality, number of hours asleep and awake during the normal nighttime sleeping period; d) quality of life (QOL) ratings for the patient and family (pink), +5 (great day) to −5 (terrible day). The results are summarized in FIG. 41.

Example 37

KCNT1 Case Report #1

A 7-year-old male with KCNT1 was treated orally with acetyl-DL-leucine as summarized in the following table.

| Sex | Age | Weight (kg) | Condition | Weeks on NAL | NAL dose (g) | NAL response |
|---|---|---|---|---|---|---|
| M | 7 | 4 | KCNT1 | 4 | 250 mg/day to 1 g/day | Positive response |

In weeks 1-2, parents reported improved eye contact and increased vocalization.

Example 38

Figure 42A:
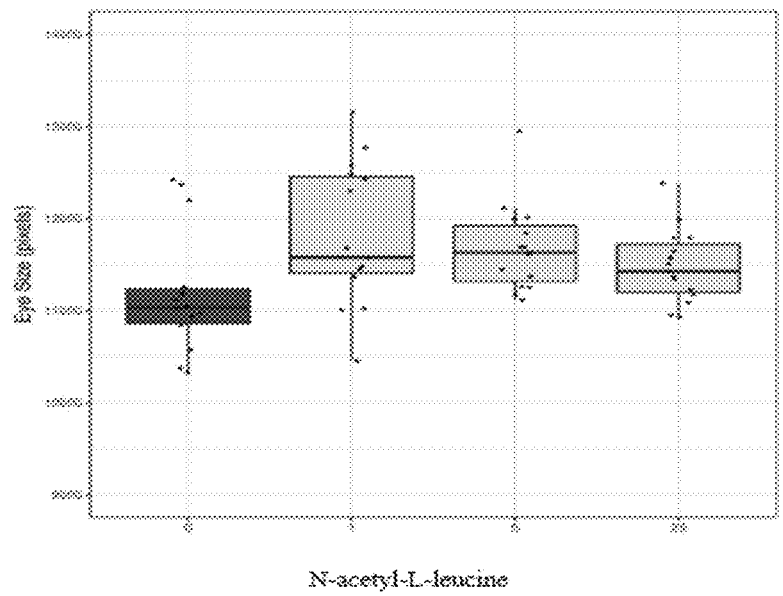
FIG. 42A depicts the eye size effect of NALL on raskol *Drosophila* eye phenotype over multiple drug dilutions from Example 38. Increased eye size over control (dark grey) indicates improved phenotype. Increased eye size over control (dark grey) indicates improved phenotype.
Figure 42B:
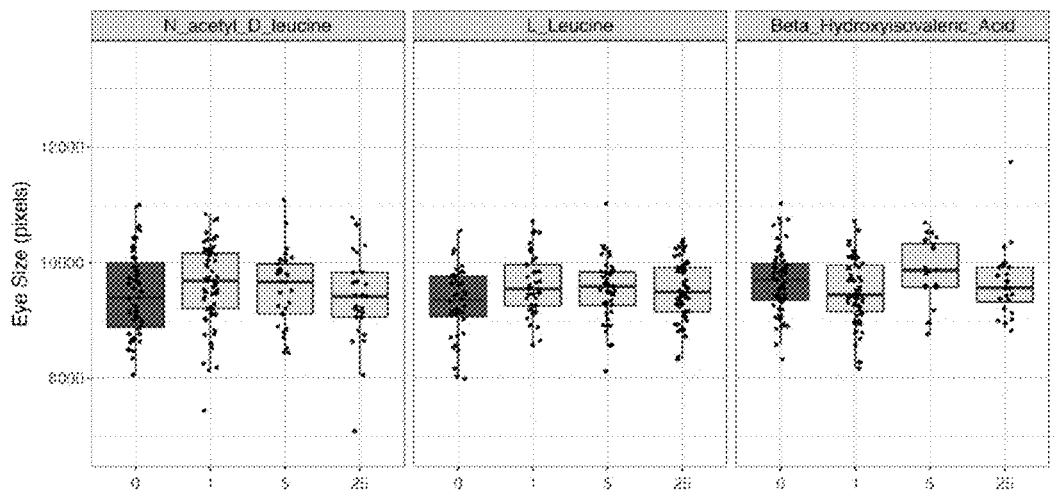
FIG. 42B depicts the eye size effect of NADL, L-Leucine and beta-hydroxyisovaleric acid on raskol *Drosophila* eye phenotype over multiple drug dilutions from Example 38. NADL, L-Leucine and beta-hydroxyisovaleric do not have a significant effect on phenotype recovery, as was observed with NALL.

To evaluate the effect of NALL, in comparison with NADL and L-leucine, the eye phenotype recovery assay was repeated with NADL, L-Leucine and Beta-hydroxyisovaleric acid. Results from this experiment are depicted in FIGS. 42A and 42B and demonstrate that neither NADL nor L-Leucine have a significant effect on phenotype recovery, as was observed with NALL.

Induced seizures in raskol Drosophila were also evaluated in the absence or presence of drug treatment, including NALL or NADL. Drosophila treated with NALL had a faster recovery time, more similar to wild type Drosophila, as compared to untreated or NADL treated raskol Drosophila.

Finally, RNAseq was performed to compare gene regulation differences between raskol Drosophila untreated and NALL-treated flies. Down regulated genes were enriched for tyrosine catabolic processes, as shown in FIG. 43C.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

While the invention has been disclosed with reference to specific embodiments, it is apparent that other embodiments and variations of this invention may be devised by others skilled in the art without departing from the true spirit and scope of the invention. All patents and publications cited herein are incorporated by reference in their entirety. The appended claims are intended to be construed to include all such embodiments and equivalent variations.

What is claimed is:

1. A method for treating a neurodevelopmental disorder comprising administering to a subject in need thereof a therapeutically effective amount of a compound of Formula (I):

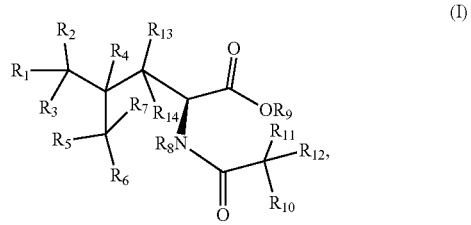

(I)

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is each independently H or D; or a pharmaceutically acceptable salt thereof.

2. The method of claim 1, wherein the neurodevelopmental disorder is selected from a group consisting of SYNGAP1-Related Disorder, SLC6A1-Related disorder, MED13L syndrome, CTNNB1 syndrome, DLG4-related synaptopathy, KCNT1 epilepsy, FOXG1 syndrome, Autism Spectrum Disorder, Attention-Deficit Disorder and Intellectual Disability.

3. The method of claim 1, wherein the neurodevelopmental disorder is a developmental and epileptic encephalopathy.

4. The method of claim 3, wherein the developmental and epileptic encephalopathy is SYNGAP1-Related Disorder.

5. The method of claim 1, wherein the compound of Formula (I) is N-acetyl-L-leucine.

6. The method of claim 5, wherein N-acetyl-L-leucine is administered orally.

7. The method of claim 6, wherein from about 100 mg to about 5 grams of N-acetyl-L-leucine is administered per day.

8. The method of claim 6, wherein N-acetyl-L-leucine is administered in a pharmaceutical composition comprising N-acetyl-L-leucine and one or more pharmaceutically acceptable excipients.

9. The method of claim 8, wherein the pharmaceutical composition further comprises N-acetyl-D-leucine.

10. The method of claim 8, wherein the pharmaceutical composition consists of N-acetyl-L-leucine and one or more pharmaceutically acceptable excipients.

11. The method of claim 8, wherein the pharmaceutical composition is a solution comprising N-acetyl-L-leucine dissolved in a pharmaceutically acceptable solvent.

12. The method of claim 6, wherein N-acetyl-L-leucine is administered twice or three times a day.

13. The method of claim 1, wherein the subject is a carrier of a SYNGAP1 pathogenic gene mutation.

14. A method for treating a neurodevelopmental disorder comprising administering to a subject in need thereof a therapeutically effective amount of N-acetyl-DL-leucine.

15. The method of claim 14, wherein the neurodevelopmental disorder is selected from a group consisting of SYNGAP1-Related Disorder, SLC6A1-Related disorder, MED13L syndrome, CTNNB1 syndrome, DLG4-related synaptopathy, KCNT1 epilepsy, FOXG1 syndrome, Autism Spectrum Disorder, Attention-Deficit Disorder and Intellectual Disability.

16. The method of claim 14, wherein the neurodevelopmental disorder is a developmental and epileptic encephalopathy.

17. The method of claim 14, wherein N-acetyl-DL-leucine is administered orally.

18. The method of claim 17, wherein N-acetyl-DL-leucine is administered twice or three times a day.

19. The method of claim 14, wherein N-acetyl-DL-leucine is administered in a pharmaceutical composition comprising N-acetyl-DL-leucine and one or more pharmaceutically acceptable excipient(s), and the pharmaceutical composition is a liquid comprising N-acetyl-DL-leucine dissolved in a solvent.

20. The method of claim 17, wherein from about 200 mg to about 10 grams of N-acetyl-DL-leucine is administered per day.

* * * * *